United States Patent
Huang et al.

(10) Patent No.: US 11,161,897 B2
(45) Date of Patent: Nov. 2, 2021

(54) ANTIGEN BINDING REGIONS AGAINST FIBRONECTIN TYPE III DOMAINS AND METHODS OF USING THE SAME

(71) Applicant: Janssen Biotech, Inc., Horsham, PA (US)

(72) Inventors: Chichi Huang, Berwyn, PA (US); John Lee, Philadelphia, PA (US); Jill Mooney, San Diego, CA (US); Michael Naso, Swarthmore, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 16/037,340

(22) Filed: Jul. 17, 2018

(65) Prior Publication Data

US 2019/0016789 A1  Jan. 17, 2019

Related U.S. Application Data

(60) Provisional application No. 62/533,341, filed on Jul. 17, 2017, provisional application No. 62/625,576, filed on Feb. 2, 2018.

(51) Int. Cl.
| | |
|---|---|
| *C07K 16/28* | (2006.01) |
| *C07K 16/46* | (2006.01) |
| *C07K 14/735* | (2006.01) |
| *A61K 39/395* | (2006.01) |
| *C07K 16/18* | (2006.01) |

(52) U.S. Cl.
CPC .......... *C07K 16/18* (2013.01); *C07K 2317/56* (2013.01); *C07K 2317/565* (2013.01); *C07K 2317/622* (2013.01); *C07K 2319/02* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,560,655 A | 12/1985 | Baker |
| 4,657,866 A | 4/1987 | Kumar |
| 4,767,704 A | 8/1988 | Cleveland et al. |
| 4,927,762 A | 5/1990 | Darfler |
| 5,122,469 A | 6/1992 | Mather et al. |
| 5,827,642 A | 10/1998 | Riddell et al. |
| 5,858,358 A | 1/1999 | June et al. |
| 5,883,223 A | 3/1999 | Gray |
| 6,040,177 A | 3/2000 | Riddell et al. |
| 6,352,694 B1 | 3/2002 | June et al. |
| 6,534,055 B1 | 3/2003 | June et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 8,278,419 B2 | 10/2012 | Jacobs et al. |
| 2005/0208048 A1 | 9/2005 | McMahan et al. |
| 2006/0121005 A1 | 6/2006 | Berenson et al. |
| 2006/0121049 A1 | 6/2006 | Letourneur |
| 2007/0294782 A1 | 12/2007 | Abad et al. |
| 2010/0216708 A1 | 8/2010 | Jacobs et al. |
| 2010/0317539 A1 | 12/2010 | Yu |
| 2011/0256154 A1 | 10/2011 | Vincent et al. |
| 2011/0274623 A1 | 11/2011 | Jacobs |
| 2012/0148607 A1 | 6/2012 | Hultberg et al. |
| 2012/0177664 A1 | 7/2012 | Yokoseki et al. |
| 2013/0226834 A1 | 8/2013 | Gannalo, II |
| 2013/0230516 A1 | 9/2013 | Imboden et al. |
| 2013/0287748 A1 | 10/2013 | June et al. |
| 2014/0037638 A1 | 2/2014 | Holtzman et al. |
| 2014/0193427 A1 | 7/2014 | Lerner et al. |
| 2015/0038684 A1 | 2/2015 | Jensen |

(Continued)

FOREIGN PATENT DOCUMENTS

| | | |
|---|---|---|
| WO | WO 87/000195 A1 | 1/1987 |
| WO | WO 90/03430 A1 | 4/1990 |

(Continued)

OTHER PUBLICATIONS

PCT International Search Report dated Jan. 7, 2019.
Bardenheuer, et al., "Resistance to cytarabine and gemcitabine and in vitro selection of transduced cells after retroviral expression of cytidine deaminase in human hematopoietic progenitor cells," Leukemia, 19: 2281-2288 (2005).
Barnes, et al., "Methods for Growth of Cultured Cells in Serum-Free Medium," Analytical Biochemistry, 102: 255-270 (1980).
Bork, et al., "Proposed acquisition of an animal protein domain by bacteria," Proceedings of the National Academy of Science USA, 89: 8990-8994 (1992).
Nancy D. Connell, "Expression systems for use in actinomycetes and related organisms," Current Opinion in Biotechnology, 12: 446-449 (2001).

(Continued)

*Primary Examiner* — Maria Marvich
(74) *Attorney, Agent, or Firm* — Eric Dichter

(57) ABSTRACT

Fibronectin type III (FN3) domain antibodies, polynucleotides capable of encoding the FN3 domain antibodies or antigen-binding fragments, cells expressing FN3 domain antibodies or antigen-binding fragments, as well as associated vectors and detectably labeled FN3 domain antibodies or antigen-binding fragments may be used to engineer FN3 domain-targeting chimeric antigen receptors (CARs). Methods of making the FN3 domain antibodies, CARs, and engineered immune cells, and methods of using the engineered immune cells are applicable to treat diseases including cancer.

1 Claim, 39 Drawing Sheets

Specification includes a Sequence Listing.

(56) References Cited

U.S. PATENT DOCUMENTS

| | | | |
|---|---|---|---|
| 2015/0283178 A1* | 10/2015 | June | A61K 35/17 424/85.2 |
| 2016/0053017 A1 | 2/2016 | Orentas et al. | |
| 2016/0244521 A1 | 8/2016 | White et al. | |
| 2016/0362472 A1* | 12/2016 | Bitter | C07K 16/2803 |
| 2016/0376365 A1 | 12/2016 | Gurney et al. | |
| 2017/0051071 A1 | 2/2017 | Reuger et al. | |
| 2019/0175651 A1* | 6/2019 | Lee | C12N 15/90 |

FOREIGN PATENT DOCUMENTS

| | | |
|---|---|---|
| WO | WO 2007/059782 A1 | 5/2007 |
| WO | WO 2010/066872 | 6/2010 |
| WO | WO 2012/129514 A1 | 9/2012 |
| WO | WO2012129514 A1 | 9/2012 |
| WO | WO 2013/176915 A1 | 11/2013 |
| WO | WO2013/176916 A1 | 11/2013 |
| WO | WO 2014/039523 A1 | 3/2014 |
| WO | WO 2014/130635 A1 | 8/2014 |
| WO | WO 2014/184143 A1 | 11/2014 |
| WO | WO 2014/184741 A1 | 11/2014 |
| WO | WO 2014/184744 A1 | 11/2014 |
| WO | WO 2014/191128 A1 | 12/2014 |
| WO | WO 2017/002919 A1 | 1/2017 |
| WO | WO 2017/049296 A1 | 3/2017 |
| WO | WO 2017/089447 A1 | 6/2017 |
| WO | WO 2017/118307 A1 | 7/2017 |

OTHER PUBLICATIONS

Chothia, et al., "Canonical Structures for the Hypervarialbe Regions of Immunoglobulins," Journal of Molecular Biology, 196: 901-917 (1987).
Chothia, et al., "Conformations of immunoglobulin hypervariable regions," Nature, 342: 877-883 (1989).
Ham, et al., "Media and Growth Requirements," Methods of Enzymology, 58: 44-93 (1979).
Holt, et al., "Domain antibodies: proteins for therapy," Trends in Biotechnology, 21(11): 484-490 (2003).
Jacobs, et al., "Design of novel FN3 domains with high stability by a consensus sequence approach," Protein Engineering, Design & Selection, 25(3): 107-117 (2012).
Kushman, et al., "Expression of human glutathione S-transferase P1 confers resistance to benzo[a]pyrene or benzo[a]pyrene-7,8-dihydrodiol mutagenesis, macromolecular alkylation and formation of stable N2-Gua-BPDE adducts in stably transfected V79MZ cells co-expressing hCYP1A1," Cardinogenesis, 28(1): 207-214 (2007).
Luckow, et al., "Trends in the Development of Baculovirus Expression Vectors," Bio/Technology, 6: 47-55 (1988).
Sawas C. Makrides, "Strategies for Achieving High-Level Expression of Genes in *Escherichia coli*," Microbiological Reviews, 60(3): 512-538 (1996).

MacCallum, et al., "Antibody-antigen Interactions: Contact Analysis and Binding Site Topography," Journal of Molecular Biology, 262: 732-745 (1996).
Mayfield, et al., "Expression and assembly of a fully active antibody in algae," Proceedings of the National Academy of Science, 100(2): 438-442 (2003).
Martin, et al., "Structural Families in Loops of Homologous Proteins: Automatic Classification, Modelling and Application to Antibodies," Journal of Molecular Biology, 263: 800-815 (1996).
Meinke, et al., "Cellulose-Binding Polypeptides from *Cellulomonas fimi*: Endoglucanase D (CenD), a Family A β-1,4-Glucanase," Journal of Bacteriology, 175 (7): 1910-1918 (1993).
Myers, et al., "Optimal alignments in linear space," CABIOS, 4 (1): 11-17 (1988).
Needleman, et al., "A General Method Applicable to the Search for Similarities in the Amino Acid Sequence of Two Proteins," Journal of Molecular Biology, 48: 443-453 (1970).
Nivens, et al., "Engineered resistance to camptothecin and antifolates by retroviral coexpression of tyrosyl DNA phosphodiesterase-I and thymidylate synthase," Cancer Chemother. Pharmacol., 53: 107-115 (2004).
Patel, et al., "Impact of chimeric immune receptor extracellular protein domains on T cell function," Gene Therapy, 6: 412-419 (1999).
Revets, et al., "Nanobodies as novel agents for cancer therapy," Expert Opinion on Biological Therapy, 5 (10): 111-124 (2005).
Sinclair, et al., "Synonymous codon usage bias and the expression of human glucoce4rebrosidase in the methylotrophic yeast, *Pichia pastoris*" Protein Expression and Purification, 26: 96-105 (2002).
Sugimoto, et al., "Drug-selected co-expression of P-glycoprotein and gp91 in vivo from an $MDR_i$-bicistronic retrovirus vector Ha-MDR-IRES-gp91," The Journal of Gene Medicine, 5: 366-376 (2003).
Takebe, et al., "Generation of Dual Resistance to 4-Hydroperoxycyclophosphamide and Methotrexate by Retroviral Transfer of the Human Aldehyde Dehydrogenase Class 1 Gene and a Mutated Dihydrofolate Reductase Gene," Molecular Therapy, 3(1): 88-96 (2001).
Uniprot Accession No. E1F8D8 Nov. 30, 2010.
Uniprot Accession No. D8SB13 Oct. 5, 2010.
Uniprot Accession No. A0A168DVB3 Jul. 6, 2016.
Uniprot Accession No. A0A1V6DWF0 Jun. 7, 2017.
Vanterpool, et al., "A material-based platform to modulate fibronectin activity and focal adhesion assembly," BioResearch open access, 3(6): 286-296 (2014).
Watanabe, et al., "Gene Cloning of Chitinase A1 from *Bacillus circulans* WL-12 Revealed Its Evolutionary Relationship to *Serratia* Chitinase and to the Type III Homology Units of Fibronectin," The Journal of Biological Chemistry, 265 (26): 15659-15665 (1990).
Zielske, et al., "In vivo selection of MGMT (P140K) lentivirus-transduced human NOD/SCID repopulating cells without pretransplant irradiation conditioning," Journal of Clinical Investigations, 112(10): 1561-1570 (2003).

\* cited by examiner

Figure 2A (EP control)
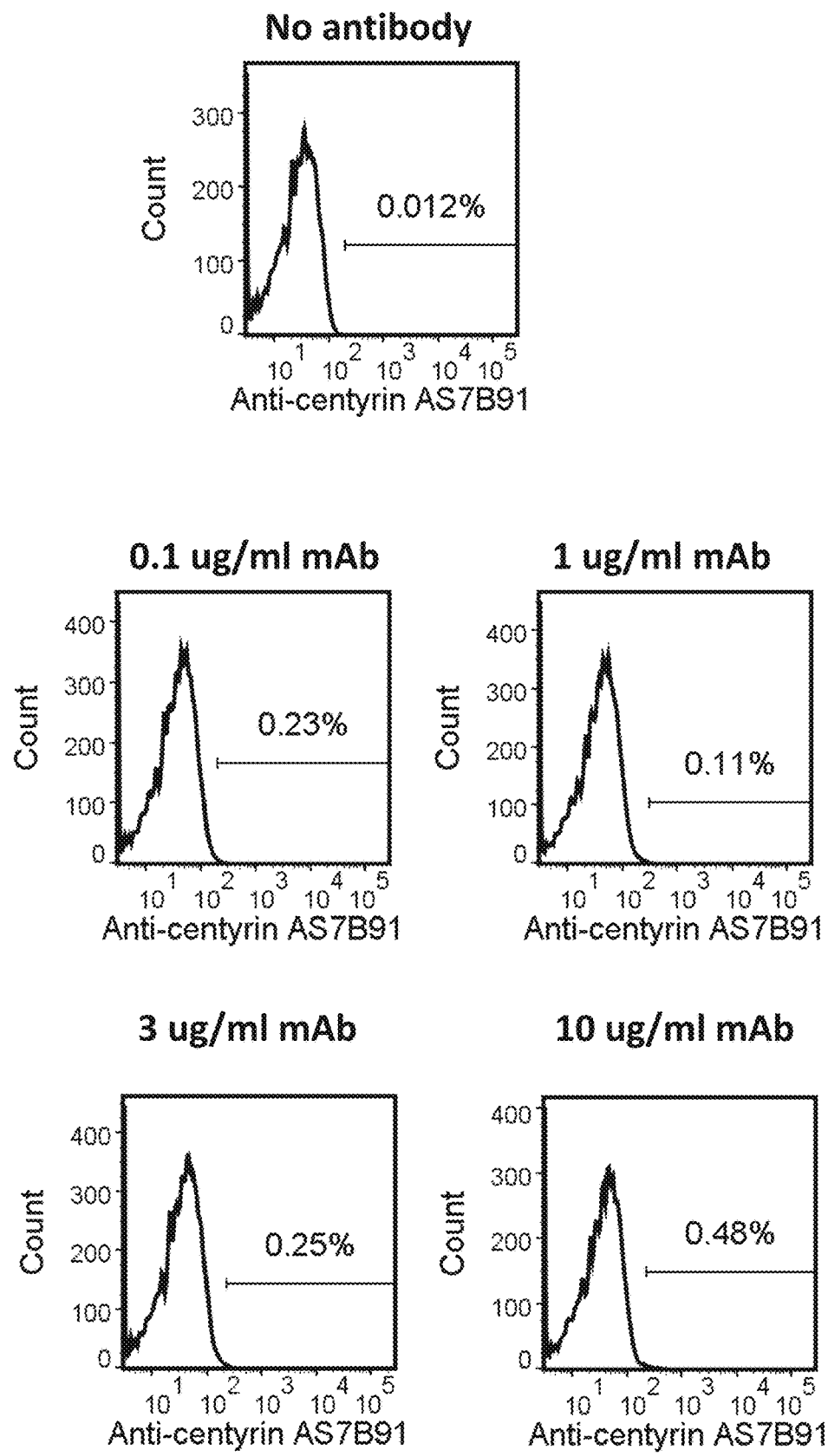

Figure 2B (AO8)
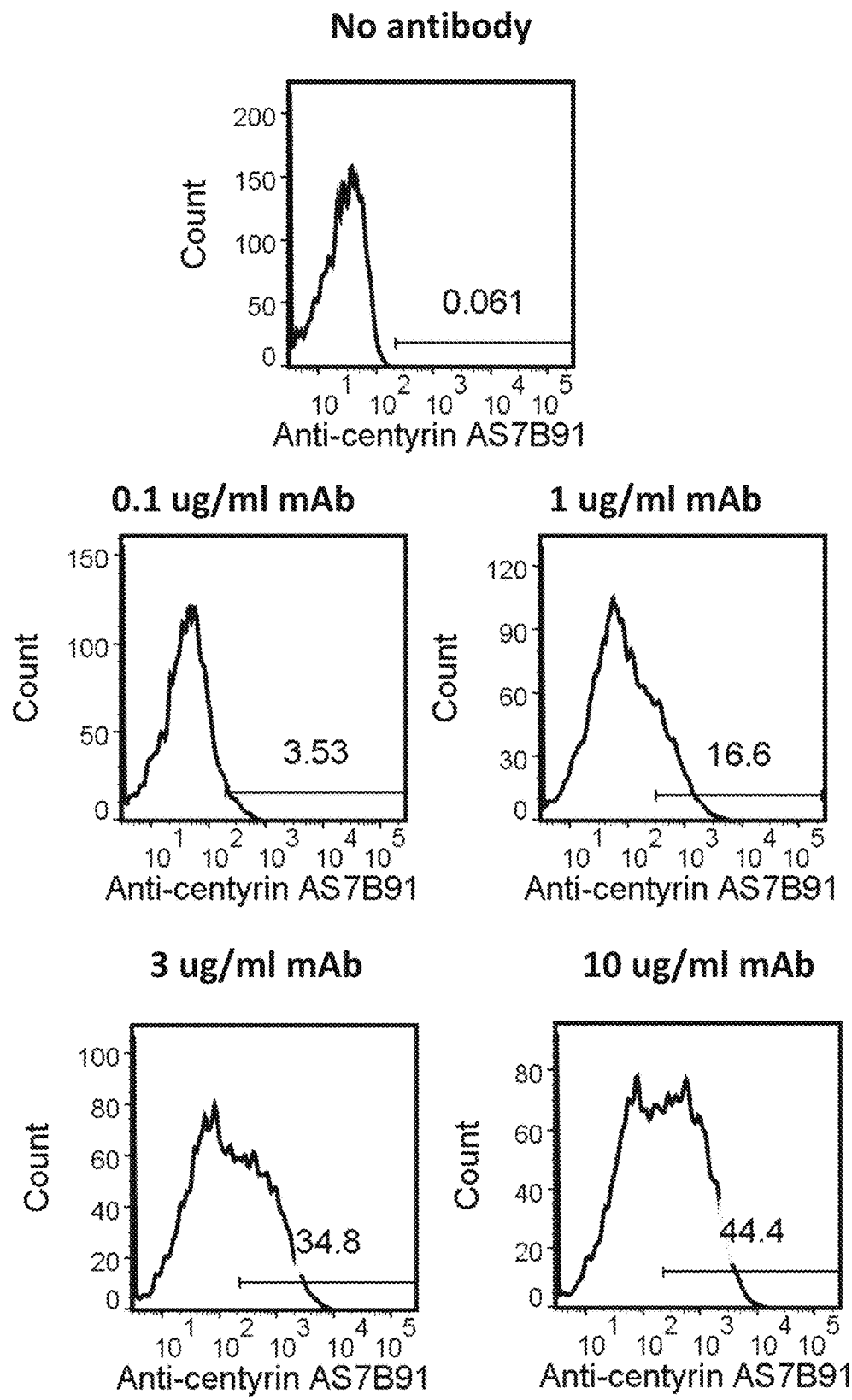

Figure 2C (A12)
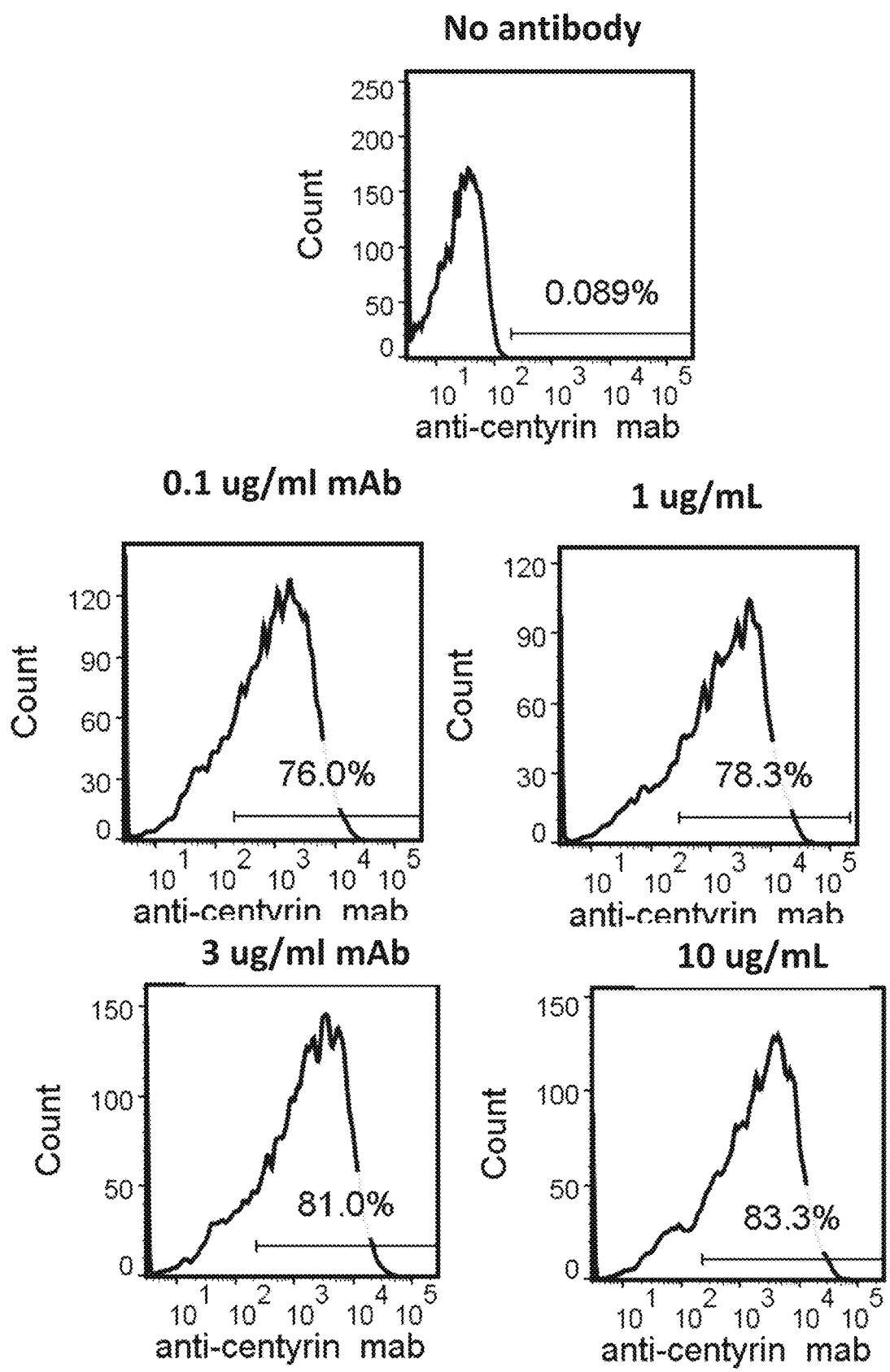

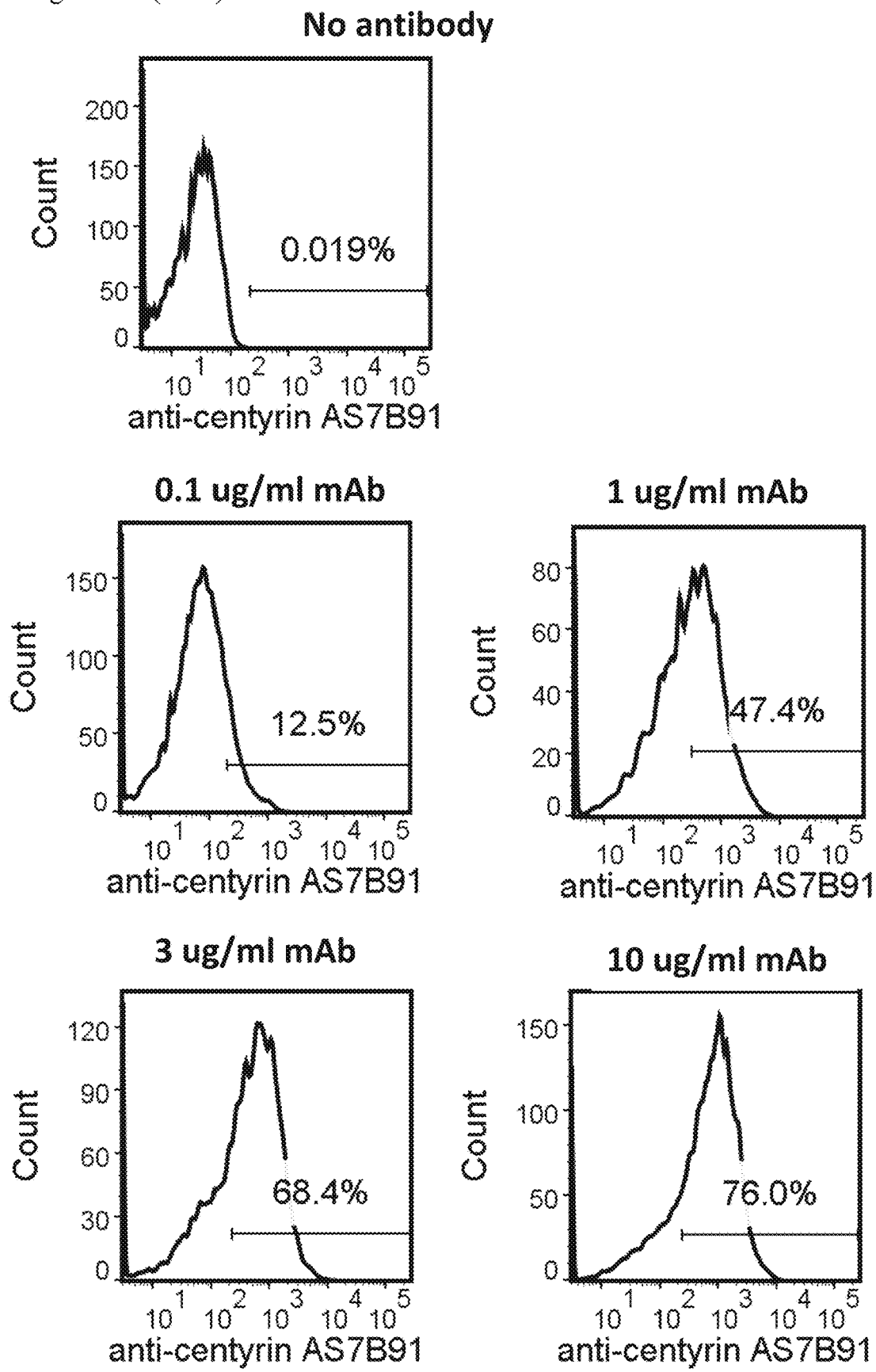
Figure 2D (BO3)

Figure 2E (CO8)
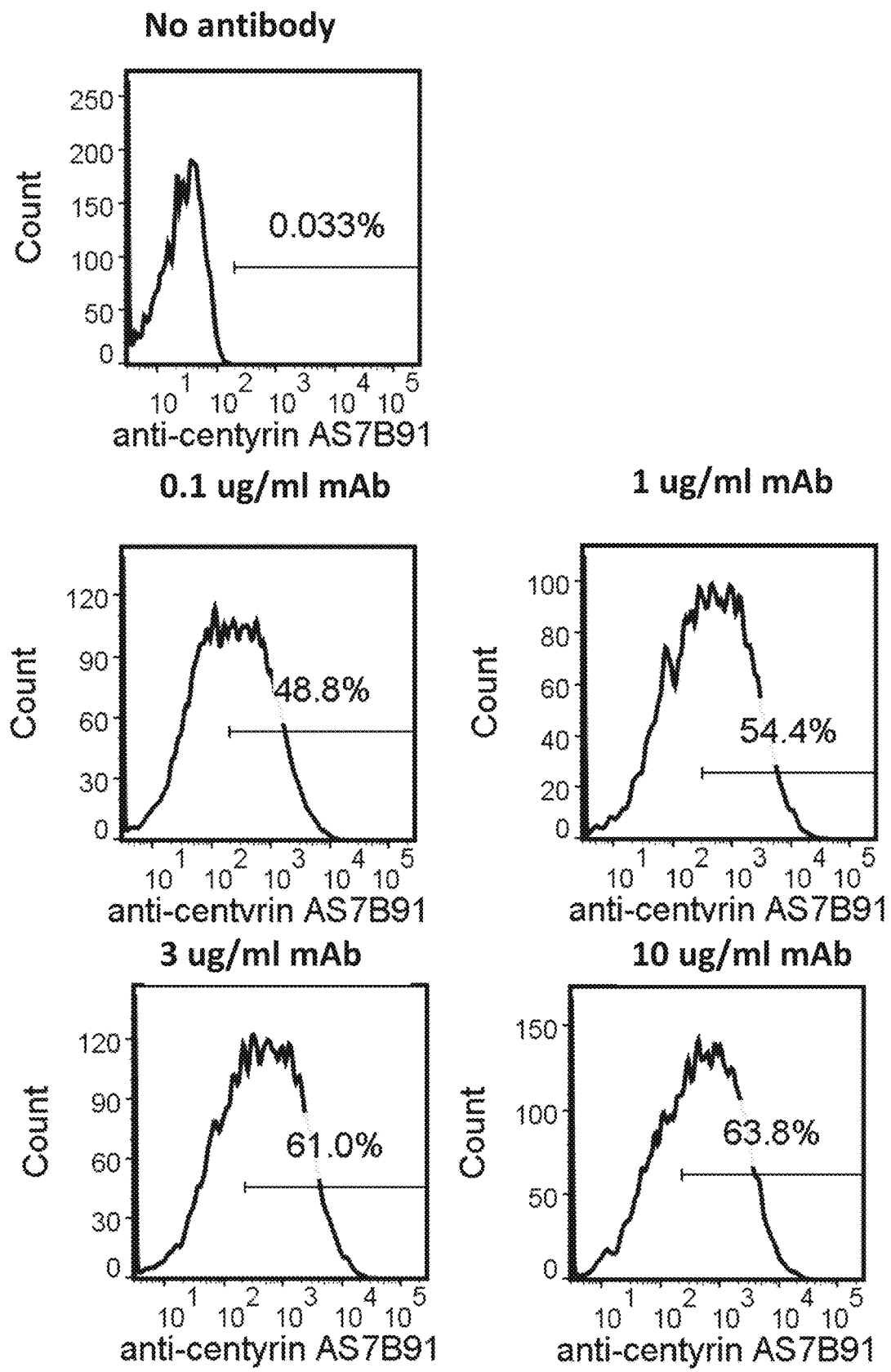

Figure 2F (DO8)
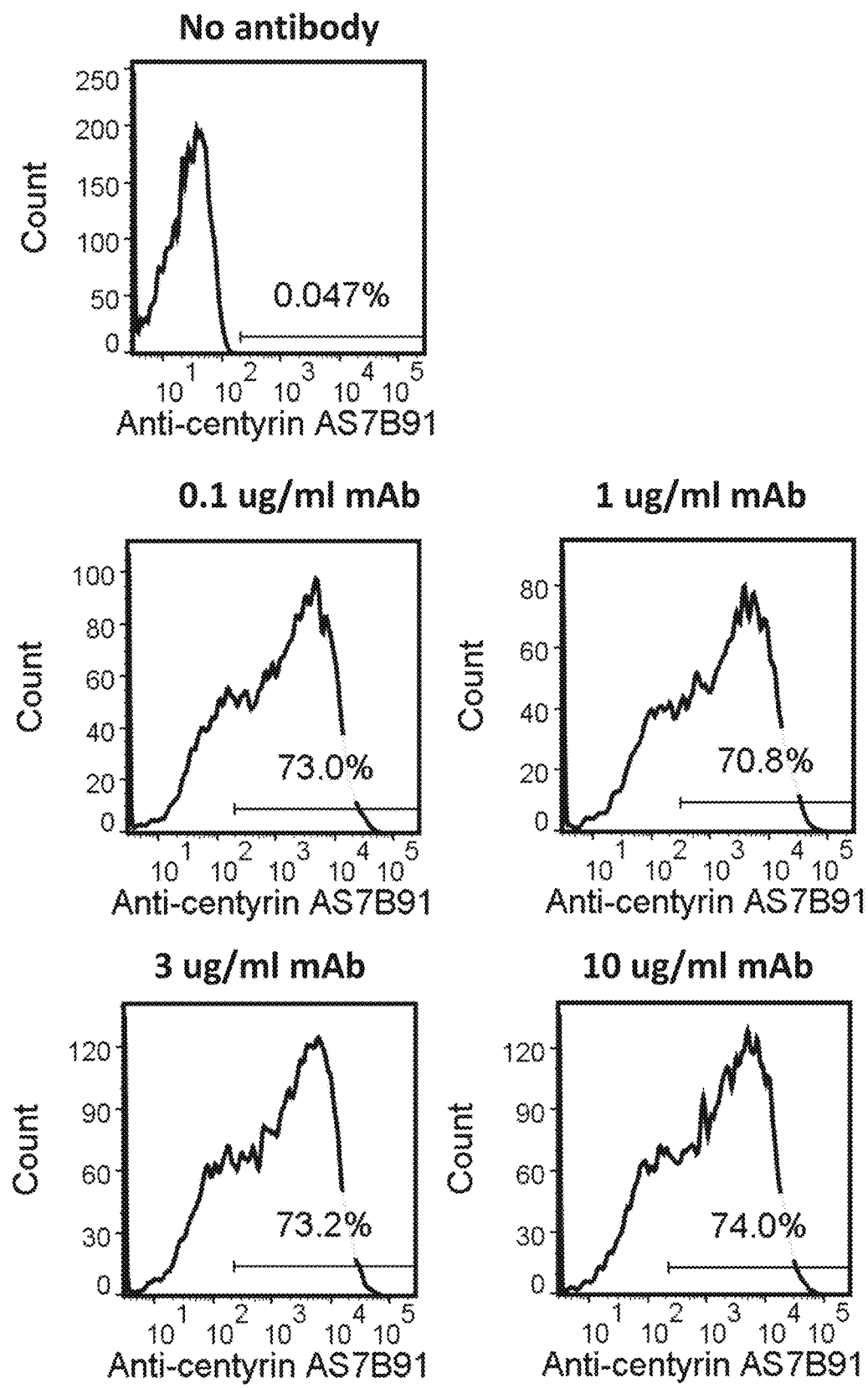

Figure 2G (D10)
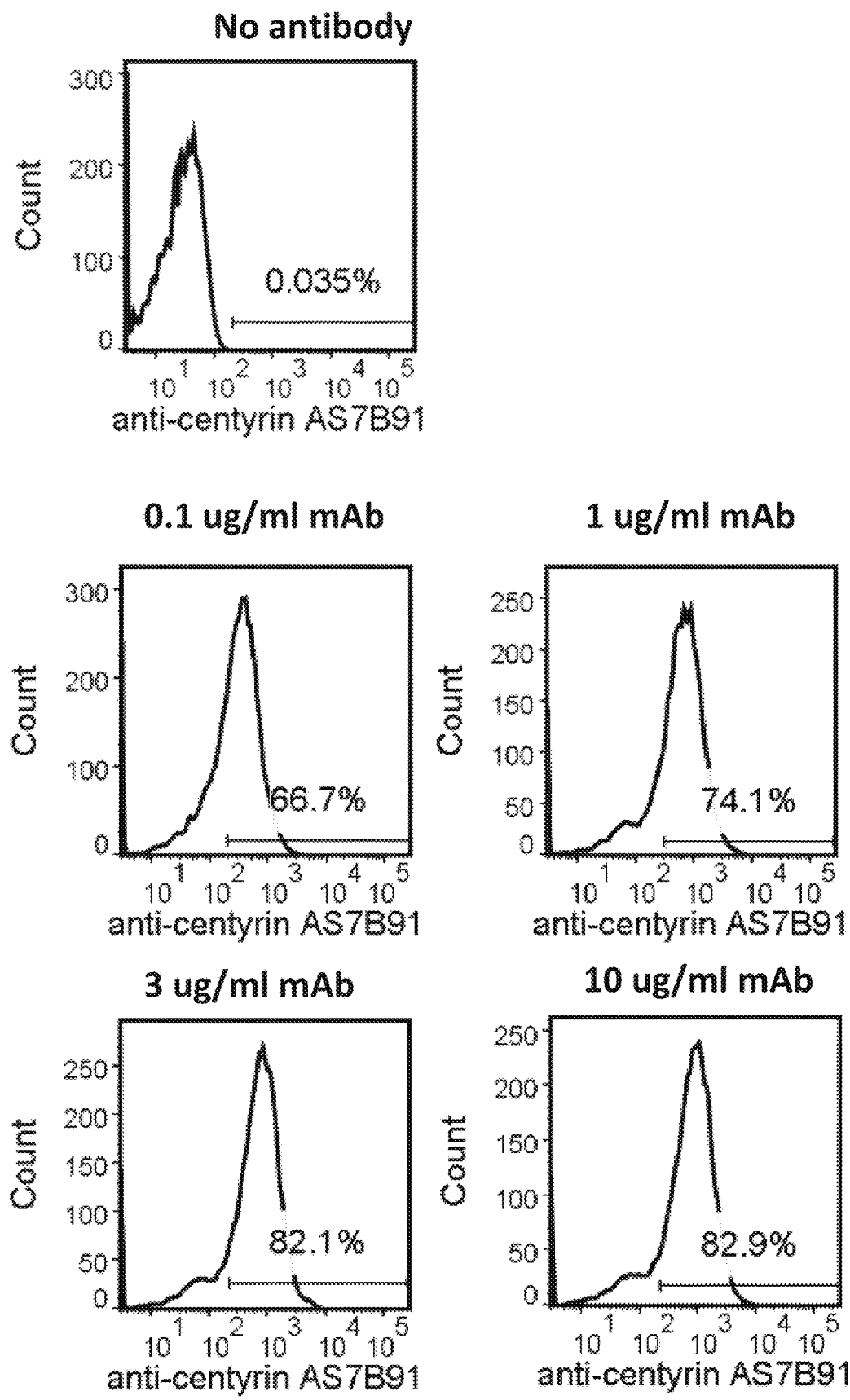

Figure 2H (EO2)
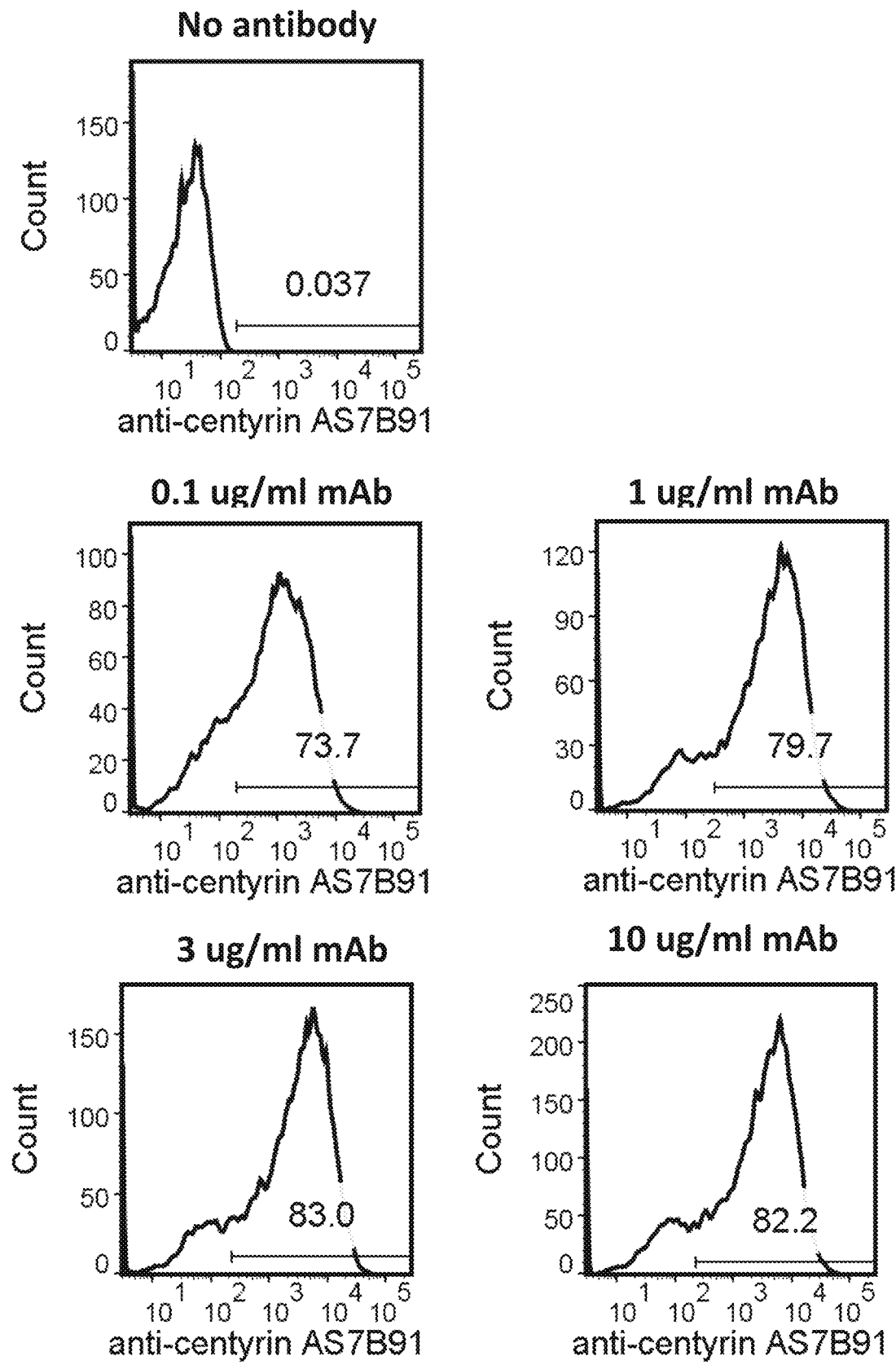

Figure 2I (EO9)
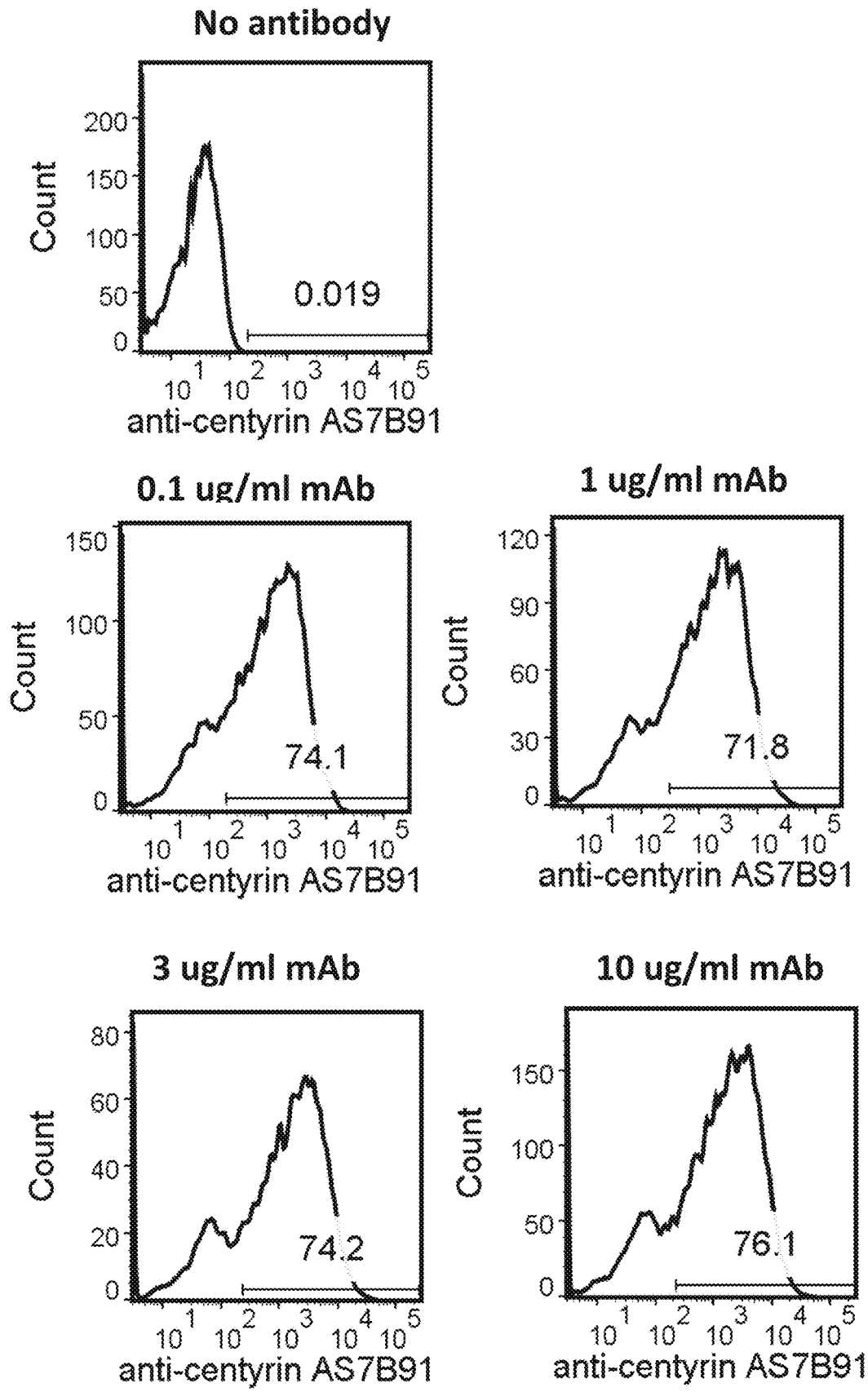

Figure 2J (FO1)
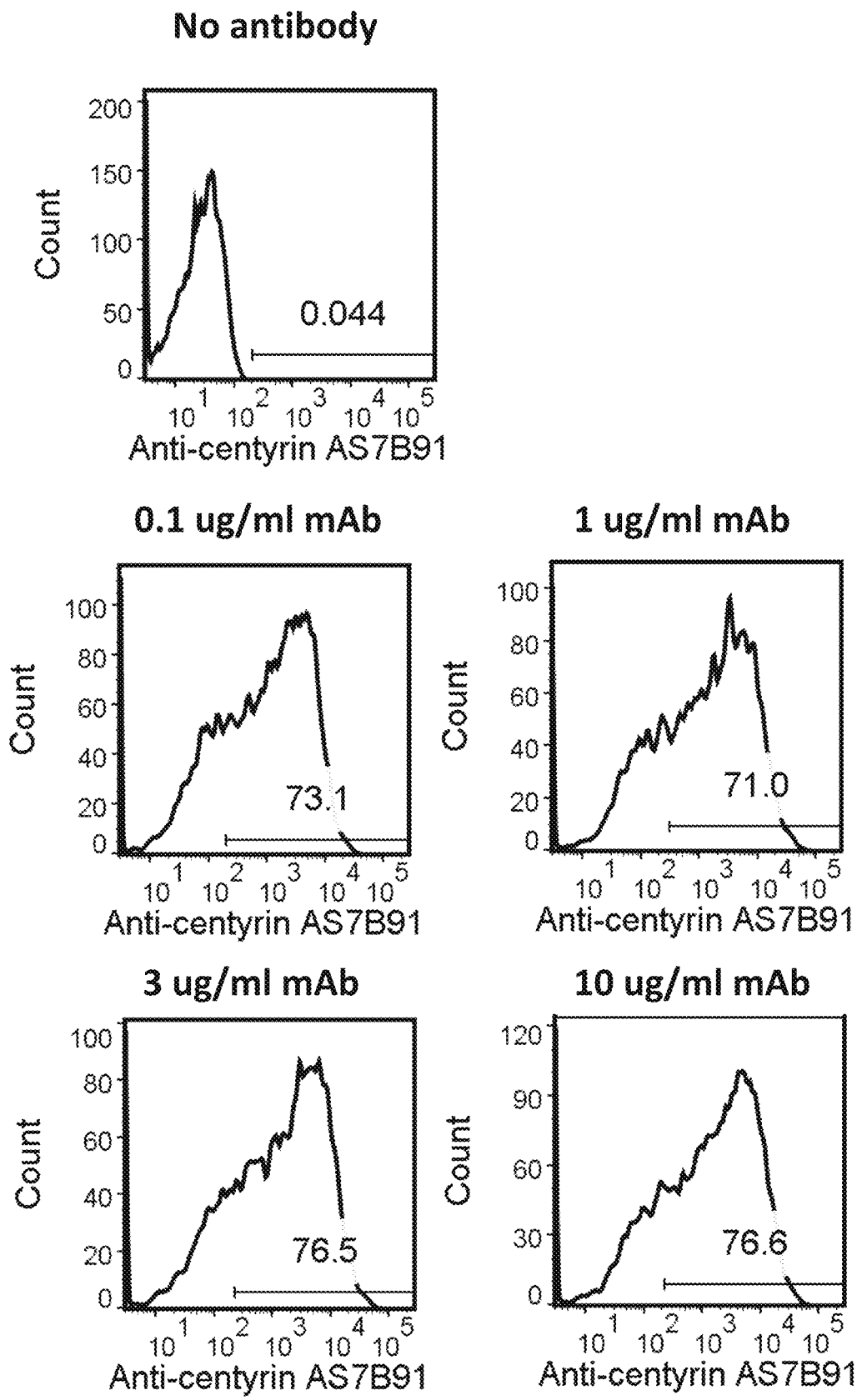

Figure 2K (F11)
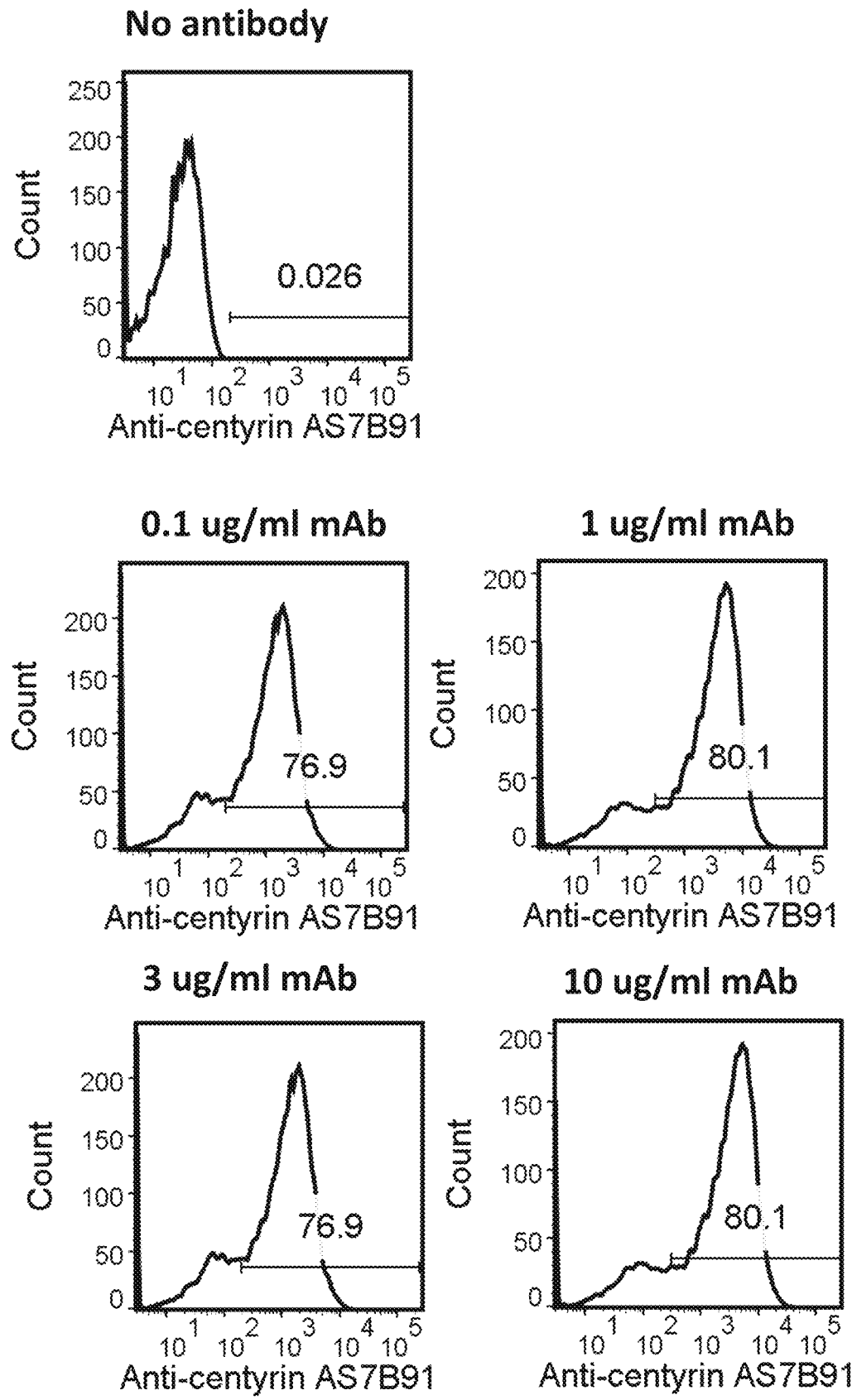

Figure 2L (G10)
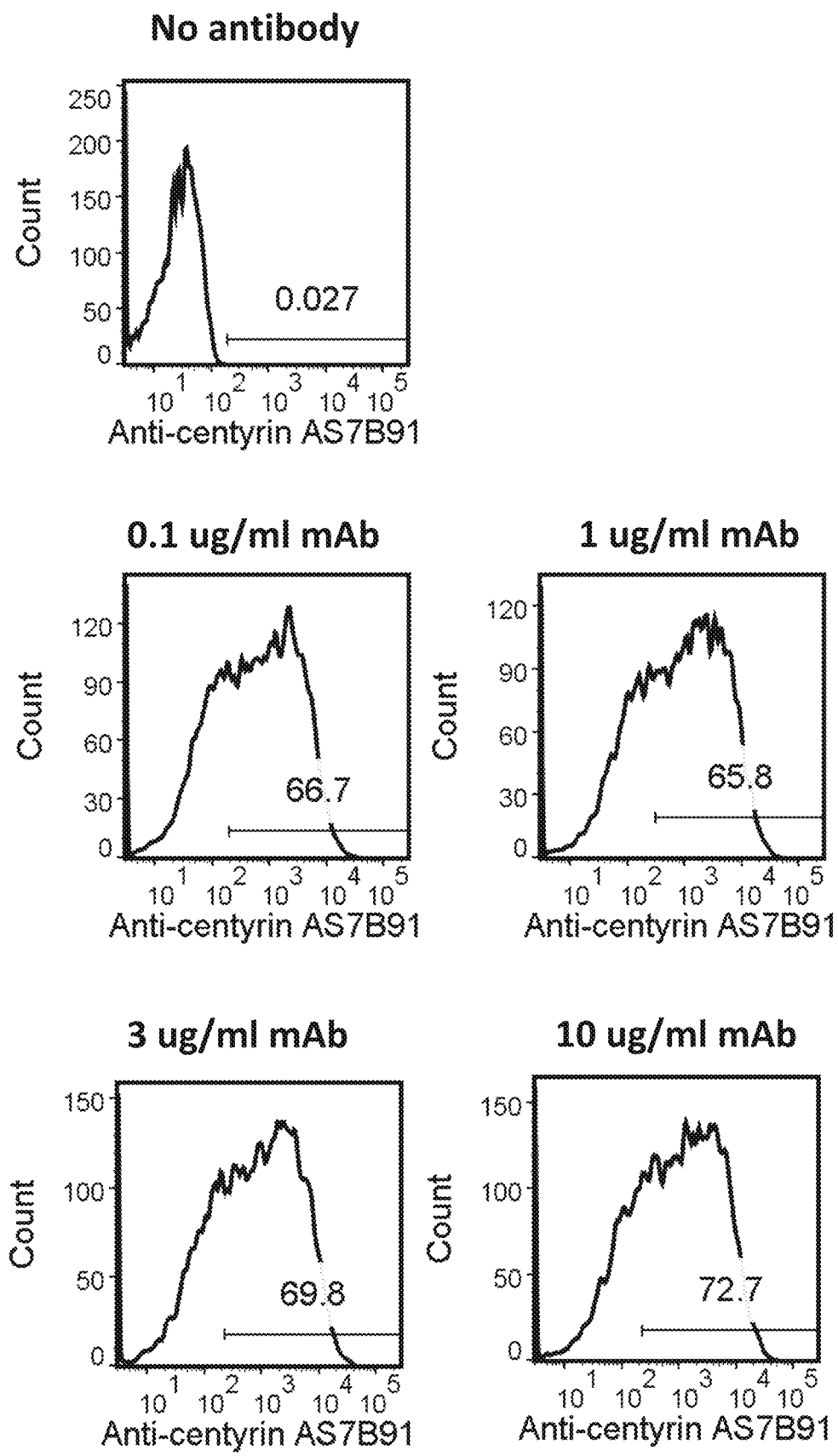

Figure 2M (DO8-89)
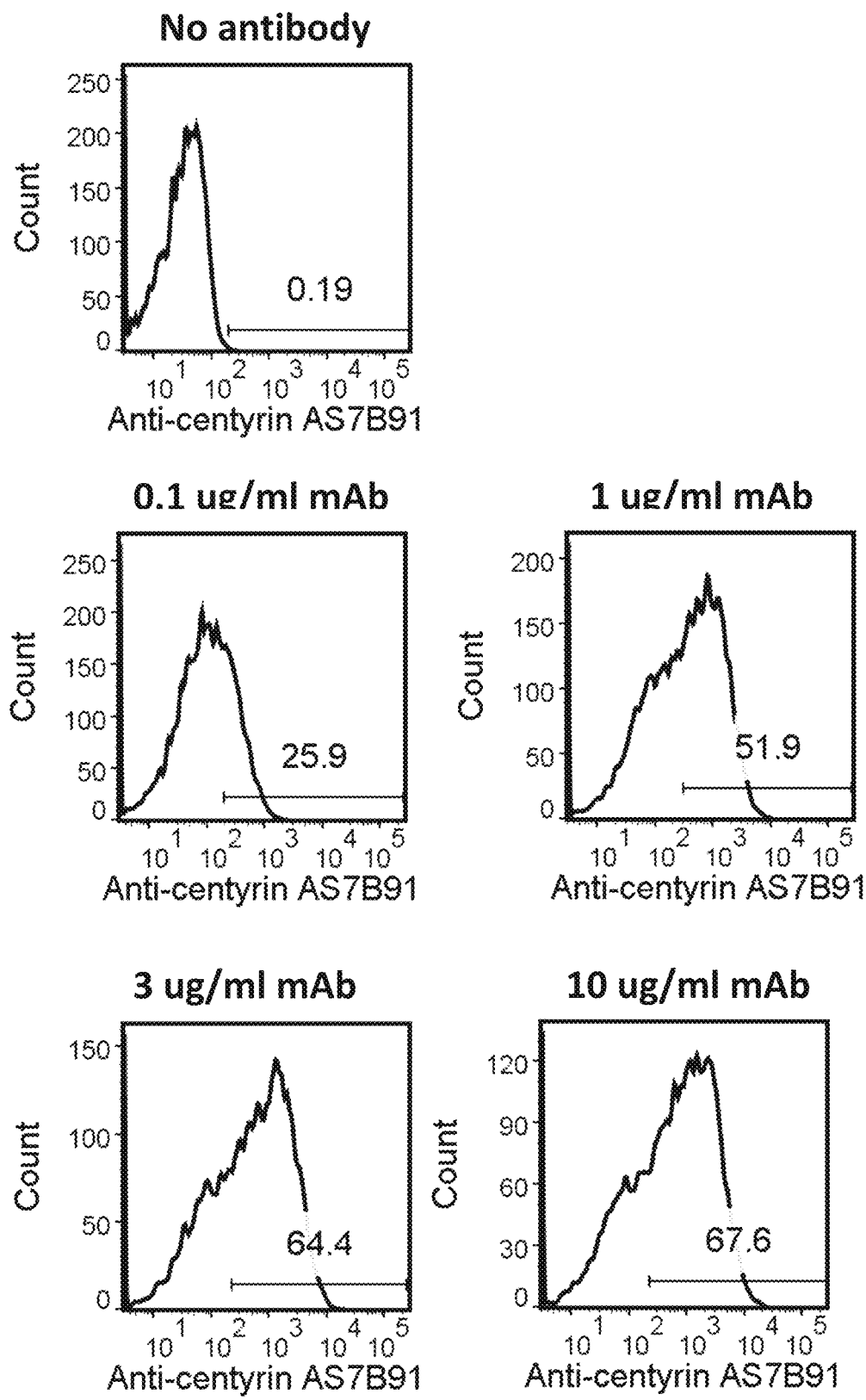

Figure 5 con't
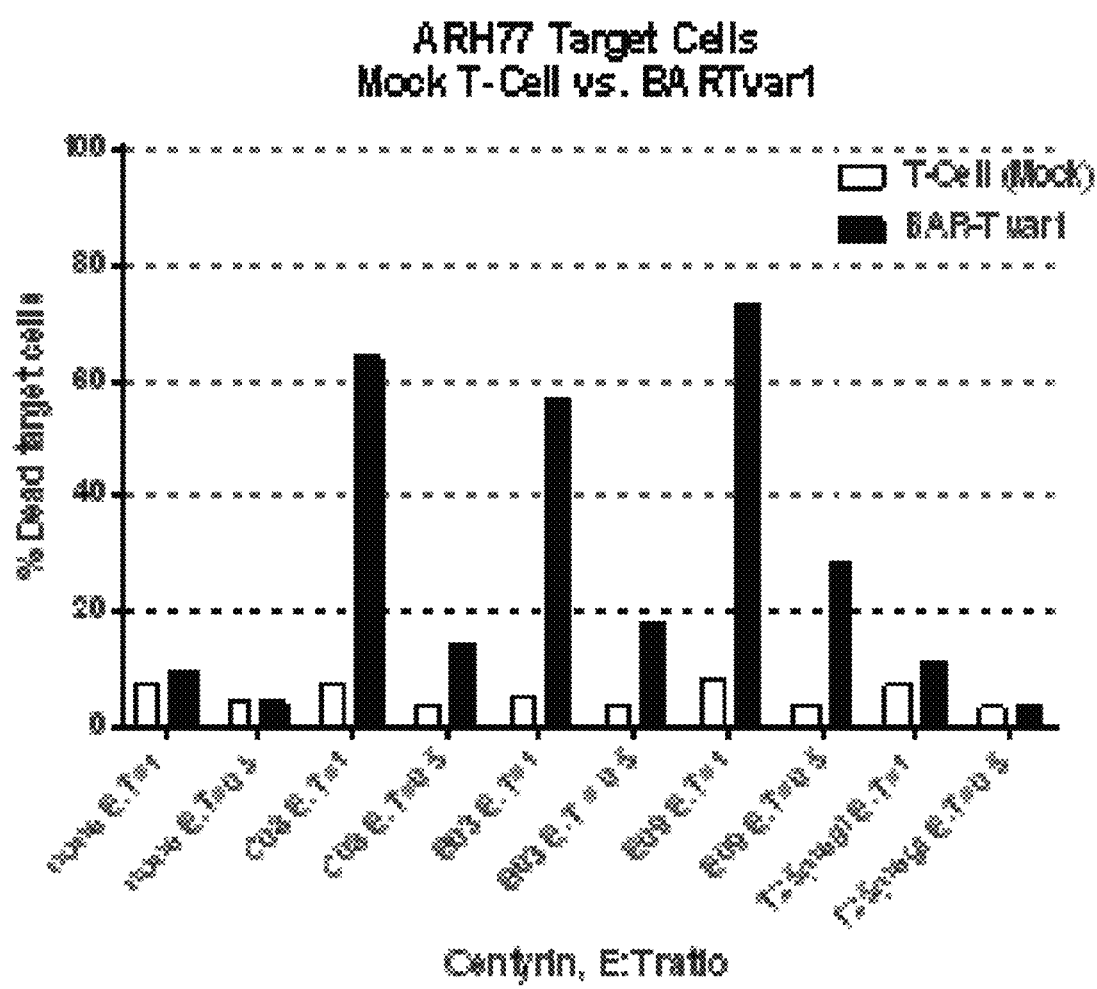

Figure 5 con't
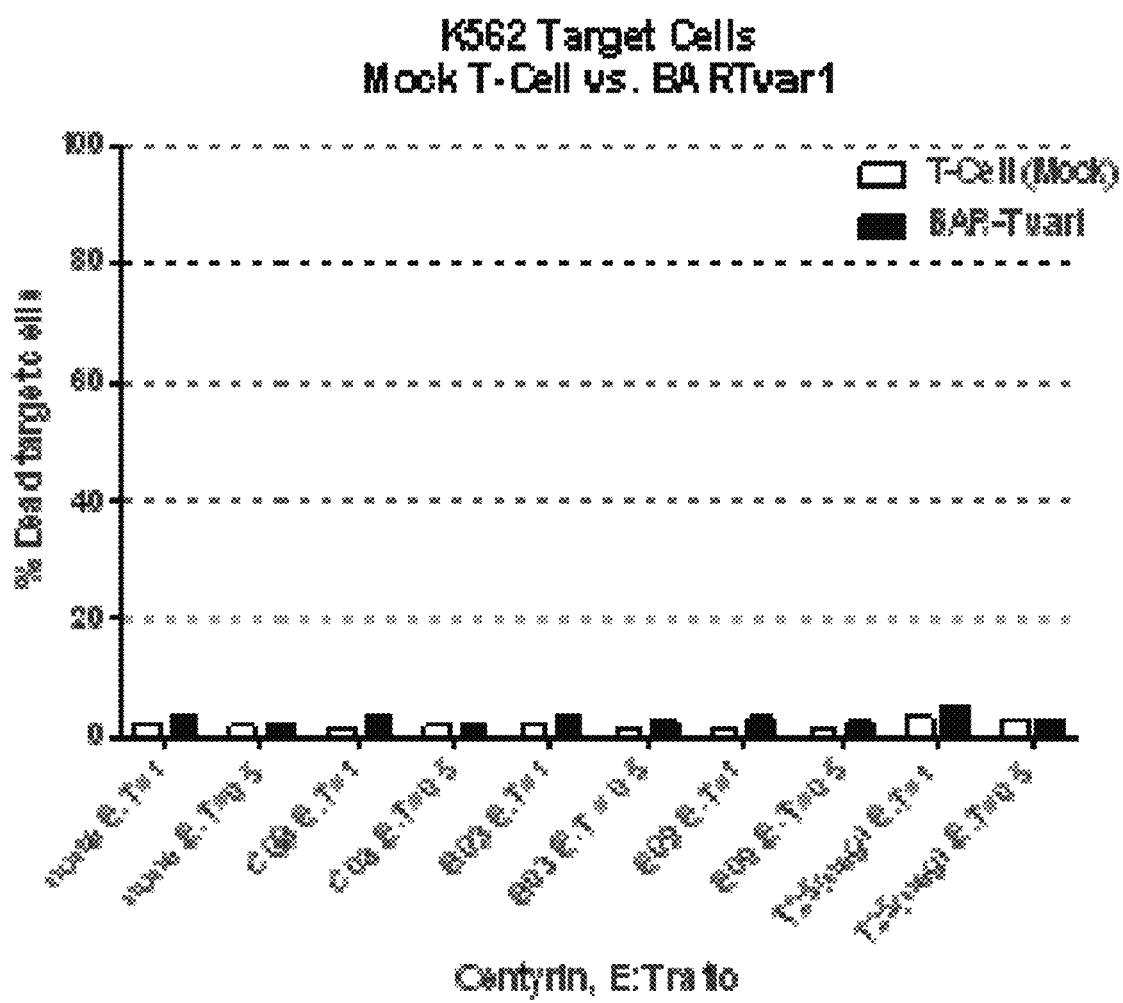

Figure 5 con't
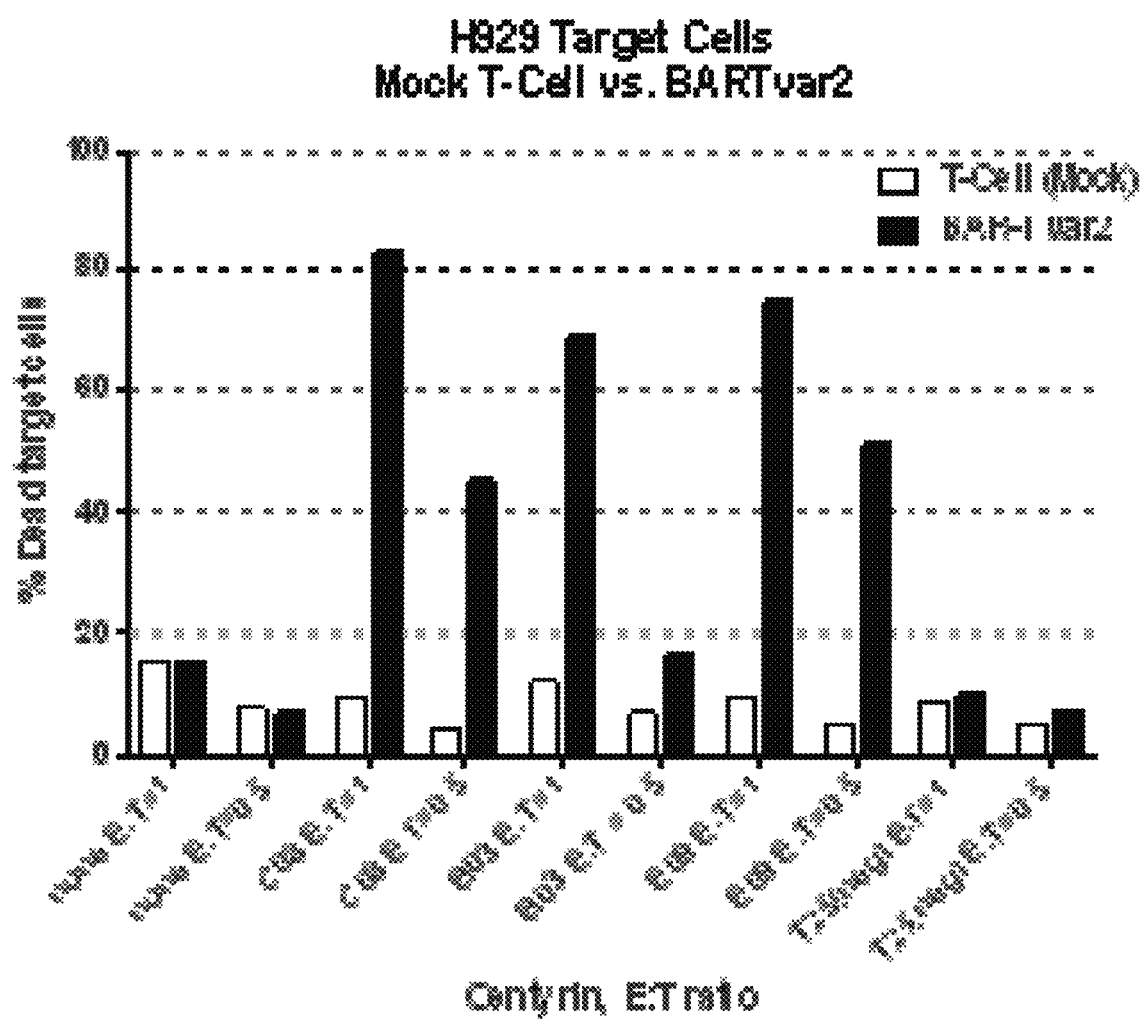

Figure 5 con't
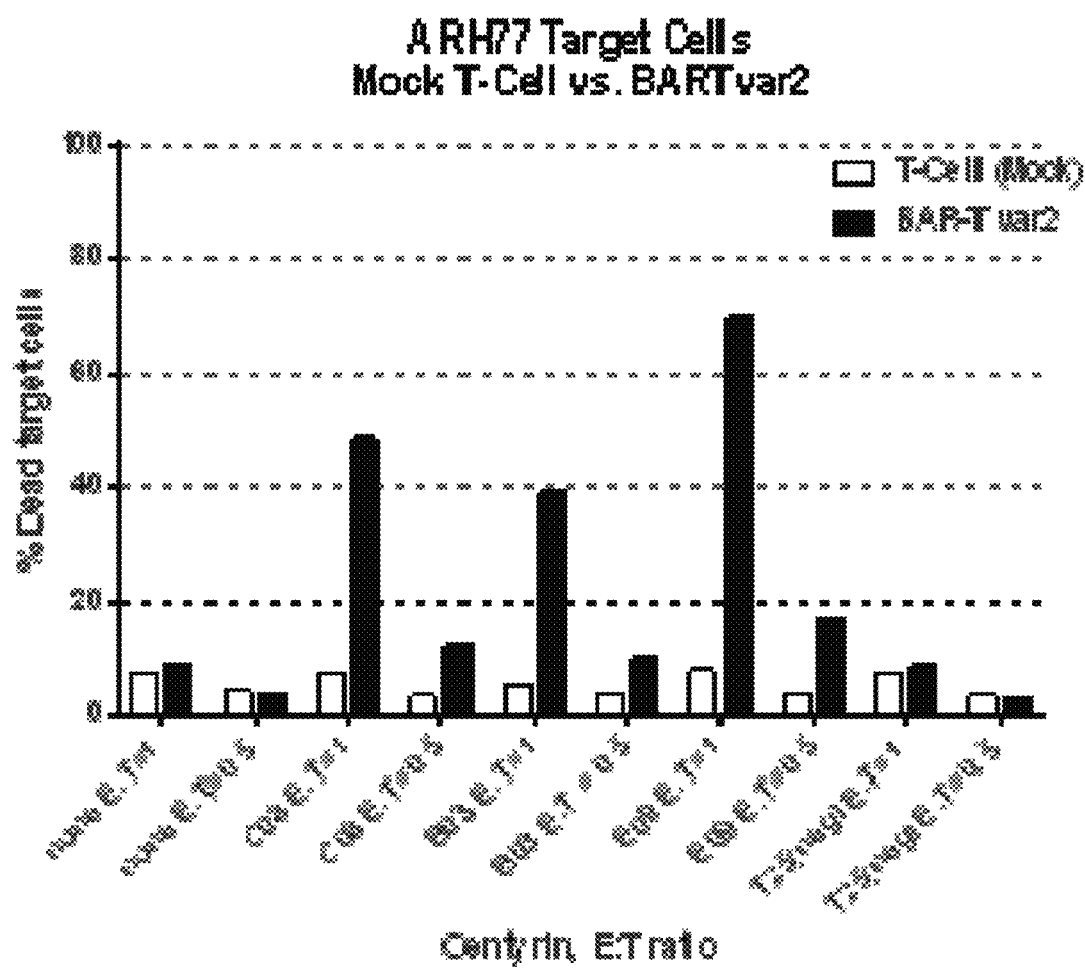

Figure 5 con't
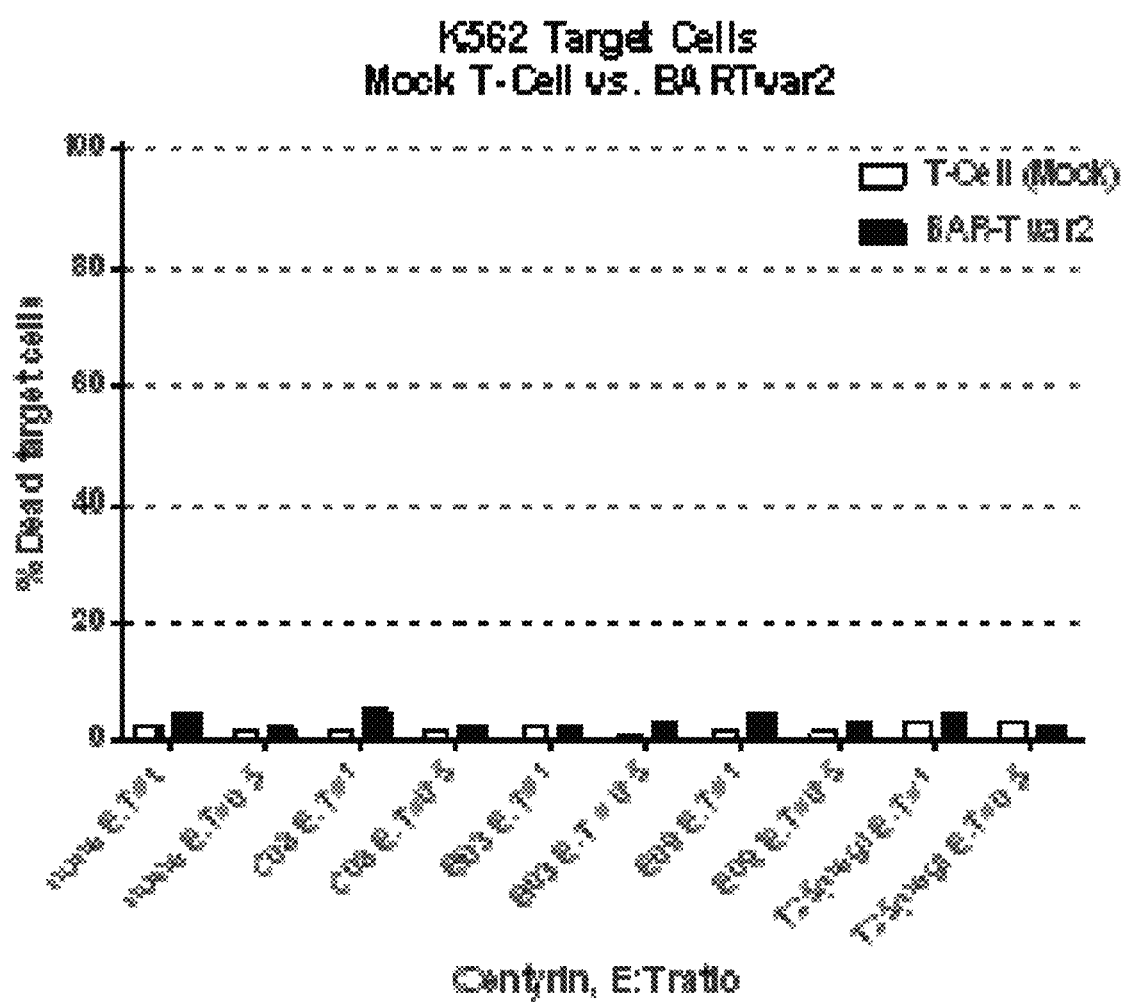

A. No CAR
B. AS7B16 L2H scFv CAR
C. AS7B16 H2L scFv CAR
D. AS7B91 H2L scFv CAR

Figure 7
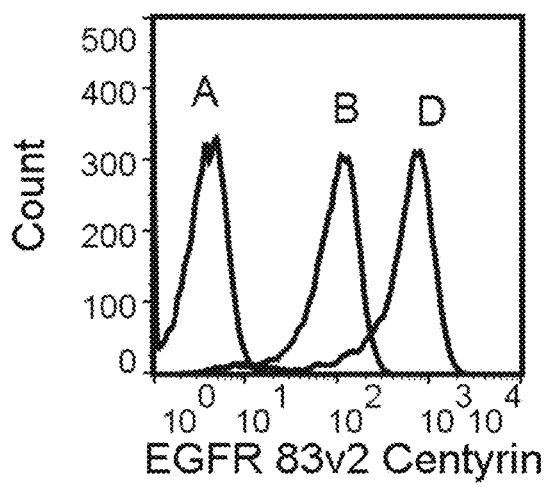
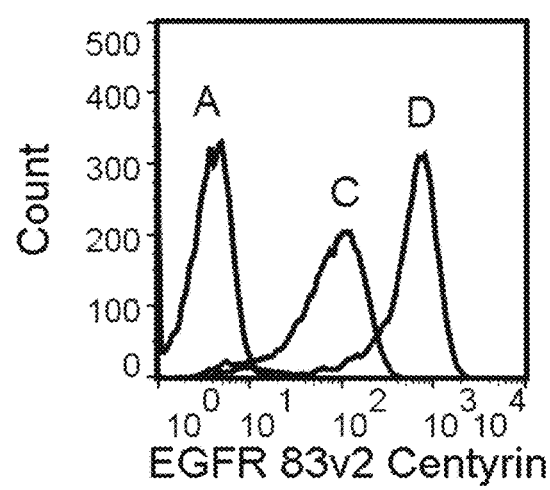
A. No CAR
B. AS7B16 L2H scFv CAR
C. AS7B16 H2L scFv CAR
D. AS7B91 H2L scFv CAR

A. No CAR
B. AS7B82 L2H scFv CAR
C. AS7B82 H2L scFv CAR
D. AS7B91 H2L scFv CAR

A. No CAR
B. AS7B82 L2H scFv CAR
C. AS7B82 H2L scFv CAR
D. AS7B91 H2L scFv CAR

Figure 11A
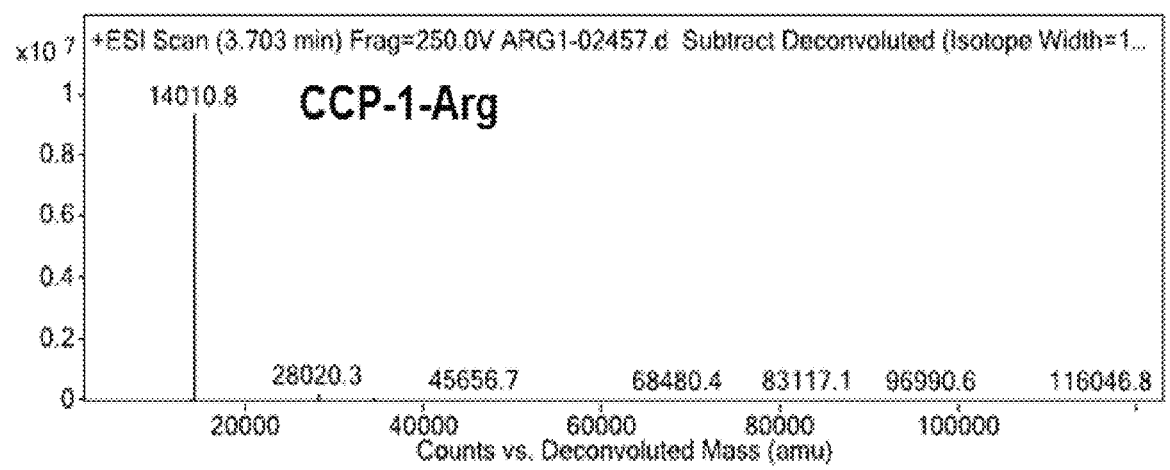
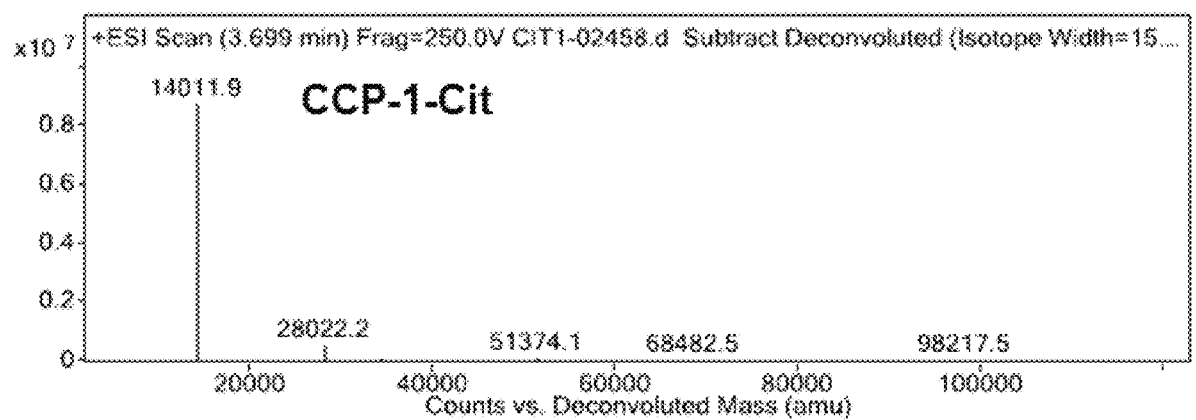

Figure 11B
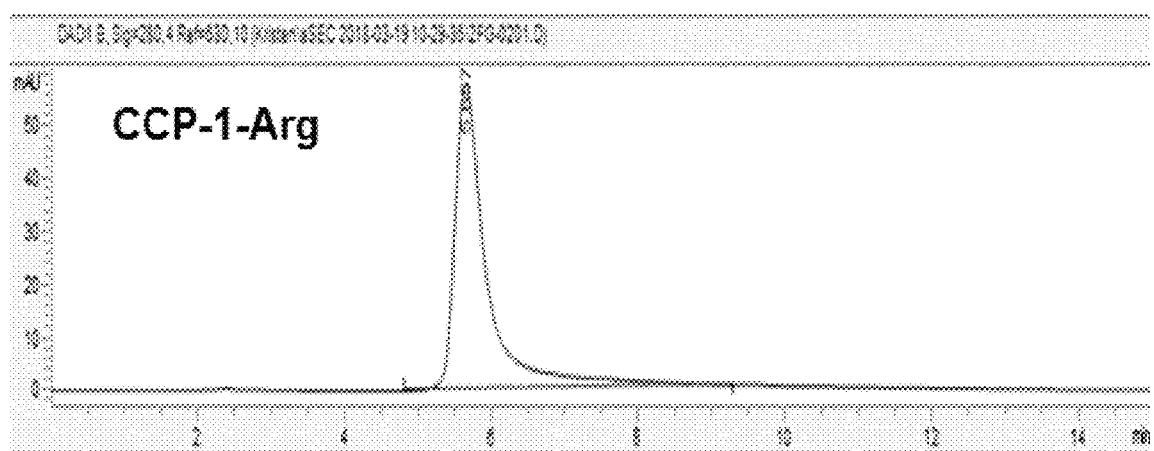
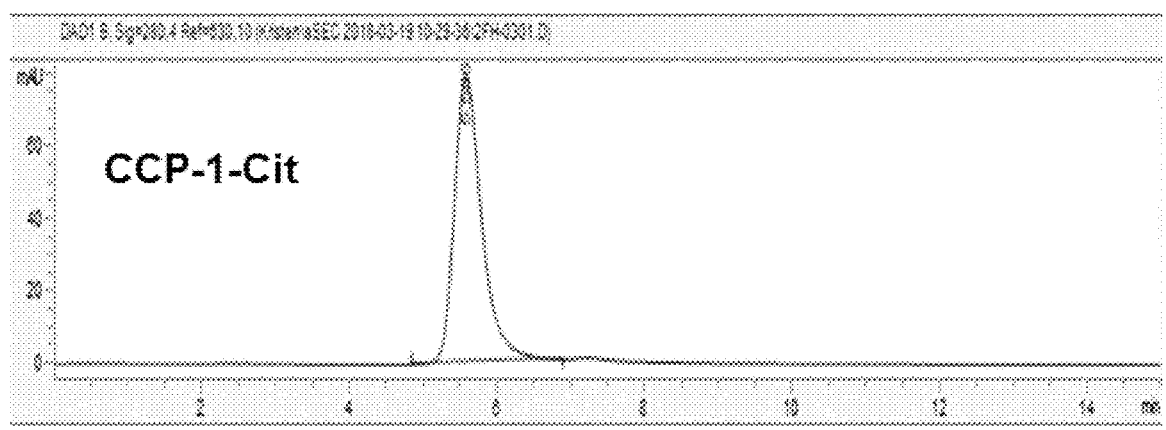

ANTIGEN BINDING REGIONS AGAINST FIBRONECTIN TYPE III DOMAINS AND METHODS OF USING THE SAME

CROSS-REFERENCE TO RELATED APPLICATIONS

This application claims the benefit of U.S. Provisional Application Ser. No. 62/533,341, filed 17 Jul. 2017 and U.S. Provisional Application Ser. No. 62/625,576, filed 2 Feb. 2018. The entire content of the aforementioned applications is incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 29, 2018, is named JBI5032USNPSL.txt and is 87,129 bytes in size.

TECHNICAL FIELD

The present invention relates to antibodies that bind specifically to fibronectin type III domains (FN3 domains) and methods of producing and using the described antibodies.

BACKGROUND

Fibronectin based scaffolds are a family of proteins capable of evolving to bind any compound of interest. These proteins, which generally make use of a scaffold derived from a fibronectin type III (FN3) or FN3-like domain, function in a manner characteristic of natural or engineered antibodies (that is, polyclonal, monoclonal, or single-chain antibodies) and, in addition, possess structural advantages. Specifically, the structure of these antibody mimics has been designed for optimal folding, stability, and solubility, even under conditions that normally lead to the loss of structure and function in antibodies. An example of fibronectin-based scaffold proteins is the Centyrin™ (Jacobs et al., Protein Engineering, Design, and Selection, 25:107-117, 2012; US2010/0216708).

Fibronectin type III (Fn3) domains comprise, in order from N-terminus to C-terminus, a beta or beta-like strand, A; a loop, AB; a beta or beta-like strand, B; a loop, BC; a beta or beta-like strand C; a loop CD; a beta or beta-like strand D; a loop DE; a beta or beta-like strand, E; a loop, EF; a beta or beta-like strand F; a loop FG; and a beta or beta-like strand G. Any or all of loops AB, BC, CD, DE, EF and FG may participate in target binding. The BC, DE, and FG loops are both structurally and functionally analogous to the complementarity determining regions (CDRs) from immunoglobulins.

Given the small size, lack of disulfide bonds, high stability, and ability to be expressed in prokaryotic hosts, the FN3 domains have gained biopharmaceutical interest. FN3 domains can be easily conjugated to drugs/toxins, penetrate efficiently into tissues and are readily formatted into multi-specific binders and fusion proteins, including chimeric antigen receptors (CARs).

Despite the versatility, there is presently no antibody available which specifically binds to FN3 domains for detection, assays, or biopharmaceutical purposes.

SUMMARY OF THE PRESENT INVENTION

The present invention includes antibodies and antigen-binding fragments that bind to a non-randomized region of a fibronectin type III (FN3) domain. Also described are related polynucleotides capable of encoding the provided FN3 domain antibodies and antigen-binding fragments, cells expressing the provided antibodies and antigen-binding fragments, as well as associated vectors and detectably labeled FN3 domain antibodies and antigen-binding fragments. The antibody or antigen binding fragment thereof does not selectively bind to a randomized region of the FN3 domain as measured by ELISA under the conditions shown in Example 3.

In addition, methods of using the provided FN3 domain antibodies and antigen-binding fragments are described. The described FN3 domain antibodies and antigen-binding fragments can be used to detect the T-cell surface expression of chimeric antigen receptors (CARs) comprising FN3 domains. In another embodiment, the described FN3 domain antibodies and antigen-binding fragments can be used to activate T-cell expressing CARs comprising FN3 domains. In yet another embodiment, the described FN3 domain antibodies or antigen binding fragments can be used to generate CARs comprising the described antigen binding fragments.

In some embodiments, the present invention comprises isolated antibodies and antigen-binding fragments wherein the antibody or antigen binding fragment specifically binds to a non-randomized region of an FN3 domain. These FN3 domain antibodies, or antigen-binding fragments thereof may detect the T-cell surface expression of chimeric antigen receptors (CARs) comprising FN3 domains. In some embodiments, the FN3 domain antibodies, or antigen-binding fragments activate T-cell expressing CARs comprising FN3 domains. In some embodiments, the FN3 domain antibodies and antigen-binding fragments bind to an FN3 domain that is modified in the loop regions. Table 1 provides CDR sequences of an FN3 domain-specific antibody described herein.

TABLE 1

CDR sequences of FN3 domain specific antibodies (SEQ ID NO:)

| Delineation | HC-CDR1 | HC-CDR2 | HC-CDR3 | LC-CDR1 | LC-CDR2 | LC-CDR3 |
|---|---|---|---|---|---|---|
| IMGT | GIDLSTSV (1) | IYTNVNT (4) | ARAVYAGAMDL (7) | ERIYSN (9) | KAS (11) | QYTSYGSYVGT (13) |
| Kabat | TSVMG (2) | FIYTNVNTYYASWAKG (5) | AVYAGAMDL (8) | QASERIYSNLA (10) | KASTLAS (12) | QYTSYGSYVGT (13) |
| Chothia | GIDLSTS (3) | YTNVN (6) | AVYAGAMDL (8) | QASERIYSNLA (10) | KASTLAS (12) | QYTSYGSYVGT (13) |

TABLE 1-continued

CDR sequences of FN3 domain specific antibodies
(SEQ ID NO:)

| Delineation | HC-CDR1 | HC-CDR2 | HC-CDR3 | LC-CDR1 | LC-CDR2 | LC-CDR3 |
|---|---|---|---|---|---|---|
| IMGT | GFSLNTSG TG (35) | IWWDDDK (41) | VRIKGRMDY (44) | QSVLFGSKQKNY (46) | WAS (48) | HQYLSLFT (50) |
| Kabat | TSGTGVG (36) | HIWWDDDKGYNPAL KS (42) | IKGRMDY (45) | KSSQSVLFGSKQKN YLA (47) | WASTRES (49) | HQYLSLFT (50) |
| Chothia | GFSLNTSG T (37) | WWDDD (43) | IKGRMDY (45) | KSSQSVLFGSKQKN YLA (47) | WASTRES (49) | HQYLSLFT (50) |
| IMGT | GIDFSSVA Y (38) | IYAGSSSSI (51) | ARGLFTSGSG YYIDM (54) | QSIGSD (56) | SAS (58) | QCTYSSTGY NA (60) |
| Kabat | SVAYMC (39) | CIYAGSSSSIYYASWA KG (52) | GLFTSGSGYY IDM (55) | QASQSIGSNLA (57) | GASNLAA (59) | QRGYISSAVD FFV (61) |
| Chothia | GIDFSSVA (40) | YAGSSSS (53) | GLFTSGSGYY IDM (55) | QASQSIGSNLA (57) | GASNLAA (59) | QRGYISSAVD FFV (61) |

In some embodiments, the FN3 antibody, or an antigen-binding fragment thereof, comprises a heavy chain comprising a CDR1, a CDR2, and a CDR3 of any one of the amino acid sequences described in Table 1 and a light chain comprising a CDR1, a CDR2, and a CDR3 of any one of the amino acid sequences described in Table 1. The FN3 domain antibodies of the invention may comprise the heavy chain variable regions sequence of SEQ ID NO: 14 and may comprise the light chain variable region sequence of SEQ ID NO: 15. In other embodiments, the FN3 domain antibodies of the invention may comprise the heavy chain variable regions sequence of SEQ ID NO: 74 and may comprise the light chain variable region sequence of SEQ ID NO: 75. In other embodiments, the FN3 domain antibodies of the invention may comprise the heavy chain variable regions sequence of SEQ ID NO: 78 and may comprise the light chain variable region sequence of SEQ ID NO: 79.

The FN3 domain antibodies described herein include antibodies with the described features of the CDRs and variable domains in combination with any of the IgG isotypes, including modified versions in which the Fc sequence has been modified to effect different effector functions.

In addition to the described FN3 domain antibodies and antigen-binding fragments, also provided are polynucleotide sequences capable of encoding the FN3 domain antibodies and antigen-binding fragments. Vectors comprising the described polynucleotides are also provided, as are cells expressing the FN3 domain antibodies or antigen-binding fragments provided herein. Also described are cells capable of expressing the disclosed vectors. These cells may be mammalian cells (such as 293F cells, CHO cells), insect cells (such as Sf9 cells), yeast cells, plant cells, or bacteria cells (such as E. coli). A process for the production of the FN3 domain antibodies or antigen-binding fragments is also provided.

The present invention also comprises a CAR of the invention comprising an isolated polypeptide comprising:
(a) an extracellular domain having an scFv that specifically binds to a non-randomized region of an FN3 domain;
(b) a transmembrane domain; and
(c) an intracellular signaling domain.
The CAR can further comprise a hinge region connecting the extracellular domain and the transmembrane domain.

In some embodiments, the CAR isolated polypeptide comprises:
(a) an extracellular domain comprising an FN3 domain of the invention, such as an FN3 domain having an amino acid sequence that is at least 90% identical to one of SEQ ID NOs: 68-73, preferably one of SEQ ID NOs: 68-73;
(b) a hinge region having an amino acid sequence that is at least 90% identical to SEQ ID NO: 24, preferably SEQ ID NO:24;
(c) a transmembrane domain having an amino acid sequence that is at least 90% identical to SEQ ID NO: 25, preferably SEQ ID NO:25; and
(d) an intracellular signaling domain comprising a co-stimulatory domain having an amino acid sequence that is at least 90% identical to SEQ ID NO: 26, preferably SEQ ID NO:26, and a primary signaling domain having an amino acid sequence that is at least 90% identical to SEQ ID NO: 27, preferably SEQ ID NO:27.

The present invention also comprises an isolated polynucleotide encoding a CAR of the invention comprising:
(a) an extracellular domain having an scFv that specifically binds to a non-randomized region of an FN3 domain;
(b) a transmembrane domain; and
(c) an intracellular signaling domain.
The CAR can further comprise a hinge region connecting the extracellular domain and the transmembrane domain.
In some embodiments, the isolated polynucleotide encoding a CAR comprises:
(a) an extracellular domain comprising an FN3 domain of the invention, such as an FN3 domain having an amino acid sequence that is at least 90% identical to one of SEQ ID NOs: 68-73, preferably one of SEQ ID NOs: 68-73;
(b) a hinge region having an amino acid sequence that is at least 90% identical to SEQ ID NO: 24, preferably SEQ ID NO:24;
(c) a transmembrane domain having an amino acid sequence that is at least 90% identical to SEQ ID NO: 25, preferably SEQ ID NO:25; and
(d) an intracellular signaling domain comprising a co-stimulatory domain having an amino acid sequence that is at least 90% identical to SEQ ID NO: 26, preferably SEQ ID NO:26, and a primary signaling domain having an amino acid sequence that is at least 90% identical to SEQ ID NO: 27, preferably SEQ ID NO:27.

In another general aspect, the present invention relates to a CAR of the invention, a vector comprising a polynucleotide encoding a CAR of the invention, and a host cell comprising the vector or the isolated polynucleotide encoding a CAR of the invention. The invention also relates to a method of producing a CAR of the invention, comprising culturing a host cell comprising a polynucleotide sequence encoding the CAR under conditions to produce the CAR, and recovering the CAR. The CAR can be associated with the host cell or an isolated cell membrane from the host cell.

According to another general aspect, the invention relates to engineered immune cells comprising a CAR of the invention. Preferably, the engineered immune cells are T cell receptor knockout immune cells. Preferably, the engineered immune cells are HLA I/B2-microglobulin knockout immune cells. Optionally, the HLA I/B2-microglobulin knockout immune cells are additionally HLA II knockout immune cells that are devoid of allogeneic immune responses from the host patient. The engineered immune cells can comprise a second CAR having an extracellular domain binding specifically to a target different from an FN3 domain. The engineered immune cells can also be resistant to at least one anti-cancer chemotherapy.

In another general aspect, the invention relates to pharmaceutical compositions comprising engineered immune cells of the invention.

In another general aspect, the invention relates to a method of treating a B cell-related condition in a subject in need thereof, comprising administering to the subject a therapeutically effective amount of a pharmaceutical composition of the invention. In a preferred embodiment, the B cell-related condition is multiple myeloma.

In another general aspect, the invention relates to a method of engineering an immune cell of the invention, comprising providing an immune cell, and introducing into the cell a polypeptide encoding a CAR of the invention.

In another general aspect, the invention relates to a method of producing a pharmaceutical composition, comprising combining an engineered immune cell of the invention with a pharmaceutically acceptable carrier to obtain the pharmaceutical composition Within the scope of the invention are kits including the disclosed FN3 domain antibodies or antigen-binding fragments thereof. The described kits may be used to carry out the methods of using the FN3 domain antibodies or antigen-binding fragments provided herein, or other methods known to those skilled in the art. In some embodiments, the described kits may include the FN3 domain antibodies or antigen-binding fragments described herein and reagents for use in detecting the presence of FN3 domains in a biological sample and, optionally, a vessel for containing the FN3 domain antibody or fragment when not in use, instructions for use of the FN3 domain antibody or fragment, the FN3 domain antibody or fragment affixed to a solid support, and/or detectably labeled forms of the FN3 domain antibody or fragment.

BRIEF DESCRIPTION OF THE DRAWINGS

FIG. 1A shows binding data for tencon25 which has no target specificity. FIG. 1B shows binding data for A3, which is an FN3 domain specific for human cMET. FIG. 1C shows binding data for 83v2-ABD, which is an FN3 domain specific for human EGFR with an albumin binding domain.

FIG. 2A-2M shows that AS7B91 was able to detect all CARTyrins expressed on the surface of T cells.

FIG. 4A shows H929 (BCMA high-expressing cells). FIG. 4B shows ARH77 (BCMA low-expressing cells). FIG. 4C shows K562 (BCMA negative cells). Different FN3 domains were incubated at a concentration of 50 nM with AS7B91 scFv CAR T cells, washed, and then added to target cells at a 1:1 ratio. BAR-T variant 1=AS7B91 scFv L-H CAR; BAR-T variant 2=AS7B91 scFv H-L CAR.

FIG. 7 shows binding of labeled EGFR 83v2 to AS7B16 scFv CAR constructs on T cells. L2H, AS7B16 light chain-heavy chain orientation. H2L, AS7B16 heavy chain-light chain orientation.

FIG. 11A-11B. Conjugation of Citrullinated Cyclic Peptides to Tencon25 centyrin was performed at a 1:5 ratio (centyrin to peptide) via sortase chemistry. Conjugates were purified manually over a Ni Sepharose column (GE) to remove free sortase and peptide. Following purification, the conjugates were buffered exchanged in to PBS and concentrated. Conjugates were QC'd by (a) mass spectrometry (LC-MS) and (b) size exclusion chromatography (superdex 75) and sterile filtered.

FIG. 14A discloses SEQ ID NOS 85-87, respectively, in order of appearance. FIG. 14B discloses SEQ ID NOS 88-90, respectively, in order of appearance. FIG. 14C discloses SEQ ID NOS 91-93, respectively, in order of appearance.

DETAILED DESCRIPTION OF THE INVENTION

Definitions

Figure 1A:
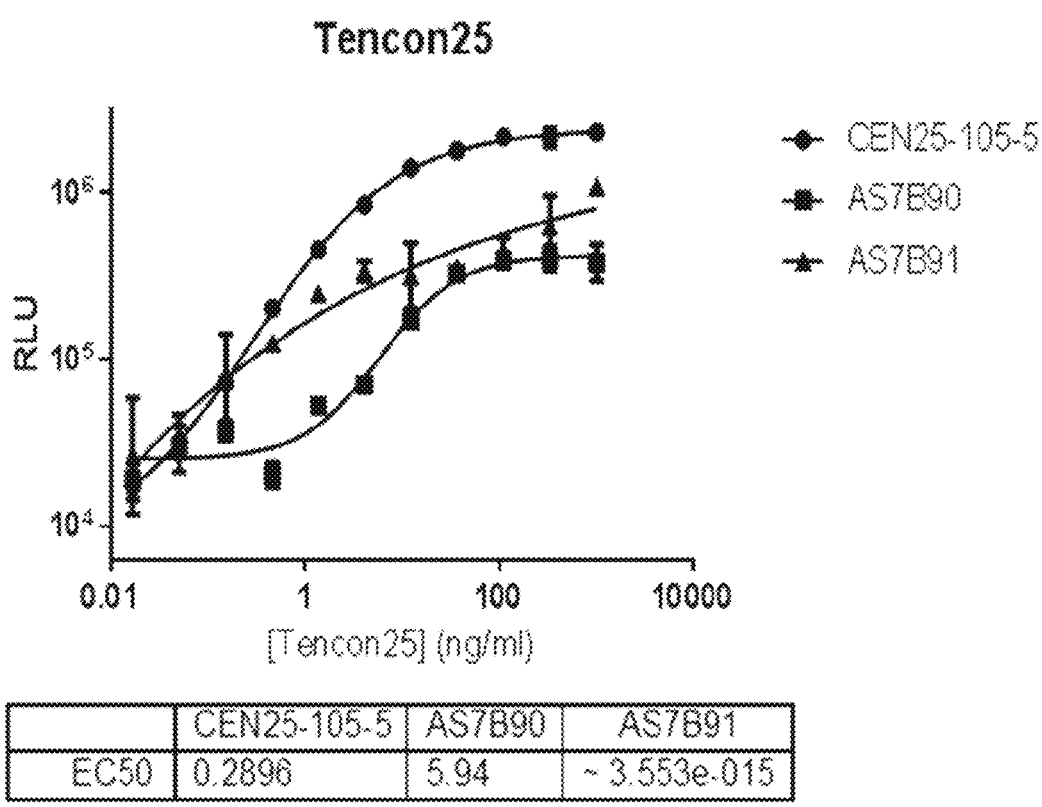
FIG. 1A-1C shows testing of recombinant AS7B90 and AS7B91 binding to immobilized FN3 domains or negative control proteins, and comparison of each to the original rabbit hybridoma derived antibody CEN25-105-5.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to ±10% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

"Isolated" means a biological component (such as a nucleic acid, peptide or protein) has been substantially separated, produced apart from, or purified away from other biological components of the organism in which the component naturally occurs, i.e., other chromosomal and extrachromosomal DNA and RNA, and proteins. Nucleic acids, peptides and proteins that have been "isolated" thus include nucleic acids and proteins purified by standard purification methods. "Isolated" nucleic acids, peptides and proteins can be part of a composition and still be isolated if such composition is not part of the native environment of the nucleic acid, peptide, or protein. The term also embraces nucleic acids, peptides and proteins prepared by recombinant expression in a host cell as well as chemically synthesized nucleic acids. An "isolated" antibody or antigen-binding fragment, as used herein, is intended to refer to an antibody or antigen-binding fragment which is substantially free of other antibodies or antigen-binding fragments having different antigenic specificities (for instance, an isolated antibody that specifically binds to an FN3 domain is substantially free of antibodies that are not specific to FN3 domains).

As used herein, the term "fibronectin type III domain" or "FN3 domain" refers to a domain occurring frequently in proteins including fibronectins, tenascin, intracellular cytoskeletal proteins, cytokine receptors and prokaryotic enzymes (Bork and Doolittle, PNAS USA 89:8990-8994, 1992; Meinke et al., J Bacteriol 175:1910-1918, 1993; Watanabe et al., J Biol Chem 265:15659-15665, 1990), or a derivative thereof. Exemplary FN3 domains are the 15 different FN3 domains present in human tenascin C, the 15 different FN3 domains present in human fibronectin (FN), and non-natural synthetic FN3 domains, for example, in U.S. Pat. No. 8,278,419. Individual FN3 domains are referred to by domain number and protein name, e.g., the $3^{rd}$ FN3 domain of tenascin (TN3), or the 10th FN3 domain of fibronectin (FN10).

"Antibody" refers to all isotypes of immunoglobulins (IgG, IgA, IgE, IgM, IgD, and IgY) including various monomeric, polymeric and chimeric forms, unless otherwise specified. Specifically encompassed by the term "antibody" are polyclonal antibodies, monoclonal antibodies (mAbs), and antibody-like polypeptides, such as chimeric antibodies and humanized antibodies.

"Antigen-binding fragments" are any proteinaceous structure that may exhibit binding affinity for a particular antigen. Antigen-binding fragments include those provided by any known technique, such as enzymatic cleavage, peptide synthesis, and recombinant techniques. Some antigen-binding fragments are composed of portions of intact antibodies that retain antigen-binding specificity of the parent antibody molecule. For example, antigen-binding fragments may comprise at least one variable region (either a heavy chain or light chain variable region) or one or more CDRs of an antibody known to bind a particular antigen. Examples of suitable antigen-binding fragments include, without limitation diabodies and single-chain molecules as well as Fab, F(ab')2, Fc, Fabc, and Fv molecules, single chain (Sc) antibodies, individual antibody light chains, individual antibody heavy chains, chimeric fusions between antibody chains or CDRs and other proteins, protein scaffolds, heavy chain monomers or dimers, light chain monomers or dimers, dimers consisting of one heavy and one light chain, a monovalent fragment consisting of the VL, VH, CL and CH1 domains, or a monovalent antibody as described in WO2007059782, bivalent fragments comprising two Fab fragments linked by a disulfide bridge at the hinge region, a Fd fragment consisting essentially of the V.sub.H and C.sub.H1 domains; a Fv fragment consisting essentially of the VL and VH domains of a single arm of an antibody, a dAb fragment (Ward et al., Nature 341, 544-546 (1989)), which consists essentially of a VH domain and also called domain antibodies (Holt et al; Trends Biotechnol. 2003 November; 21(11):484-90); camelid or nanobodies (Revets et al; Expert Opin Biol Ther. 2005 January; 5(1):111-24); an isolated complementarity determining region (CDR), and the like. All antibody isotypes may be used to produce antigen-binding fragments. Additionally, antigen-binding fragments may include non-antibody proteinaceous frameworks that may successfully incorporate polypeptide segments in an orientation that confers affinity for a given antigen of interest, such as protein scaffolds. Antigen-binding fragments may be recombinantly produced or produced by enzymatic or chemical cleavage of intact antibodies. The phrase "an antibody or antigen-binding fragment thereof" may be used to denote that a given antigen-binding fragment incorporates one or more amino acid segments of the antibody referred to in the phrase.

The terms "CDR", and its plural "CDRs", refer to a complementarity determining region (CDR) of which three make up the binding character of a light chain variable region (CDRL1, CDRL2 and CDRL3) and three make up the binding character of a heavy chain variable region (CDRH1, CDRH2 and CDRH3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by IMGT, Kabat, Chothia, or any other boundary definitions. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat et al., *Sequences of Proteins of Immunological Interest*, 5th ed. NIH Publication No. 91-3242 (1991); Chothia et al., "Canonical Structures For the Hypervariable Regions of Immunoglobulins," *J. Mol. Biol.* 196:901 (1987); and MacCallum et al., "Antibody-Antigen Interactions: Contact Analysis and Binding Site Topography," J. Mol. Biol. 262:732 (1996)), each of which is hereby incorporated by reference in its entirety.

Typically, CDRs form a loop structure that can be classified as a canonical structure. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia et al., "Canonical Structures For the Hypervariable Regions of Immunoglobulins," *J. Mol. Biol.* 196: 901 (1987); Chothia et al., "Conformations of Immunoglobulin Hypervariable Regions," I 342:877 (1989); Martin and Thornton, "Structural Families in Loops of Homologous Proteins: Automatic Classification, Modelling and Application to Antibodies," *J. Mol. Biol.* 263:800 (1996), each of which is incorporated by reference in its entirety). Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues.

"Specifically binds" or "binds specifically" or derivatives thereof when used in the context of antibodies, or antibody fragments, represents binding via domains encoded by immunoglobulin genes or fragments of immunoglobulin genes to one or more epitopes of a protein of interest, without preferentially binding other molecules in a sample containing a mixed population of molecules. Typically, an antibody binds to a cognate antigen with a $K_d$ of less than about $1\times10^{-8}$ M, as measured by a surface plasmon resonance assay, or a cell-binding assay. In a preferred embodiment, binding specificity is measure using biolayer interferometry. Phrases such as "[antigen]-specific" antibody are meant to convey that the recited antibody specifically binds the recited antigen.

"Polynucleotide," synonymously referred to as "nucleic acid molecule," "nucleotides" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

A "vector" is a replicon, such as plasmid, phage, cosmid, or virus in which another nucleic acid segment may be operably inserted so as to bring about the replication or expression of the segment.

As used herein, the term "host cell" can be any type of cell, e.g., a primary cell, a cell in culture, or a cell from a cell line. In specific embodiments, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome. The terms "expression" and "production" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression or production of an antibody or antigen-binding fragment thereof may be within the cytoplasm of the cell, or into the extracellular milieu such as the growth medium of a cell culture. The meaning of "substantially the same" can differ depending on the context in which the term is used. Because of the natural sequence variation likely to exist among heavy and light chains and the genes encoding them, one would expect to find some level of variation within the amino acid sequences or the genes encoding the antibodies or antigen-binding fragments described herein, with little or no impact on their unique binding properties (e.g., specificity and affinity). Such an expectation is due in part to the degeneracy of the genetic code, as well as to the evolutionary success of conservative amino acid sequence variations, which do not appreciably alter the nature of the encoded protein. Accordingly, in the context of nucleic acid sequences, "substantially the same" means at least 65% identity between two or more sequences. Preferably, the term refers to at least 70% identity between two or more sequences, more preferably at least 75% identity, more preferably at least 80% identity, more preferably at least 85% identity, more preferably at least 90% identity, more preferably at least 91% identity, more preferably at least 92% identity, more preferably at least 93% identity, more preferably at least 94% identity, more preferably at least 95% identity, more preferably at least 96% identity, more preferably at least 97% identity, more preferably at least 98% identity, and more preferably at least 99% or greater identity. The percent identity between two sequences is a function of the number of identical positions shared by the sequences (i.e., % homology=# of identical positions/total # of positions ×100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

The degree of variation that may occur within the amino acid sequence of a protein without having a substantial effect on protein function is much lower than that of a nucleic acid sequence, since the same degeneracy principles do not apply to amino acid sequences. Accordingly, in the context of an antibody or antigen-binding fragment, "substantially the same" means antibodies or antigen-binding fragments having 90%, 91%, 92%, 93%, 94%, 95%, 96%, 97%, 98%, or 99% identity to the antibodies or antigen-binding fragments described. Other embodiments include FN3 domain antibodies, or antigen-binding fragments, that have framework, scaffold, or other non-binding regions that do not share significant identity with the FN3 domain antibodies and antigen-binding fragments described herein, but do incorporate one or more CDRs or other sequences needed to confer binding that are 90%, 91%, 92%, 93%, 94%, 95%, 96%, 97%, 98%, or 99% identical to such sequences described herein.

As used herein, the term "chimeric antigen receptor" (CAR) refers to a recombinant polypeptide comprising at least an extracellular domain that binds specifically to an antigen or a target, a transmembrane domain and an intracellular T cell receptor-activating signaling domain. Engagement of the extracellular domain of the CAR with the target antigen on the surface of a target cell results in clustering of the CAR and delivers an activation stimulus to the CAR-containing cell. CARs redirect the specificity of immune effector cells and trigger proliferation, cytokine production, phagocytosis and/or production of molecules that can mediate cell death of the target antigen-expressing cell in a major histocompatibility (MHC)-independent manner.

As used herein, the term "extracellular antigen binding domain," "extracellular domain," or "extracellular ligand binding domain" refers to the part of a CAR that is located outside of the cell membrane and is capable of binding to an antigen, target or ligand.

As used herein, the term "hinge region" refers to the part of a CAR that connects two adjacent domains of the CAR protein, e.g., the extracellular domain and the transmembrane domain.

As used herein, the term "transmembrane domain" refers to the portion of a CAR that extends across the cell membrane and anchors the CAR to cell membrane.

As used herein, the term "intracellular T cell receptor-activating signaling domain", "cytoplasmic signaling domain," or "intracellular signaling domain" refers to the part of a CAR that is located inside of the cell membrane and is capable of transducing an effector signal.

As used herein, the term "stimulatory molecule" refers to a molecule expressed by a T cell that provides the primary cytoplasmic signaling sequence(s) that regulate primary activation of the T cell receptor (TCR) complex in a stimulatory way for at least some aspect of the T cell signaling pathway. Stimulatory molecules comprise two distinct classes of cytoplasmic signaling sequence, those that initiate antigen-dependent primary activation (referred to as "primary signaling domains"), and those that act in an antigen-independent manner to provide a secondary of co-stimulatory signal (referred to as "co-stimulatory signaling domains").

The term "expression" as used herein, and refer to the biosynthesis of a gene product. The term encompasses the transcription of a gene into RNA. The term also encompasses translation of RNA into one or more polypeptides, and further encompasses all naturally occurring post-transcriptional and post-translational modifications. The expressed FN3 domain or CAR can be within the cytoplasm of a host cell, into the extracellular milieu such as the growth medium of a cell culture, or anchored to the cell membrane.

As used herein, the term "immune cell" or "immune effector cell" refers to a cell that is involved in an immune response, e.g., in the promotion of an immune effector response. Examples of immune cells include T cells, B cells, natural killer (NK) cells, mast cells, and myeloid-derived phagocytes. According to particular embodiments, the engineered immune cells are T cells, and are referred to as CAR-T cells because they are engineered to express CARs of the invention.

As used herein, the term "engineered immune cell" refers to an immune cell, also referred to as an immune effector cell, that has been genetically modified by the addition of extra genetic material in the form of DNA or RNA to the total genetic material of the cell. According to embodiments herein, the engineered immune cells have been genetically modified to express a FN3 domain-targeting CAR according to the invention.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention.

As used herein, the term "subject" refers to an animal, and preferably a mammal. According to particular embodiments, the subject is a mammal including a non-primate (e.g., a camel, donkey, zebra, cow, pig, horse, goat, sheep, cat, dog, rat, rabbit, guinea pig or mouse) or a primate (e.g., a monkey, chimpanzee, or human). In particular embodiments, the subject is a human.

As used herein, the term "therapeutically effective amount" refers to an amount of an active ingredient or component that elicits the desired biological or medicinal response in a subject. A therapeutically effective amount can be determined empirically and in a routine manner, in relation to the stated purpose.

As used herein, the terms "treat," "treating," and "treatment" are all intended to refer to an amelioration or reversal of at least one measurable physical parameter related to a cancer or autoimmunity, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition, such as a tumor or more preferably a cancer. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

FN3 Domain Libraries

Tencon is a non-naturally occurring FN3 domain designed from a consensus sequence of fifteen FN3 domains from human tenascin-C (Jacobs et al., Protein Engineering, Design, and Selection, 25:107-117, 2012; US2010/0216708). The crystal structure of Tencon shows six surface-exposed loops that connect seven beta-strands as is characteristic to the FN3 domains, the beta-strands referred to as A, B, C, D, E, F, and G, and the loops referred to as AB, BC, CD, DE, EF, and FG loops (Bork and Doolittle, PNAS USA 89:8990-8992, 1992; U.S. Pat. No. 6,673,901). These loops, or selected residues within each loop, can be randomized in order to construct libraries of FN3 domains that can be used to select novel molecules that bind a particular antigen. Therefore, as described herein, a "non-randomized" region of an FN3 domain refers to a region within the FN3 domain that is conserved among all FN3 domains. Table 2 shows positions and sequences of each loop and beta-strand in Tencon (SEQ ID NO: 33).

TABLE 2

| FN3 domain | Tencon (SEQ ID NO: 33) |
|---|---|
| A strand | 1-12 |
| AB loop | 13-16 |
| B strand | 17-21 |
| BC loop | 22-28 |
| C strand | 29-37 |
| CD loop | 38-43 |
| D strand | 44-50 |
| DE loop | 51-54 |
| E strand | 55-59 |
| EF loop | 60-64 |
| F strand | 65-74 |
| FG loop | 75-81 |
| G strand | 82-89 |

Libraries designed based on the Tencon sequence can thus have randomized sequence in one or more of the loops or strands. For example, libraries based on Tencon can have randomized sequence in one or more of the AB loop, BC loop, CD loop, DE, EF loop and FG loop. For example, the Tencon BC loop is 7 amino acids long, thus 1, 2, 3, 4, 5, 6 or 7 amino acids can be randomized in a library based on Tencon sequence, diversified at the BC loop. The Tencon CD loop is 6 amino acids long, thus 1, 2, 3, 4, 5 or 6 amino acids can be randomized in a library based on Tencon sequence, diversified at the CD loop. The Tencon EF loop is 5 amino acids long, thus 1, 2, 3, 4 or 5 amino acids can be randomized in a library based on Tencon sequence, diversified at the EF loop. The Tencon FG loop is 7 amino acids long, thus 1, 2, 3, 4, 5, 6 or 7 amino acids can be randomized in a library based on Tencon sequence, diversified at the FG loop. Further diversity at loops in the Tencon libraries can be achieved by insertion and/or deletions of residues at loops. For example, the BC, CD, EF and/or FG loops can be extended by 1-22 amino acids, or decreased by 1-3 amino acids. The FG loop in Tencon is 7 amino acids long, whereas the corresponding loop in antibody heavy chains ranges from 4-28 residues. To provide maximum diversity, the FG loop can be diversified in sequence as well as in length to correspond to the antibody CDR3 length range of 4-28 residues. For example, the FG loop can be further diversified in length by extending the loop by an additional 1, 2, 3, 4 or 5 amino acids.

Libraries designed based on the Tencon sequence can also have randomized alternative surfaces that form on a side of the FN3 domain and comprise two or more beta strands, and at least one loop. One such alternative surface is formed by amino acids in the C and the F beta-strands and the CD and the FG loops (a C-CD-F-FG surface). A library design based on Tencon alternative C-CD-F-FG surface is described in US2013/0226834. Libraries designed based on the Tencon sequence also includes libraries designed based on Tencon variants, such as Tencon variants having substitutions at residues positions 11, 17, 46 and/or 86 (residue numbering corresponding to SEQ ID NO: 33), and which variants display improve thermal stability. Exemplary Tencon variants are described in US2011/0274623, and include Tencon27 (SEQ ID NO: 34) having substitutions E11R, L17A, N46V and E86I when compared to Tencon of SEQ ID NO: 33.

Tencon libraries and other FN3 sequence-based libraries can be randomized at chosen residue positions using a random or defined set of amino acids. For example, variants in the library having random substitutions can be generated using NNK codons, which encode all 20 naturally occurring amino acids. In other diversification schemes, DVK codons can be used to encode amino acids Ala, Trp, Tyr, Lys, Thr, Asn, Lys, Ser, Arg, Asp, Glu, Gly, and Cys. Alternatively, NNS codons can be used to give rise to all 20 amino acid residues while simultaneously reducing the frequency of stop codons. Libraries of FN3 domains with biased amino acid distribution at positions to be diversified can be synthesized, for example, using Slonomics® technology (http:_//www_sloning_com). This technology uses a library of pre-made double stranded triplets that act as universal building blocks sufficient for thousands of gene synthesis processes. The triplet library represents all possible sequence combinations necessary to build any desired DNA molecule. The codon designations are according to the well known IUB code.

FN3 Domain Antibodies and Antigen-Binding Fragments

Described herein are isolated monoclonal antibodies or antigen-binding fragments that specifically bind to a non-randomized region of FN3 domains. The general structure of an antibody molecule comprises an antigen binding domain, which includes heavy and light chains, and the Fc domain, which serves a variety of functions, including complement fixation and binding antibody receptors.

The described FN3 domain-specific antibodies or antigen-binding fragments include all isotypes, IgA, IgD, IgE, IgG and IgM, and synthetic multimers of the four-chain immunoglobulin structure. The described antibodies or antigen-binding fragments also include the IgY isotype generally found in hen or turkey serum and hen or turkey egg yolk.

The FN3 domain-specific antibodies and antigen-binding fragments may be derived from any species by recombinant means. For example, the antibodies or antigen-binding fragments may be mouse, rat, goat, horse, swine, bovine, chicken, rabbit, camelid, donkey, human, or chimeric versions thereof. For use in administration to humans, non-human derived antibodies or antigen-binding fragments may be genetically or structurally altered to be less antigenic upon administration to a human patient.

In some embodiments, the antibodies or antigen-binding fragments are chimeric. As used herein, the term "chimeric" refers to an antibody, or antigen-binding fragment thereof, having at least some portion of at least one variable domain derived from the antibody amino acid sequence of a non-human mammal, a rodent, or a reptile, while the remaining portions of the antibody, or antigen-binding fragment thereof, are derived from a human.

In some embodiments, the antibodies are humanized antibodies. Humanized antibodies may be chimeric immunoglobulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody may include at least a portion of an immunoglobulin constant region (Fc), typically that of a human immunoglobulin.

The antibodies or antigen-binding fragments described herein can occur in a variety of forms, but will include one or more of the antibody CDRs shown in Table 1.

Described herein are isolated antibodies and antigen-binding fragments that specifically bind to FN3 domains. In some embodiments, the FN3 domain-specific antibodies or antigen-binding fragments are derived from rabbits. While the FN3 domain-specific antibodies or antigen-binding fragments exemplified herein are rabbit-derived, the antibodies or antigen-binding fragments exemplified may be chimerized.

In some embodiments are provided an FN3 domain-specific antibody, or an antigen-binding fragment thereof, comprising a heavy chain comprising a CDR1, a CDR2, and a CDR3 of any one of the antibodies described in Table 1 and a light chain comprising a CDR1, a CDR2, and a CDR3 of any one of the antibodies described in Table 1.

In some embodiments, the FN3 domain-specific antibodies and antigen-binding fragments comprise a heavy chain CDR1 comprising SEQ ID NO: 1, a heavy chain CDR2 comprising SEQ ID NO: 4, a heavy chain CDR3 comprising SEQ ID NO: 7, a light chain CDR1 comprising SEQ ID NO: 9, a light chain CDR2 comprising SEQ ID NO: 11, and a light chain CDR3 comprising SEQ ID NO: 13. This FN3 domain-specific antibody or antigen-binding fragment may comprise non-rabbit framework sequences. This FN3 domain-specific antibody or antigen-binding fragment may bind to non-randomized regions of an FN3 domain, may detect the T-cell surface expression of chimeric antigen receptors (CARs) comprising FN3 domains, and may activate T-cell expressing CARs comprising FN3 domains. In some embodiments, the FN3 domain-specific antibodies and antigen-binding fragments comprise a variable heavy chain region substantially the same as, or identical to, SEQ ID NO: 14 and a variable light chain substantially the same as, or identical to, SEQ ID NO: 15. The described FN3 domain antibodies or antigen binding fragments can be used to generate CARs comprising the described antigen binding fragments.

In some embodiments, the FN3 domain-specific antibodies and antigen-binding fragments comprise a heavy chain CDR1 comprising SEQ ID NO: 2, a heavy chain CDR2 comprising SEQ ID NO: 5, a heavy chain CDR3 comprising SEQ ID NO: 8, a light chain CDR1 comprising SEQ ID NO: 10, a light chain CDR2 comprising SEQ ID NO: 12, and a light chain CDR3 comprising SEQ ID NO: 13. This FN3 domain-specific antibody or antigen-binding fragment may comprise non-rabbit framework sequences. This FN3 domain-specific antibody or antigen-binding fragment may bind to non-randomized regions of an FN3 domain, may detect the T-cell surface expression of chimeric antigen receptors (CARs) comprising FN3 domains, and may activate T-cell expressing CARs comprising FN3 domains. In some embodiments, the FN3 domain-specific antibodies and antigen-binding fragments comprise a variable heavy chain region substantially the same as, or identical to, SEQ ID NO: 14 and a variable light chain substantially the same as, or identical to, SEQ ID NO: 15. The described FN3 domain antibodies or antigen binding fragments can be used to generate CARs comprising the described antigen binding fragments.

In some embodiments, the FN3 domain-specific antibodies and antigen-binding fragments comprise a heavy chain CDR1 comprising SEQ ID NO: 3, a heavy chain CDR2 comprising SEQ ID NO: 6, a heavy chain CDR3 comprising SEQ ID NO: 8, a light chain CDR1 comprising SEQ ID NO: 10, a light chain CDR2 comprising SEQ ID NO: 12, and a light chain CDR3 comprising SEQ ID NO: 13. This FN3 domain-specific antibody or antigen-binding fragment may comprise non rabbit framework sequences. This FN3 domain-specific antibody or antigen-binding fragment may bind to non-randomized regions of an FN3 domain, may detect the T-cell surface expression of chimeric antigen receptors (CARs) comprising FN3 domains, and may activate T-cell expressing CARs comprising FN3 domains. In some embodiments, the FN3 domain-specific antibodies and antigen-binding fragments comprise a variable heavy chain region substantially the same as, or identical to, SEQ ID NO: 14 and a variable light chain substantially the same as, or identical to, SEQ ID NO: 15. The described FN3 domain antibodies or antigen binding fragments can be used to generate CARs comprising the described antigen binding fragments.

In some embodiments, the FN3 domain-specific antibodies and antigen-binding fragments comprise a heavy chain CDR1 having the amino acid sequence of SEQ ID NO: 35, a heavy chain CDR2 having the amino acid sequence of SEQ ID NO: 41, a heavy chain CDR3 having the amino acid sequence of SEQ ID NO: 44, a light chain CDR1 having the amino acid sequence of SEQ ID NO: 46, a light chain CDR2 having the amino acid sequence of SEQ ID NO: 48, and a light chain CDR3 having the amino acid sequence of SEQ ID NO: 50. This FN3 domain-specific antibody or antigen-binding fragment may comprise non mouse framework sequences. This FN3 domain-specific antibody or antigen-binding fragment may bind to non-randomized regions of an FN3 domain, may detect the T-cell surface expression of chimeric antigen receptors (CARs) comprising FN3 domains, and may activate T-cell expressing CARs comprising FN3 domains. In some embodiments, the FN3 domain-specific antibodies and antigen-binding fragments comprise a variable heavy chain region substantially the same as, or identical to, SEQ ID NO: 74 and a variable light chain substantially the same as, or identical to, SEQ ID NO: 75. The described FN3 domain antibodies or antigen binding fragments can be used to generate CARs comprising the described antigen binding fragments.

In some embodiments, the FN3 domain-specific antibodies and antigen-binding fragments comprise a heavy chain CDR1 having the amino acid sequence of SEQ ID NO: 36, a heavy chain CDR2 having the amino acid sequence of SEQ ID NO: 42, a heavy chain CDR3 having the amino acid sequence of SEQ ID NO: 45, a light chain CDR1 having the amino acid sequence of SEQ ID NO: 47 a light chain CDR2 having the amino acid sequence of SEQ ID NO: 49, and a light chain CDR3 having the amino acid sequence of SEQ ID NO: 50. This FN3 domain-specific antibody or antigen-binding fragment may comprise non mouse framework sequences. This FN3 domain-specific antibody or antigen-binding fragment may bind to non-randomized regions of an FN3 domain, may detect the T-cell surface expression of chimeric antigen receptors (CARs) comprising FN3 domains, and may activate T-cell expressing CARs comprising FN3 domains. In some embodiments, the FN3 domain-specific antibodies and antigen-binding fragments comprise a variable heavy chain region substantially the same as, or identical to, SEQ ID NO: 74 and a variable light chain substantially the same as, or identical to, SEQ ID NO: 75. The described FN3 domain antibodies or antigen binding fragments can be used to generate CARs comprising the described antigen binding fragments.

In some embodiments, the FN3 domain-specific antibodies and antigen-binding fragments comprise a heavy chain CDR1 having the amino acid sequence of SEQ ID NO: 37, a heavy chain CDR2 having the amino acid sequence of SEQ ID NO: 43, a heavy chain CDR3 having the amino acid sequence of SEQ ID NO: 45, a light chain CDR1 having the amino acid sequence of SEQ ID NO: 47, a light chain CDR2 having the amino acid sequence of SEQ ID NO: 49, and a light chain CDR3 having the amino acid sequence of SEQ ID NO: 50. This FN3 domain-specific antibody or antigen-binding fragment may comprise non mouse framework sequences. This FN3 domain-specific antibody or antigen-binding fragment may bind to non-randomized regions of an FN3 domain, may detect the T-cell surface expression of chimeric antigen receptors (CARs) comprising FN3 domains, and may activate T-cell expressing CARs comprising FN3 domains. In some embodiments, the FN3 domain-specific antibodies and antigen-binding fragments comprise a variable heavy chain region substantially the same as, or identical to, SEQ ID NO: 74 and a variable light chain substantially the same as, or identical to, SEQ ID NO: 75. The described FN3 domain antibodies or antigen binding fragments can be used to generate CARs comprising the described antigen binding fragments.

In some embodiments, the FN3 domain-specific antibodies and antigen-binding fragments comprise a heavy chain CDR1 having the amino acid sequence of SEQ ID NO: 38, a heavy chain CDR2 having the amino acid sequence of SEQ ID NO: 51, a heavy chain CDR3 having the amino acid sequence of SEQ ID NO: 54, a light chain CDR1 having the amino acid sequence of SEQ ID NO: 56, a light chain CDR2 having the amino acid sequence of SEQ ID NO: 58, and a light chain CDR3 having the amino acid sequence of SEQ ID NO: 60. This FN3 domain-specific antibody or antigen-binding fragment may comprise non mouse framework sequences. This FN3 domain-specific antibody or antigen-binding fragment may bind to non-randomized regions of an FN3 domain, may detect the T-cell surface expression of chimeric antigen receptors (CARs) comprising FN3 domains, and may activate T-cell expressing CARs comprising FN3 domains. In some embodiments, the FN3 domain-specific antibodies and antigen-binding fragments comprise a variable heavy chain region substantially the same as, or identical to, SEQ ID NO: 78 and a variable light chain substantially the same as, or identical to, SEQ ID NO: 79. The described FN3 domain antibodies or antigen binding fragments can be used to generate CARs comprising the described antigen binding fragments.

In some embodiments, the FN3 domain-specific antibodies and antigen-binding fragments comprise a heavy chain CDR1 having the amino acid sequence of SEQ ID NO: 39, a heavy chain CDR2 having the amino acid sequence of SEQ ID NO: 52, a heavy chain CDR3 having the amino acid sequence of SEQ ID NO: 55, a light chain CDR1 having the amino acid sequence of SEQ ID NO: 57 a light chain CDR2 having the amino acid sequence of SEQ ID NO: 59, and a light chain CDR3 having the amino acid sequence of SEQ ID NO: 61. This FN3 domain-specific antibody or antigen-binding fragment may comprise non mouse framework sequences. This FN3 domain-specific antibody or antigen-binding fragment may bind to non-randomized regions of an FN3 domain, may detect the T-cell surface expression of chimeric antigen receptors (CARs) comprising FN3 domains, and may activate T-cell expressing CARs comprising FN3 domains. In some embodiments, the FN3 domain-specific antibodies and antigen-binding fragments comprise a variable heavy chain region substantially the same as, or identical to, SEQ ID NO: 78 and a variable light chain substantially the same as, or identical to, SEQ ID NO: 79. The described FN3 domain antibodies or antigen binding fragments can be used to generate CARs comprising the described antigen binding fragments.

In some embodiments, the FN3 domain-specific antibodies and antigen-binding fragments comprise a heavy chain CDR1 having the amino acid sequence of SEQ ID NO: 40, a heavy chain CDR2 having the amino acid sequence of SEQ ID NO: 53, a heavy chain CDR3 having the amino acid sequence of SEQ ID NO: 55, a light chain CDR1 having the amino acid sequence of SEQ ID NO: 57, a light chain CDR2 having the amino acid sequence of SEQ ID NO: 59, and a light chain CDR3 having the amino acid sequence of SEQ ID NO: 61. This FN3 domain-specific antibody or antigen-binding fragment may comprise non mouse framework sequences. This FN3 domain-specific antibody or antigen-binding fragment may bind to non-randomized regions of an FN3 domain, may detect the T-cell surface expression of chimeric antigen receptors (CARs) comprising FN3 domains, and may activate T-cell expressing CARs comprising FN3 domains. In some embodiments, the FN3 domain-specific antibodies and antigen-binding fragments comprise a variable heavy chain region substantially the same as, or identical to, SEQ ID NO: 78 and a variable light chain substantially the same as, or identical to, SEQ ID NO: 79. The described FN3 domain antibodies or antigen binding fragments can be used to generate CARs comprising the described antigen binding fragments.

Also disclosed are isolated polynucleotides that encode the antibodies or antigen-binding fragments that specifically bind to an FN3 domain. The isolated polynucleotides capable of encoding the variable domain segments provided herein may be included on the same, or different, vectors to produce antibodies or antigen-binding fragments.

Polynucleotides encoding recombinant antigen-binding proteins also are within the scope of the disclosure. In some embodiments, the polynucleotides described (and the peptides they encode) include a leader sequence. Any leader sequence known in the art may be employed. The leader sequence may include, but is not limited to, a restriction site or a translation start site.

The FN3 domain-specific antibodies or antigen-binding fragments described herein include variants having single or multiple amino acid substitutions, deletions, or additions that retain the biological properties (e.g., binding affinity or immune effector activity) of the described FN3 domain-specific antibodies or antigen-binding fragments. These variants may include: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies or antigen-binding fragments described herein may include variants in which amino acid residues from one species are substituted for the corresponding residue in another species, either at the conserved or nonconserved positions. In other embodiments, amino acid residues at nonconserved positions are substituted with conservative or nonconservative residues. The techniques for obtaining these variants, including genetic (deletions, mutations, etc.), chemical, and enzymatic techniques, are known to persons having ordinary skill in the art.

The FN3 domain-specific antibodies or antigen-binding fragments described herein may embody several antibody isotypes, such as IgM, IgD, IgG, IgA and IgE. In some embodiments, the antibody isotype is IgG. Antibody or antigen-binding fragment thereof specificity is largely determined by the amino acid sequence, and arrangement, of the CDRs. Therefore, the CDRs of one isotype may be transferred to another isotype without altering antigen specificity. Alternatively, techniques have been established to cause hybridomas to switch from producing one antibody isotype to another (isotype switching) without altering antigen specificity. Accordingly, such antibody isotypes are within the scope of the described antibodies or antigen-binding fragments.

The affinity of the described FN3 domain-specific antibodies, or antigen-binding fragments, may be determined by a variety of methods known in the art, such as surface plasmon resonance or ELISA-based methods. Assays for measuring affinity by SPR include assays performed using a BIAcore 3000 machine, where the assay is performed at room temperature (e.g. at or near 25° C.), wherein the antibody capable of binding to FN3 domains is captured on the BIAcore sensor chip by an anti-Fc antibody (e.g. goat anti-human IgG Fc specific antibody Jackson ImmunoResearch laboratories Prod #109-005-098) to a level around 75RUs, followed by the collection of association and dissociation data at a flow rate of 40 µl/min.

Methods of Detecting FN3 Domains

Provided herein are methods for detecting FN3 domains in a biological sample by contacting the sample with an antibody, or antigen-binding fragment thereof, described herein. As described herein, the sample may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments, the described methods include detecting FN3 domains in a biological sample by contacting the sample with any of the FN3 domain-specific antibodies or antigen-binding fragments thereof described herein.

In some embodiments, the sample may be contacted with more than one of the FN3 domain-specific antibodies or antigen-binding fragments described herein. For example, a sample may be contacted with a first FN3 domain-specific antibody, or antigen-binding fragment thereof, and then contacted with a second FN3 domain-specific antibody, or antigen-binding fragment thereof, wherein the first antibody or antigen-binding fragment and the second antibody or antigen-binding fragment are not the same antibody or antigen-binding fragment. In some embodiments, the first antibody, or antigen-binding fragment thereof, may be affixed to a surface, such as a multiwell plate, chip, or similar substrate prior to contacting the sample. In other embodiments the first antibody, or antigen-binding fragment thereof, may not be affixed, or attached, to anything at all prior to contacting the sample.

The described FN3 domain-specific antibodies and antigen-binding fragments may be detectably labeled. In some embodiments labeled antibodies and antigen-binding fragments may facilitate the detection of FN3 domains via the methods described herein. Many such labels are readily known to those skilled in the art. For example, suitable labels include, but should not be considered limited to, radiolabels, fluorescent labels, epitope tags, biotin, chromophore labels, ECL labels, or enzymes. More specifically, the described labels include ruthenium, $^{111}$In-DOTA, $^{111}$In-diethylenetriaminepentaacetic acid (DTPA), horseradish peroxidase, alkaline phosphatase and beta-galactosidase, poly-histidine (HIS tag), acridine dyes, cyanine dyes, fluorone dyes, oxazin dyes, phenanthridine dyes, rhodamine dyes, Alexafluor® dyes, and the like.

The described FN3 domain-specific antibodies and antigen-binding fragments may be used in a variety of assays to detect FN3 domains in a biological sample. Some suitable assays include, but should not be considered limited to, western blot analysis, radioimmunoassay, surface plasmon resonance, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

Kits for Detecting FN3 Domains

Provided herein are kits for detecting FN3 domains in a biological sample. These kits include one or more of the FN3 domain antibodies described herein, or an antigen-binding fragment thereof, and instructions for use of the kit.

The provided FN3 domain antibody, or antigen-binding fragment, may be in solution; lyophilized; affixed to a substrate, carrier, or plate; or detectably labeled.

The described kits may also include additional components useful for performing the methods described herein. By way of example, the kits may comprise means for obtaining a sample from a subject, a control or reference sample, e.g., a sample from a subject having slowly progressing cancer and/or a subject not having cancer, one or more sample compartments, and/or instructional material which describes performance of a method of the invention and tissue specific controls or standards.

The means for determining the level of FN3 domains can further include, for example, buffers or other reagents for use in an assay for determining the level of FN3 domains. The instructions can be, for example, printed instructions for performing the assay and/or instructions for evaluating the level of expression of FN3 domains.

The described kits may also include means for isolating a sample from a subject. These means can comprise one or more items of equipment or reagents that can be used to obtain a fluid or tissue from a subject. The means for obtaining a sample from a subject may also comprise means for isolating blood components, such as serum, from a blood sample. Preferably, the kit is designed for use with a human subject.

FN3 Domain-Targeting Chimeric Antigen Receptors (CARs)

In other general aspects, the invention relates to an FN3 domain-targeting CAR comprising an FN3 domain-specific scFv.

In one aspect, the invention relates to a CAR comprising:
a. an extracellular domain having an scFv that specifically binds to a non-randomized region of an FN3 domain;
b. a transmembrane domain; and
c. an intracellular signaling domain.

In some embodiments, in a nascent CAR, the extracellular domain is preceded by a signal peptide at the N-terminus. Any suitable signal peptide can be used in the invention. The signal peptide can be derived from a natural, synthetic, semi-synthetic or recombinant source.

According to embodiments of the invention, the extracellular domain of a CAR comprises an scFv that specifically binds to a non-randomized region of an FN3 domain. Any scFv that specifically binds to an FN3 domain according to embodiments of the invention, including but not limited to those described herein, can be used in the extracellular domain of the CAR.

According to embodiments of the invention, a CAR can further comprise a hinge region connecting the extracellular domain and the transmembrane domain. The hinge region functions to move the extracellular domain away from the surface of the engineered immune cell to enable proper cell/cell contact, binding to the target or antigen and activation (Patel et al., Gene Therapy, 1999; 6: 412-419). Any suitable hinge region can be used in a CAR of the invention. It can be derived from a natural, synthetic, semi-synthetic or recombinant source. According to some embodiments, the hinge region of the CAR is a 6×GS peptide (SEQ ID NO: 84), or a fragment thereof, or a hinge region from a CD8 protein, or a derivative thereof. In particular embodiments, the hinge region has an amino acid sequence at least 90% identical to SEQ ID NO: 24, preferably the amino acid sequence of SEQ ID NO: 24.

Any suitable transmembrane domain can be used in a CAR of the invention. The transmembrane domain can be derived from a natural, synthetic, semi-synthetic or recombinant source. According to some embodiments, the transmembrane domain is a transmembrane domain from molecules such as CD8, CD28, CD4, CD2, GMCSFR and the like. In particular embodiments, the transmembrane domain has an amino acid sequence at least 90% identical to SEQ ID NO: 25, preferably the amino acid sequence of SEQ ID NO: 25.

Any suitable intracellular signaling domain can be used in a CAR of the invention. In particular embodiments, the entire intracellular signaling domain is used. In other particular embodiments, a truncated portion of the signaling domain that transduces the effector signal is used. According to embodiments of the invention, the intracellular signaling domain generates a signal that promotes an immune effector function of the CAR-containing cell, e.g. a CAR-T cell, including, but not limited to, proliferation, activation, and/or differentiation. In particular embodiments, the signal promotes, e.g., cytolytic activity, helper activity, and/or cytokine secretion of the CAR-T cell. In other embodiments, no intracellular signaling domain is used in a CAR of the invention and the CAR comprising an scFv that specifically binds to an FN3 domain of the invention is used along with an FN3 domain for targeting the effector cell to target cells.

According to some embodiments, the intracellular signaling domain comprises a functional signaling domain derived from CD3 zeta, TCR zeta, FcR gamma, FcR beta, CD3 gamma, CD3 delta, CD3 epsilon, CD16, CD22, CD27, CD28, CD30, CD79a, CD79b, CD134 (also known as TNFRSF4 or OX-40), 4-1BB (CD137), CD278 (also known as ICOS), FcεRI, DAP10, DAP12, ITAM domains or CD66d, and the like. According to particular embodiments, the intracellular signaling domain comprises a primary signaling domain and one or more co-stimulatory signaling domains.

In one embodiment, the intracellular signaling domain comprises a primary intracellular signaling domain having a functional signaling domain derived from human CD3zeta. In particular embodiments, the primary intracellular signaling domain has an amino acid sequence at least 90% identical to SEQ ID NO: 27, preferably the amino acid sequence of SEQ ID NO: 27.

According to some embodiments, the intracellular signaling domain further comprises the co-stimulatory intracellular signaling domain derived from human 4-1BB. In particular embodiments, the co-stimulatory intracellular signaling domain has an amino acid sequence at least 90% identical to SEQ ID NO: 26, preferably the amino acid sequence of SEQ ID NO: 26.

In one embodiment, a CAR of the invention is associated with a host cell expressing the CAR.

In another embodiment, a CAR of the invention is present in an isolated cell membrane of the host cell expressing the CAR.

In yet another embodiment, a CAR of the invention is purified or isolated from other components of the host cell expressing the CAR.

Polynucleotides, Vectors and Host Cells

In other general aspects, the invention relates to isolated polynucleotides and vectors encoding FN3 domain antibodies or CARs of the invention, and recombinant cells containing the vectors.

Nucleic acids encoding any of the various proteins or polypeptides disclosed herein can be synthesized chemically or using other methods in the art in view of the present disclosure. Codon usage can be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., PNAS USA. 2003 100(2):438-42; Sinclair et al. Protein Expr Purif. 2002 (1):96-105; Connell, Curr Opin Biotechnol. 2001 (5):446-9; Makrides et al. Microbiol Rev. 1996 60(3):512-38; and Sharp et al. Yeast. 1991 7(7):657-78.

General techniques for nucleic acid manipulation are within the purview of one skilled in the art and are also described, for example, in Sambrook et al., Molecular Cloning: A Laboratory Manual, Vols. 1-3, Cold Spring Harbor Laboratory Press, 2 ed., 1989, or Ausubel et al., eds, 1994, Current Protocols in Molecular Biology, Vol. 1, John Wiley & Sons, Inc., New York, and periodic updates, herein incorporated by reference. The DNA encoding a protein is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants are additionally incorporated. Suitable regulatory elements are well-known in the art.

It will be appreciated by those skilled in the art that the coding sequence of a protein can be changed without changing the amino acid sequence of the protein. Accordingly, it will be understood by those skilled in the art that nucleic acid sequences encoding FN3 domain antibodies or CARs of the invention can be altered without changing the amino acid sequences of the proteins.

In one embodiment, the invention relates to a vector comprising an isolated nucleic acid encoding an FN3 domain antibody or a CAR of the invention. Any vector known to those skilled in the art in view of the present disclosure can be used, such as a plasmid, cosmid, a phage vector or a viral vector. In one embodiment, the vector is an expression vector comprising a polynucleotide sequence encoding an FN3 domain or a CAR of the invention operably linked to a promoter sequence, optionally one or more other regulatory sequences.

In another embodiment, the invention relates to transient expression of a CAR of the invention by an mRNA encoding the CAR. In one aspect, the mRNA encoding the CAR is introduced into an immune effector cell as a form of transient transfection, wherein the expression of the non-integrated transgene is expressed for a period of hours, days or weeks, wherein the period of time of expression is less than the period of time for expression of the gene if integrated into the genome or contained within a stable plasmid replicon in the host cell. In one aspect, the mRNA is produced by in vitro transcription using a PCR-generated template.

In another general aspect, the invention relates to a host cell comprising an isolated nucleic acid encoding an FN3 domain antibody or a CAR of the invention. The host cell can be stably or transiently transfected with a nucleic acid molecule of the invention.

Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae*, can also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). In some instances, it will be desired to produce proteins in vertebrate cells, such as for glycosylation, and the propagation of vertebrate cells in culture (tissue culture) has become a routine procedure. Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines.

A host cell of the invention can be an engineered FN3 domain-targeting immune cell, which is described in detail infra.

Protein Production

In another general aspect, the invention relates to a method of producing an FN3 domain antibody of the invention, comprising culturing a host cell comprising a nucleic acid encoding the FN3 domain antibody under conditions to produce the FN3 domain antibody of the invention, and recovering the FN3 domain antibody from the cell or cell culture (e.g., from the supernatant). Expressed FN3 domain antibodies can be harvested from the cells or cell culture and purified according to conventional techniques known in the art in view of the present disclosure.

In another general aspect, the invention relates to a method of producing a CAR of the invention, comprising culturing a host cell comprising a nucleic acid encoding the CAR under conditions to produce the CAR of the invention, and recovering the CAR. Expressed CARs can be harvested from the cells and purified according to conventional techniques known in the art and as described herein.

Host cells are transformed with the expression or cloning vectors for protein production and cultured in conventional nutrient media modified as appropriate, e.g., for inducing promoters, selecting transformants, or amplifying the genes encoding the desired sequences.

The host cells used to produce the proteins of this invention can be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al, Meth. Enz. 58:44 (1979); Barnes et al, Anal. Biochem. 102:255 (1980); U.S. Pat. Nos. 4,767,704; 4,657,866; 4,927,762; 4,560,655; 5,122,469; WO90/03430; WO87/00195 or USRE30985 can be used as culture media for the host cells. Any of these media can be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements can also be included at appropriate concentrations that would be known to those skilled in the art. The culture conditions, such as temperature, pH, and the like, are those previously used with the host cell selected for expression, and will be apparent to the ordinarily skilled artisan.

Proteins disclosed herein can also be produced using cell-translation systems in vitro. For such purposes, the nucleic acids encoding the proteins must be modified to allow in vitro transcription to produce mRNA and to allow cell-free translation of the mRNA in the particular cell-free system being utilized. Exemplary eukaryotic cell-free translation systems include, for example, mammalian or yeast cell-free translation systems, and exemplary prokaryotic cell-free translation systems include, for example, bacterial cell-free translation systems.

Proteins disclosed herein can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

The proteins disclosed herein can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, proteins can be exchanged into different buffers and/or concentrated by any of a variety of methods known to the art, including, but not limited to, filtration and dialysis.

The purified proteins are preferably at least 85% pure, more preferably at least 95% pure, and most preferably at least 98% pure.

Engineered FN3 Domain-Targeting CAR-T Cells, Compositions and Methods Thereof

In another general aspect, the invention relates to engineered FN3 domain-targeting immune cells comprising an FN3 domain-targeting CAR of the invention, methods of making the engineered immune cells, compositions comprising the engineered immune cells, and methods of using the engineered immune cells to treat diseases such as multiple myeloma.

In one general aspect, the invention relates to engineered immune cells comprising FN3 domain-targeting CARs of the invention.

According to some embodiments, the immune cell can be made less allogeneic, for instance, by inactivating at least one gene expressing one or more component of T cell receptor (TCR) as described in WO 2013/176915, which can be combined with the inactivation of a gene encoding or regulating HLA I/B2-microglobulin (B2M) protein expression. Accordingly, the risk of graft versus host syndrome and graft rejection is significantly reduced. A T cell lacking a functional TCR, referred to as a "TCR knockout" or a "TCR-KO" cell, can be engineered such that it does not express any functional TCR on its surface, engineered such that it does not express one or more subunits that comprise a functional TCR (e.g., engineered such that it does not express (or exhibits reduced expression) of TCR alpha, TCR beta, TCR gamma, TCR delta, TCR epsilon, and/or TCR zeta) or engineered such that it produces very little functional TCR on its surface. Alternatively, the T cell can express a substantially impaired TCR (i.e., a TCR that will not elicit an adverse immune reaction in a host), e.g., by expression of mutated or truncated forms of one or more of the subunits of the TCR. Modified T cells that lack expression of a functional TCR and/or B2M can be obtained by any suitable means, including a knock out or knock down of one or more subunit of TCR and/or B2M. For example, the T cell can include a knock down of TCR and/or B2M using siRNA, shRNA, clustered regularly interspaced short palindromic repeats (CRISPR), transcription-activator like effector nuclease (TALEN), megaTAL, meganuclease, or zinc finger endonuclease (ZFN).

In particular embodiments, the immune effector cell comprising an FN3 domain-targeting CAR of the invention is a T cell, a NKT cell or a NK cell, preferably, a human T cell or human NK cell, more preferably a TCR knockout cell, most preferably a human TCR knockout cell and/or an HLA I/B2M knockout cell. In other embodiments, the immune effector cell comprising a FN3 domain-targeting CAR of the invention is an engineered T cell line, such as a TALL-104 T cell line (i.e., a IL-2-dependent human non-restricted cytotoxic T cell line that expresses CD8 and CD3 but not CD16).

Immune effector cells of the invention can be autologous (i.e., "self," e.g., autogenic) or non-autologous (i.e., "non-self," e.g., allogeneic, syngenic, xenogenic). Autologous refers to any material derived from the same individual into whom it is later to be re-introduced. Non-autologous refers to any material derived from a different individual of the same species as the individual into whom the material is later to be introduced In another general aspect, the invention relates to methods of making the engineered FN3 domain-targeting immune cells comprising FN3 domain-targeting CARs of the invention. A vector encoding the CAR can be directly transduced into an immune cell. Alternatively, in vitro transcribed RNA or synthetic RNA encoding the CAR can be introduced into an immune cell.

According to particular embodiments, the method of making the engineered FN3 domain-targeting immune cells comprises transfecting or transducing immune effector cells isolated from an individual such that the immune effector cells express one or more CAR(s) according to embodiments of the invention. Methods of preparing immune cells for immunotherapy are described, e.g., in WO2014/130635, WO2013/176916 and WO2013/176915, which are incorporated herein by reference. Individual steps that can be used for preparing engineered immune cells are disclosed, e.g., in WO2014/039523, WO2014/184741, WO2014/191128, WO2014/184744 and WO2014/184143, which are incorporated herein by reference.

In a particular embodiment, the immune effector cells, such as T cells, are genetically modified with CARs of the invention (e.g., transduced with a viral vector comprising a nucleic acid encoding a CAR) and then are activated and expanded in vitro. In various embodiments, T cells can be activated and expanded before or after genetic modification to express a CAR, using methods as described, for example, in U.S. Pat. Nos. 6,352,694, 6,534,055, 6,905,680, 6,692,964, 5,858,358, 6,887,466, U.S. Pat. Nos. 6,905,681, 7,144,575, 7,067,318, 7,172,869, 7,232,566, 7,175,843, 5,883,223, 6,905,874, 6,797,514, 6,867,041, US2006/121005, which are incorporated herein by reference. T cells can be expanded in vitro or in vivo. Generally, the T cells of the invention can be expanded by contact with a surface having attached thereto an agent that stimulates a CD3/TCR complex-associated signal and a ligand that stimulates a co-stimulatory molecule on the surface of the T cells. As non-limiting examples, T cell populations can be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore, or by activation of the CAR itself. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include, e.g., an appropriate media (e.g., Minimal Essential Media or RPMI Media 1640 or, X-vivo 5 (Lonza)) that can contain factors necessary for proliferation and viability, including serum (e.g., fetal bovine or human serum), cytokines, such as IL-2, IL-7, IL-15, and/or IL-21, insulin, IFN-g, GM-CSF, TGFb and/or any other additives for the growth of cells known to the skilled artisan. In other embodiments, the T cells can be activated and stimulated to proliferate with feeder cells and appropriate antibodies and cytokines using methods such as those described in U.S. Pat. Nos. 6,040,177, 5,827,642, and WO2012129514, which are incorporated herein by reference.

In some embodiments, a CAR-expressing cell of the invention can further comprise a second CAR having an extracellular domain that specifically binds to the same target or a different target. Preferably, the immune cell expresses two CARs that specifically bind to two different targets, or the immune cell expresses a bispecific receptor, such as a CAR comprising two FN3 domains that specifically bind to two different targets, i.e., an FN3 domain and another target, associated with a disease of interest. For example, the other target can also be associated with a type of cancer. More preferably, the two CARs also have different intracellular signaling domains, for example, the first CAR has a costimulatory signaling domain but not a primary signaling domain, and the second CAR has a primary signaling domain but not a costimulatory signaling domain, or vice versa. By the placement of a costimulatory signaling domain, such as that from 4-1BB, CD28, CD27 ICOS, or OX-40, onto one CAR, and the primary signaling domain, such as that from CD3 zeta, on the other CAR, one can limit the CAR activity to cells where both targets are expressed, e.g., for enhanced specificity.

In some embodiments, a CAR-expressing cell of the invention can further comprise an inhibitory CAR as a self-regulating safety switch to constrain T cell-based therapies and avoid off-tumor toxicity. For example, the inhibitory CAR can include an extracellular domain that binds specifically to a target found on normal cells but not on the target cancer cells. The inhibitory CAR also includes an intracellular domain having an inhibitory receptor signaling domain, such as an intracellular domain of an inhibitory molecule including, but not limited to, PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, and TGFR beta. Cells expressing an FN3 domain-targeting CAR and an inhibitory CAR are suppressed when encountering a normal cell, but activated when encountering a tumor cell not expressing the normal cell target.

In some other embodiments, a CAR-expressing cell of the invention can further comprise an agent that enhances the activity of a CAR-expressing cell. For example, the agent can inhibit the activity of an inhibitory molecule, such as those described herein, in the host cell.

According to particular embodiments, the engineered immune CAR-expressing cells are further genetically engineered to be chemoresistant. This chemoresistance can allow the engineered immune cells to survive in the presence of drugs while selectively targeting an FN3 domain of interest.

According to some embodiments, drug resistance can be conferred on the CAR-expressing cells by genetically engineering them to express at least one drug resistance gene. A drug resistance gene of the invention can encode resistance to anti-metabolite, methotrexate, vinblastine, cisplatin, alkylating agents, anthracyclines, cytotoxic antibiotics, anti-immunophilins, their analogs or derivatives, etc. Several drug resistance genes have been identified that can be used to confer drug resistance to engineered immune CAR-expressing cells of the invention. See, e.g., Takebe et al., Mol Ther. 2001 January; 3(1):88-96; Sugimoto et al, J Gene Med. 2003 May; 5(5):366-76; Zielske et al., J Clin Invest. 2003 November; 112(10):1561-70; Nivens et al, Cancer Chemother Pharmacol. 2004 February; 53(2):107-15; Bardenheuer et al., Leukemia. 2005 December; 19(12): 2281-8; Kushman et al., Carcinogenesis. 2007 January; 28(1):207-14. Examples of drug resistance genes that can be expressed in the cells include a mutant or modified form of Dihydrofolate reductase (DHFR), a mutant or modified form of ionisine-5′-monophosphate dehydrogenase II (IMPDH2), multidrug resistance protein 1 (MDR1), calcineurin, methylguanine transferase (MGMT), microRNA-21, the antibiotic resistance genes ble and mcrA, etc. According to particular embodiments, said drug resistance genes can be expressed in the cell by any suitable means, including, e.g., introducing a transgene encoded by at least one vector into a cell.

Resistance to anti-cancer chemotherapies can also be conferred, e.g., by inactivating genes that are responsible for the cell's sensitivity to the drug. Examples of genes that can be inactivated to confer drug resistance to the cells include, e.g., CD52, glucocorticoid receptors, CD3, human hypoxanthine-guanine phosphoribosyl transferase (HPRT), human deoxycytidine kinase (dCK), etc. Genes responsible for the cell's sensitivity to anti-cancer drugs can be inactivated by any suitable means, including a knock out or knock down of the gene, e.g., using siRNA, shRNA, CRISPR, TALEN, or ZFN.

In another general aspect, the invention relates to a pharmaceutical composition, comprising an engineered FN3 domain-targeting immune cell of the invention and a pharmaceutically acceptable carrier. In view of the present disclosure, any pharmaceutically acceptable carrier suitable for use in CAR-T pharmaceutical composition can be used in the invention.

In another general aspect, the invention relates to a method of treating a cancer in a subject in need thereof, comprising administering to the subject a therapeutically effective amount of a pharmaceutical composition of the invention.

According to embodiments of the invention, a therapeutically effective amount of the pharmaceutical composition stimulates an immune response in a subject in need thereof, preferably results in treatment of a disease, disorder, or condition; prevents or slows the progression of the disease, disorder, or condition; or reduces or completely alleviates symptoms associated with the immune disease, disorder, or condition.

According to particular embodiments, the disease, disorder or condition to be treated is a hyperproliferative disease. According to other particular embodiments, the disease, disorder or condition to be treated is a cancer or tumor, or a malignant hyperproliferative disease, preferably a cancer selected from the group consisting of a solid tumor, a hematologic cancer, bladder cancer, biliary cancer, brain cancer, breast cancer, colon cancer, esophageal cancer, gastric cancer, glioma, head cancer, leukemia, liver cancer, lung cancer, lymphoma, multiple myeloma, neck cancer, ovarian cancer, melanoma, pancreatic cancer, renal cancer, salivary cancer, stomach cancer, thymic epithelial cancer, and thyroid cancer.

According to particular embodiments, a therapeutically effective amount of the FN3 domain-targeting immune cell composition is sufficient to achieve one, two, three, four, or more of the following effects in a subject in need thereof: (i) reduce or ameliorate the severity of the disease, disorder or condition to be treated or a symptom associated therewith;

(ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy. In particular embodiments, a therapeutically effective amount refers to the amount of therapy which is sufficient to achieve one, two, three, four, or more of the following effects: (i) decrease the tumor volume; (ii) decrease the number of tumor cells; (iii) decrease the number of metastases; (iv) increase the life expectancy; (v) decrease tumor cell proliferation; (vi) decrease tumor cell survival; (vii) ameliorate physiological symptoms associated with the cancerous condition; and/or (viii) prevent the occurrence of tumor.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy. The exact dose can be ascertained by one skilled in the art using known techniques. In general, the FN3 domain-targeting immune cells are administered at a dose of about $10^5$ to $10^8$ cells/kg body weight. According to some embodiments, the total dose of cells can be administered to the subject by dose fractionation, e.g., one, two, three or more separate administration of a partial dose.

According to particular embodiments, the compositions described herein are formulated to be suitable for the intended route of administration to a subject. For example, the compositions described herein can be formulated to be suitable for intravenous, subcutaneous, or intramuscular administration.

According to particular embodiments, a composition used in the treatment of a cancer can be used in combination with another treatment including, but not limited to, a chemotherapy, a lympho-depleting therapy, a radiation therapy, other immune-oncology drug, a targeted therapy, a cancer vaccine, or other anticancer drugs.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

In another general aspect, the invention relates to a method of redirecting immune cells to target their killing of FN3 domain binding cells in a subject in need thereof, comprising administering to the subject a pharmaceutical composition of the invention.

In another general aspect, the invention relates to a method of producing a pharmaceutical composition comprising FN3 domain-targeting immune cells of the invention, comprising combining FN3 domain-targeting immune cells with a pharmaceutically acceptable carrier to obtain the pharmaceutical composition.

The invention provides also the following non-limiting embodiments.

EMBODIMENTS

1. An isolated antibody, or antigen-binding fragment thereof, that specifically binds to a non-randomized region of a fibronectin type III (FN3) domain.
2. The isolated antibody, or an antigen-binding fragment of embodiment 1, comprising:
   a. a heavy chain CDR1 having the amino acid sequence of SEQ ID NO: 1, a heavy chain CDR2 having the amino acid sequence of SEQ ID NO: 4, a heavy chain CDR3 having the amino acid sequence of SEQ ID NO: 7, a light chain CDR1 having the amino acid sequence of SEQ ID NO: 9, a light chain CDR2 having the amino acid sequence of SEQ ID NO: 11, and a light chain CDR3 having the amino acid sequence of SEQ ID NO: 13;
   b. a heavy chain CDR1 having the amino acid sequence of SEQ ID NO: 2, a heavy chain CDR2 having the amino acid sequence of SEQ ID NO: 5, a heavy chain CDR3 having the amino acid sequence of SEQ ID NO: 8, a light chain CDR1 having the amino acid sequence of SEQ ID NO: 10, a light chain CDR2 having the amino acid sequence of SEQ ID NO: 12, and a light chain CDR3 having the amino acid sequence of SEQ ID NO: 13;
   c. a heavy chain CDR1 having the amino acid sequence of SEQ ID NO: 3, a heavy chain CDR2 having the amino acid sequence of SEQ ID NO: 6, a heavy chain CDR3 having the amino acid sequence of SEQ ID NO: 8, a light chain CDR1 having the amino acid sequence of SEQ ID NO: 10, a light chain CDR2 having the amino acid sequence of SEQ ID NO: 12, and a light chain CDR3 having the amino acid sequence of SEQ ID NO: 13;
   d. a heavy chain CDR1 having the amino acid sequence of SEQ ID NO: 35, a heavy chain CDR2 having the amino acid sequence of SEQ ID NO: 41, a heavy chain CDR3 having the amino acid sequence of SEQ ID NO: 44, a light chain CDR1 having the amino acid sequence of SEQ ID NO: 46, a light chain CDR2 having the amino acid sequence of SEQ ID NO: 48, and a light chain CDR3 having the amino acid sequence of SEQ ID NO: 50;
   e. a heavy chain CDR1 having the amino acid sequence of SEQ ID NO: 36, a heavy chain CDR2 having the amino acid sequence of SEQ ID NO: 42, a heavy chain CDR3 having the amino acid sequence of SEQ ID NO: 45, a light chain CDR1 having the amino acid sequence of SEQ ID NO: 47 a light chain CDR2 having the amino acid sequence of SEQ ID NO: 49, and a light chain CDR3 having the amino acid sequence of SEQ ID NO: 50;

f. a heavy chain CDR1 having the amino acid sequence of SEQ ID NO: 37, a heavy chain CDR2 having the amino acid sequence of SEQ ID NO: 43, a heavy chain CDR3 having the amino acid sequence of SEQ ID NO: 45, a light chain CDR1 having the amino acid sequence of SEQ ID NO: 47, a light chain CDR2 having the amino acid sequence of SEQ ID NO: 49, and a light chain CDR3 having the amino acid sequence of SEQ ID NO: 50;

g. a heavy chain CDR1 having the amino acid sequence of SEQ ID NO: 38, a heavy chain CDR2 having the amino acid sequence of SEQ ID NO: 51, a heavy chain CDR3 having the amino acid sequence of SEQ ID NO: 54, a light chain CDR1 having the amino acid sequence of SEQ ID NO: 56, a light chain CDR2 having the amino acid sequence of SEQ ID NO: 58, and a light chain CDR3 having the amino acid sequence of SEQ ID NO: 60;

h. a heavy chain CDR1 having the amino acid sequence of SEQ ID NO: 39, a heavy chain CDR2 having the amino acid sequence of SEQ ID NO: 52, a heavy chain CDR3 having the amino acid sequence of SEQ ID NO: 55, a light chain CDR1 having the amino acid sequence of SEQ ID NO: 57 a light chain CDR2 having the amino acid sequence of SEQ ID NO: 59, and a light chain CDR3 having the amino acid sequence of SEQ ID NO: 61; or i. a heavy chain CDR1 having the amino acid sequence of SEQ ID NO: 40, a heavy chain CDR2 having the amino acid sequence of SEQ ID NO: 53, a heavy chain CDR3 having the amino acid sequence of SEQ ID NO: 55, a light chain CDR1 having the amino acid sequence of SEQ ID NO: 57, a light chain CDR2 having the amino acid sequence of SEQ ID NO: 59, and a light chain CDR3 having the amino acid sequence of SEQ ID NO: 61.

3. The antibody or antigen-binding fragment of embodiment 1, wherein
   a. the variable heavy chain of the antibody comprises the amino acid sequence of SEQ ID NO: 14, and the variable light chain of the antibody comprises the amino acid sequence of SEQ ID NO:15;
   b. the variable heavy chain of the antibody comprises the amino acid sequence of SEQ ID NO: 74, and the variable light chain of the antibody comprises the amino acid sequence of SEQ ID NO:75; or
   c. the variable heavy chain of the antibody comprises the amino acid sequence of SEQ ID NO: 78, and the variable light chain of the antibody comprises the amino acid sequence of SEQ ID NO:79;

4. The antibody or antigen-binding fragment of embodiment 1, wherein
   a. the heavy chain of the antibody comprises the amino acid sequence of SEQ ID NO: 18 and light chain of the antibody comprises the amino acid sequence of SEQ ID NO: 19;
   b. the heavy chain of the antibody comprises the amino acid sequence of SEQ ID NO: 20 and light chain of the antibody comprises the amino acid sequence of SEQ ID NO: 21;
   c. the heavy chain of the antibody comprises the amino acid sequence of SEQ ID NO: 62 and light chain of the antibody comprises the amino acid sequence of SEQ ID NO: 63; or
   d. the heavy chain of the antibody comprises the amino acid sequence of SEQ ID NO: 64 and light chain of the antibody comprises the amino acid sequence of SEQ ID NO: 65.

5. The antigen binding fragment of any one of embodiments 1 to 4 wherein the antigen binding fragment is a Fab fragment, a Fab2 fragment, or a single chain antibody.

6. The antibody or antigen-binding fragment of any one of embodiments 1 to 5 wherein the antibody or antigen-binding fragment thereof is an IgG.

7. An isolated polynucleotide encoding the antibody or antigen-binding fragment of any one of embodiments 1 to 6.

8. A vector comprising the polynucleotide of embodiment 7

9. A host cell comprising the isolated polynucleotide of embodiment 7

10. A host cell comprising the vector of embodiment 8.

11. An isolated polynucleotide encoding a chimeric antigen receptor (CAR) comprising:
    (a) an extracellular domain comprising an scFv that specifically binds to a non-randomized region of an FN3 domain;
    (b) a transmembrane domain; and
    (c) an intracellular signaling domain, wherein the CAR optionally further comprises a hinge region connecting the extracellular domain and the transmembrane domain.

12. The isolated polynucleotide of embodiment 11, wherein the CAR comprises:
    (a) an extracellular domain comprising an scFv having an amino acid sequence that is at least 90% identical to one of SEQ ID NOs: 68-73;
    (b) a hinge region comprising an amino acid sequence that is at least 90% identical to SEQ ID NO: 24;
    (c) a transmembrane domain comprising an amino acid sequence that is at least 90% identical to SEQ ID NO: 25; and
    (d) an intracellular signaling domain comprising a co-stimulatory domain having an amino acid sequence that is at least 90% identical to SEQ ID NO: 26, and a primary signaling domain having an amino acid sequence that is at least 90% identical to SEQ ID NO: 27.

13. The isolated polynucleotide of embodiment 12, wherein:
    (a) the extracellular domain comprises the amino acid sequence of one of SEQ ID NOs: 68-73;
    (b) the hinge region comprises the amino acid sequence of SEQ ID NO: 24;
    (c) the transmembrane domain comprises the amino acid sequence of SEQ ID NO: 25; and
    (d) the intracellular signaling domain comprises the amino acid sequence of SEQ ID NO: 26 and the amino acid sequence of SEQ ID NO: 27.

14. A vector comprising the polynucleotide of any of embodiments 11-13.

15. A host cell comprising the polynucleotide of any of embodiments 11-13.

16. A host cell comprising the vector of embodiment 14.
17. A chimeric antigen receptor (CAR) comprising:
   (a) an extracellular domain comprising an scFv that specifically binds to a non-randomized region of an FN3 domain;
   (b) a transmembrane domain; and
   (c) an intracellular signaling domain, wherein the CAR optionally further comprises a hinge region connecting the extracellular domain and the transmembrane domain.
18. The CAR of embodiment 16, comprising:
   (a) an extracellular domain comprising an scFv having an amino acid sequence that is at least 90% identical to one of SEQ ID NOs: 68-73;
   (b) a hinge region comprising an amino acid sequence that is at least 90% identical to SEQ ID NO: 24;
   (c) a transmembrane domain comprising an amino acid sequence that is at least 90% identical to SEQ ID NO: 25; and
   (d) an intracellular signaling domain comprising a co-stimulatory domain having an amino acid sequence that is at least 90% identical to SEQ ID NO: 26, and a primary signaling domain having an amino acid sequence that is at least 90% identical to SEQ ID NO: 27.
19. The CAR of embodiment 17, wherein:
   (a) the extracellular domain comprises the amino acid sequence of one of SEQ ID NOs: 68-73;
   (b) the hinge region comprises the amino acid sequence of SEQ ID NO: 24;
   (c) the transmembrane domain comprises the amino acid sequence of SEQ ID NO: 25; and
   (d) the intracellular signaling domain comprises the amino acid sequence of SEQ ID NO: 26 and the amino acid sequence of SEQ ID NO: 27.

EXAMPLES

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

Example 1: Immunization of Rabbits to Generate Anti-Fn3 Domain Antibodies

Rabbit monoclonal antibody generation was performed using the Tencon25 antigen (SEQ ID NO: 28).

LPAPKNLVVSEVTEDSARLSWTAPDAAFDSFLIQYQESEKVGEAIVLTV

PGSERSYDLTGLKPGTEYTVSIYGVKGGHRSNPLSAIFTT

Animals:
3 months old New Zealand white rabbits with IDs E4831 and E4832 and immunization was performed.
Immunization Protocol:
Rabbits were immunized using standard protocol of five injections and two test bleeds per rabbit. At the time of each injection, the antigen aliquot was thawed and combined with Complete Freund's Adjuvant (CFA) (for the first injection) or with incomplete Freund's Adjuvant (IFA) for the subsequently injections. The injection route was subcutaneous (SC). The immunization details are summarized in Table 3:

TABLE 3

Rabbit Immunization Details

| Antigen ID | Rabbit ID | Type | number | amount | Note |
|---|---|---|---|---|---|
| Tencon25 | E4831 | Bleed | 0 | 5 ml | |
| | | Injection | 1 | 0.4 | |
| | | Injection | 2 | 0.2 | |
| | | Injection | 3 | 0.2 | |
| | | Bleed | 1 | 5 ml | |
| | | Injection | 4 | 0.2 | |
| | | Bleed | 2 | 5 ml | |
| Tencon25 | E4832 | Bleed | 0 | 5 ml | |
| | | Injection | 1 | 0.4 | |
| | | Injection | 2 | 0.2 | |
| | | Injection | 3 | 0.2 | |
| | | Bleed | 1 | 5 ml | |
| | | Injection | 4 | 0.2 | |
| | | Bleed | 2 | 5 ml | |
| | | Injection | 5 | 0.4 | |

ELISA Titer Examination:

The serum titer against Tencon25 as well as the counter screening antigens Tencon28 (SEQ ID NO: 29) and P114-83 (SEQ ID NO: 30) was evaluated using test bleeds 1 and 2 with Epitomics, Inc. standard protocols. In conclusion, both rabbits had good immune response against the immunogen and had met the standard cut-off for splenectomy (O.D.>0.3 at 1:64K dilution). Rabbit E4832 was chosen as the candidate for splenectomy and monoclonal fusion.

Splenectomy:

IV boost was administered to rabbit E4832, followed by splenectomy The spleen was delivered and splenocytes were isolated, according to Epitomics' standard procedure (Table 3).

TABLE 4

Details of Splenocyte Isolation

| Antigen id | Rabbit id | Tissue type | Weight (g) | Size (cm) | Viability (%) | Total Cells in Mil |
|---|---|---|---|---|---|---|
| Tencon25 | E4832 | Spleen | 2.14 | 6 | 80 | 1300 |

Fusion:

Two hundred million lymphocyte cells were fused with 100 million fusion partner cells and plated on 20×96-well plates respectively (Table 4). The plates were kept in tissue culture incubators under standard conditions.

TABLE 5

Fusion Information

| Antigen ID | Fusion Code | Fusion date | # of Plates | Fusion Efficiency (%) |
|---|---|---|---|---|
| CEN-11 | F1 | Aug. 10, 2011 | 20 | 46 |
| CEN-11 | F2 | Aug. 11, 2011 | 20 | 59 |

Cell growth was examined 2-3 weeks after fusion and fusion efficiency computed using the number of wells with growth divided by the total number of wells examined. A minimum of two plates were examined for each fusion.

The screening process is summarized below:

Pre-screen: plates #5 & #25;

Primary screen: the remaining 38 plates;

Screen method: standard ELISA, plates coated with 50 ng of Tencon25/well;

Positive control: bleed 2 of E4832 at 1:10K dilution;

Results: 158 clones with O.D. greater than 0.5 were considered putatively positive and were further expanded to 24-well plate;

Confirmatory screen: plates coated with 50 ng of Tencon25/well or coated with 50 ng of Tencon28 or P114-83.

Results: 151 clones were confirmed positive against Tencon25. Among them, 78 were Tencon25 specific as they are Tencon28 negative.

Example 2: Selection of Anti-Fn3 Domain Antibodies

Production:

Clone supernatant was evaluated for binding to all centyrins and no binding to negative control protein. From this evaluation, one clone, CEN-25-105-5, was picked for production. The hybridoma cells were cultured and adapted into serum-free medium and inoculated into 1 L integra flasks. After harvesting, the antibodies were purified using protein A resins and QCed. Yield was 20 mg for CEN-25-105-5.

TABLE 6

CDR amino acid sequences of CEN-25-105-5
(SEQ ID NO:)

| Delineation | HC-CDR1 | HC-CDR2 | HC-CDR3 | LC-CDR1 | LC-CDR2 | LC-CDR3 |
|---|---|---|---|---|---|---|
| IMGT | GIDLSTSV (1) | IYTNVNT (4) | ARAVYAGAM DL (7) | ERIYSN (9) | KAS (11) | QYTSYGSGY VGT (13) |
| Kabat | TSVMG (2) | FIYTNVNTYYASWAK G (5) | AVYAGAMDL (8) | QASERIYSNLA (10) | KASTLAS (12) | QYTSYGSGY VGT (13) |
| Chothia | GIDLSTS (3) | YTNVN (6) | AVYAGAMDL (8) | QASERIYSNLA (10) | KASTLAS (12) | QYTSYGSGY VGT (13) |

VH and VL of CEN-25-105-5 is shown below in Table 7.

TABLE 7

Variable heavy chain and variable light chain sequences of CEN-25-105-5
Variable regions of heavy chain and light chains for CEN-25-105-5
were cloned into rat and mouse IgGK expression vectors for
expression and characterization. CEN-25-

| Sequence type | VH Sequence | SEQ ID NO: | VL Sequence | SEQ ID NO: |
|---|---|---|---|---|
| Amino acid | QSLEESGGRLVTPGTP LTLTCTVSGIDLSTSV MGWVRQAPGKGLES IGFIYTNVNTYYASW AKGRFTISRTSTTVDL KITSPTTGDTATYFCA RAVYAGAMDLWGQ GTLVTVSS | 14 | DVVMTQTPASVSGPV GGTVTIKCQASERIYSN LAWYQQKPGQPPKLLI YKASTLASGVSSRFKG SGSGTEFTLTIRDLECA DAATYSCQYTSYGSG YVGTFGGGTEVVVEG | 15 |
| DNA | Ctggaggagtccgggggtcgcc tggtcacgcctgggacaccctg acactcacctgcacagtctctgga atcgacctcagtacctctgtcatg ggttgggtccgccaggctccagg gaaggggctggaatccatcggat tcatttatactaatgttaacacatac tacgcgagctgggcaaaaggcc gattcaccatctccagaacctcga ccacggtggatctgaaaatcacc agtccgacaaccggggacacgg ccacctatttctgtgccagagctgt ttatgctggtgctatggacttgtgg ggccaaggcaccctggtcaccgt ctcctca | 16 | gatgttgtgatgacccagactccag cctccgtgtctggacctgtgggagg cacagtcaccatcaagtgccaggc cagtgagagaatttatagcaatttag cctggtatcagcagaaaccagggc agcctcccaaactcctgatctacaa ggcatccactctggcatctggggtc tcatcgcggttcaaaggcagtggat ctgggacagagttcactctcaccat cagggaccttgagtgtgccgatgct gccacttactcctgtcaatatacttctt atggcagtggttatgttggtactttcg gcggagggaccgaggtggtggtc gaaggt | 17 |

105-5 is now referred to as AS7B91 as a mouse IgG2a kappa antibody and AS7B90 as the rat IgG1 kappa antibody. AS7B16 and AS7B82 were also generated from mouse and rabbit V regions, respectively. Tables 8 and 9 show the sequences of the CDRs and the sequences of the V regions of AS7B16 and AS7B82. The heavy chain and light chain sequences for all antibodies are shown below in Table 10.

TABLE 8

CDR amino acid sequences of AS7B16 and AS7B82

| Delineation | HC-CDR1 | HC-CDR2 | HC-CDR3 | LC-CDR1 | LC-CDR2 | LC-CDR3 |
|---|---|---|---|---|---|---|
| AS7B16 | | | | | | |
| IMGT | GFSLNTSGTG (35) | IWWDDDK (41) | VRIKGRMDY (44) | QSVLFGSKQKNY (46) | WAS (48) | HQYLSLFT (50) |
| Kabat | TSGTGVG (36) | HIWWDDDKGYNPALKS (42) | IKGRMDY (45) | KSSQSVLFGSKQKNYLA (47) | WASTRES (49) | HQYLSLFT (50) |
| Chothia | GFSLNTSGT (37) | WWDDD (43) | IKGRMDY (45) | KSSQSVLFGSKQKNYLA (47) | WASTRES (49) | HQYLSLFT (50) |
| AS7B82 | | | | | | |
| IMGT | GIDFSSVAY (38) | IYAGSSSSI (51) | ARGLFTSGSGYYIDM (54) | QSIGSD (56) | SAS (58) | QCTYSSSTGYNA (60) |
| Kabat | SVAYMC (39) | CIYAGSSSSIYYASWAKG (52) | GLFTSGSGYYIDM (55) | QASQSIGSNLA (57) | GASNLAA (59) | QRGYISSAVDFFV (61) |
| Chothia | GIDFSSVA (40) | YAGSSSS (53) | GLFTSGSGYYIDM (55) | QASQSIGSNLA (57) | GASNLAA (59) | QRGYISSAVDFFV (61) |

TABLE 9

Variable heavy chain and variable light chain sequences of AS7B16 and AS7B82

| Sequence type | VH Sequence | SEQ ID NO: | VL Sequence | SEQ ID NO: |
|---|---|---|---|---|
| Amino acid AS7B16 | QVTLKESGPGILQPSQ TLSLTCSFSGFSLNTS GTGVGWIRQPSGKGL EWLAHIWWDDDKGY NPALKSRLTISKNTSS NLVFLKIASVDTADT ATYYCVRIKGRMDY WGQGTSVTSS | 74 | NIMMTQSPSSLAVSAG EKVTMNCKSSQSVLFG SKQKNYLAWYQQKPG QSPKLLIYWASTRESG VPDRFTGSGSGTDFILT ISNVQAEDLAVYYCHQ YLSLFTFGSGTKLEIK | 75 |
| DNA AS7B16 | AGGTTACTCTGAAA GAGTCTGGCCCTGG GATATTGCAGCCCTC CCAGACCCTCAGTCT GACTTGTTCTTTCTC TGGGTTTTCACTGGA CACTTCTGGTACGGG TGTAGGCTGGATTCG TCAGCCTTCAGGGA AGGGTCTGGAGTGG CTGGCACACATTTGG TGGGATGATGACAA GGGGTATAACCCAG CCCTGAAGAGCCGA CTGACAATCTCCAA AAACACCTCCAGCA ACCTGGTATTCCTCA AGATCGCCAGTGTG GACACTGCAGATAC TGCCACATATTACTG | 76 | AACATTATGATGACA CAGTCGCCATCCTCTC TGGCTGTGTCTGCAG GAGAAAGGTCACTA TGAACTGTAAGTCCA GTCAAAGTGTTTTATT CGGTTCAAAACAGAA GAACTATTTGGCCTG GTACCAGCAGAAACC AGGGCAGTCTCCTAA ATTGCTGATCTACTGG GCATCCACTAGGGAA TCTGGTGTCCCTGATC GCTTCACAGGCAGTG GATCTGGGACAGATT TTATACTTACCATCAG CAATGTACAAGCTGA AGACCTGGCAGTTTA TTACTGTCATCAATAC CTCTCCCTATTCACGT | 77 |
| Amino acid AS7B82 | QEQQKESGGGLVKPG ASLTLTCTASGIDFSS VAYMCWVRQAPGK GLEWIACIYAGSSSSI YYASWAKGRFTVSR TSSTTVTLQMTSLTA ADTATYFCARGLFTS GSGYYIDMWGPGTL VTVSS | 78 | DVVMTQTPSSVEVAV GGTVTIKCQASQSIGSN LAWYQQKPGQRPKLLI YGASNLAAGVPSRFSG SGSGTQFTLTISDVECA DAATYYCQRGYISSAV DFFVFGGGTEVVVKG | 79 |
| DNA AS7B82 | CAGGAGCAGCAGAA GGAGTCCGGGGGAG GCCTGGTCAAGCCT GGGGCATCCCTGAC ACTCACCTGCACAG CTTCTGGAATCGACT TCAGTAGTGTCGCCT ACATGTGTTGGGTCC GCCAGGCTCCAGGG AAGGGGCTGGAGTG GATCGCATGCATTTA TGCTGGTAGTAGTA GTAGCATCTACTACG CGAGCTGGGCGAAA GGCCGATTCACCGTC TCCAGAACCTCGTCT ACCACGGTGACTCT | 80 | GATGTCGTGATGACC CAGACTCCATCCTCTG TGGAGGTAGCTGTGG GAGGCACAGTCACCA TCAAGTGCCAGGCCA GTCAGAGCATTGGTA GTAATTTAGCCTGGT ATCAGCAGAAACCAG GGCAGCGTCCCAAGC TCCTGATCTATGGTGC ATCCAATCTGGCCGC TGGGGTCCCATCGCG GTTCAGTGGCAGTGG ATCTGGGACACAGTT CACTCTCACCATCAG CGACGTGGAGTGTGC CGATGCTGCCCTTA | 81 |

TABLE 9-continued

Variable heavy chain and variable light chain sequences of AS7B16 and AS7B82

| Sequence type | VH Sequence | SEQ ID NO: | VL Sequence | SEQ ID NO: |
|---|---|---|---|---|
| | GCAAATGACCAGTC TGACAGCCGCGGAC ACGGCCACCTATTTC TGTGCGAGAGGTCT ATTTACTAGTGGTAG TGGATATTATATAGA CATGTGGGGCCCAG GCACCCTGGTCACC GTCTCCTCA | | CTACTGTCAACGGGG TTATATTAGCAGTGCT GTTGATTTTTTTGTTT TCGGCGAGGGACCG AGGTGGTGGTCAAAG GT | |

TABLE 10

Heavy chain and light chain sequences of AS7B91

| Clone | Heavy Chain Amino Acid Sequence | SEQ ID NO: | Light Chain Amino Acid Sequence | SEQ ID NO: |
|---|---|---|---|---|
| AS7B91 | QSLEESGGRLVTPGTP LTLTCTVSGIDLSTSVM GWVRQAPGKGLESIGF IYTNVNTYYASWAKG RFTISRTSTTVDLKITSP TTGDTATYFCARAVY AGAMDLWGQGTLVT VSSAKTTAPSVYPLAP VCGDTTGSSVTLGCLV KGYFPEPVTLTWNSGS LSSGVHTFPAVLQSDL YTLSSSVTVTSSTWPS QSITCNVAHPASSTKV DKKIEPRGPTIKPCPPC KCPAPNLLGGPSVFIFP PKIKDVLMISLSPIVTC VVVDVSEDDPDVQIS WFVNNVEVHTAQTQT HREDYNSTLRVVSALP IQHQDWMSGKEFKCK VNNKDLPAPIERTISKP KGSVRAPQVYVLPPPE EEMTKKQVTLTCMVT DFMPEDIYVEWTNNG KTELNYKNTEPVLDSD GSYFMYSKLRVEKKN WVERNSYSCSVVHEG LHNHHTTKSFSRTPGK | 18 | DVVMTQTPASVSGPV GGTVTIKCQASERIYSN LAWYQQKPGQPPKLLI YKASTLASGVSSRFKG SGSGTEFTLTIRDLECA DAATYSCQYTSYGSG YVGTFGGGTEVVVEG RADAAPTVSIFPPSSEQ LTSGGASVVCFLNNFY PKDINVKWKIDGSERQ NGVLNSWTDQDSKDS TYSMSSTLTLTKDEYE RHNSYTCEATHKTSTS PIVKSFNRNEC | 19 |
| AS7B90 | QSLEESGGRLVTPGTP LTLTCTVSGIDLSTSVM GWVRQAPGKGLESIGF IYTNVNTYYASWAKG RFTISRTSTTVDLKITSP TTGDTATYFCARAVY AGAMDLWGQGTLVT VSSAETTAPSVYPLAP GTALKSNSMVTLGCL VKGYFPEPVTVTWNS GALSSGVHTFPAVLQS GLYTLTSSVTVPSSTW PSQTVTCNVAHPASST KVDKKIVPRNCGGDC KPCICTGSEVSSVFIFPP KPKDVLTITLTPKVTC VVVDISQDDPEVHFSW FVDDVEVHTAQTRPPE EQFNSTFRSVSELPILH QDWLNGRTFRCKVTS AAFPSPIEKTISKPEGRT QVPHVYTMSPTKEEM TQNEVSITCMVKGFYP | 20 | DVVMTQTPASVSGPV GGTVTIKCQASERIYSN LAWYQQKPGQPPKLLI YKASTLASGVSSRFKG SGSGTEFTLTIRDLECA DAATYSCQYTSYGSG YVGTFGGGTEVVVEG RADAAPTVSIFPPSSEQ LASGGASVVCFINKFY PKDISVKWKIDGSERQ NDVLNSVTDQDSKDST YSMSSTLTLTKADYER HNLYTCEVVHKTSASP VVKSFNRNEC | 21 |

TABLE 10-continued

Heavy chain and light chain sequences of AS7B91

| Clone | Heavy Chain Amino Acid Sequence | SEQ ID NO: | Light Chain Amino Acid Sequence | SEQ ID NO: |
|---|---|---|---|---|
| | PDIYVEWQMNGQPQE NYKNTPPTMDTDGSYF LYSKLNVKKEKWQQG NTFTCSVLHEGLHNHH TEKSLSHSPGK | | | |
| AS7B16 | QVTLKESGPGILQPSQT LSLTCSFSGFSLNTSGT GVGWIRQPSGKGLEW LAHIWWDDDKGYNPA LKSRLTISKNTSSNLVF LKIASVDTADTATYYC VRIKGRMDYWQGTS VTVSSKTTPPSVYPLAP GSAAQTNSMVTLGCL VKGYFPEPVTVTWNS GSLSSGVHTFPPAVLES DLYTLSSSVTVPSSPRP SETVTCNVAHPASSTK VDKKIVPRDCGCKPCI CTVPEVSSVFIFPPPKPK DVLTITLTPKVTCVVV DISKDDPEVQFSWFVD DVEVHTAQTQPREEQF NSTFRSVSELPIMHQD WLNGKEFKCRVNSAA FPAPIEKTISKTKGRPK APQVYTIPPPKEQMAK DKVSLTCMITDFFPEDI TVEWQWNGQPAENY KNTQPIMNTNGSYFVY SKLNVQKSNWEAGNT FTCSVLHEGLHNHHTE KSLSHSPGK | 62 | NIMMTQSPSSLAVSAG EKVTMNCKSSQSVLFG SKQKNYLAWYQQKPG QSPKLLIYWASTRESG VPDRFTGSGSGTDFILT ISNVQAEDLAVYYCHQ YLSLFTFGSGTKLEIKR ADAAPTVSIFPPSSEQL TSGGASVVCFLNNFYP KDINVKWKIDGSERQN GVLNSWTDQDSKDST YSMSSTLTLTKDEYER HNSYTCEATHKTSTSPI VKSFNRNEC | 63 |
| AS7B82 | QEQQKESGGGLVKPG ASLTLTCTASGIDFSSV AYMCWVRQAPGKGLE WIACIYAGSSSSIYYAS WAKGRFTVSRTSSTTV TLQMTSLTAADTATYF CARGLFTSGSGYYIDM WGPGTLVTVSSASTKG PSVFPLAPSSKSTSGGT AALGCLVKDYFPEPVT VSWNSGALTSGVHTFP AVLQSSGLYSLSSVVT VPSSSLGTQTYICNVN HKPSNTKVDKKVEPKS CDKTHTCPPCPAPELL GGPSVFLFPPKPKDTL MISRTPEVTCVVVDVS HEDPEVKFNWYVDGV EVHNAKTKPREEQYNS TYRVVSVLTVLHQDW LNGKEYKCKVSNKAL PAPIEKTISKAKGQPRE PQVYTLPPSRDELTKN QVSLTCLVKGFYPSDI AVEWESNGQPENNYK TTPPVLDSDGSFFLYSK LTVDKSRWQQGNVFS CSVMHEALHNHYTQK SLSLSPGK | 64 | DVVMTQTPSSVEVAV GGTVTIKCQASQSIGSN LAWYQQKPGQRPKLLI YGASNLAAGVPSRFSG SGSGTQFTLTISDVECA DAATYYCQRGYISSAV DFFVGGGTEVVVKG RTVAAPSVIFPPSDEQ LKSGTASVVCLLNNFY PREAKVQWKVDNALQ SGNSQESVTEQDSKDS TYSLSSTLTLSKADYE KHKVYACEVTHQGLS SPVTKSFNRGEC | 65 |

Figure 1B:
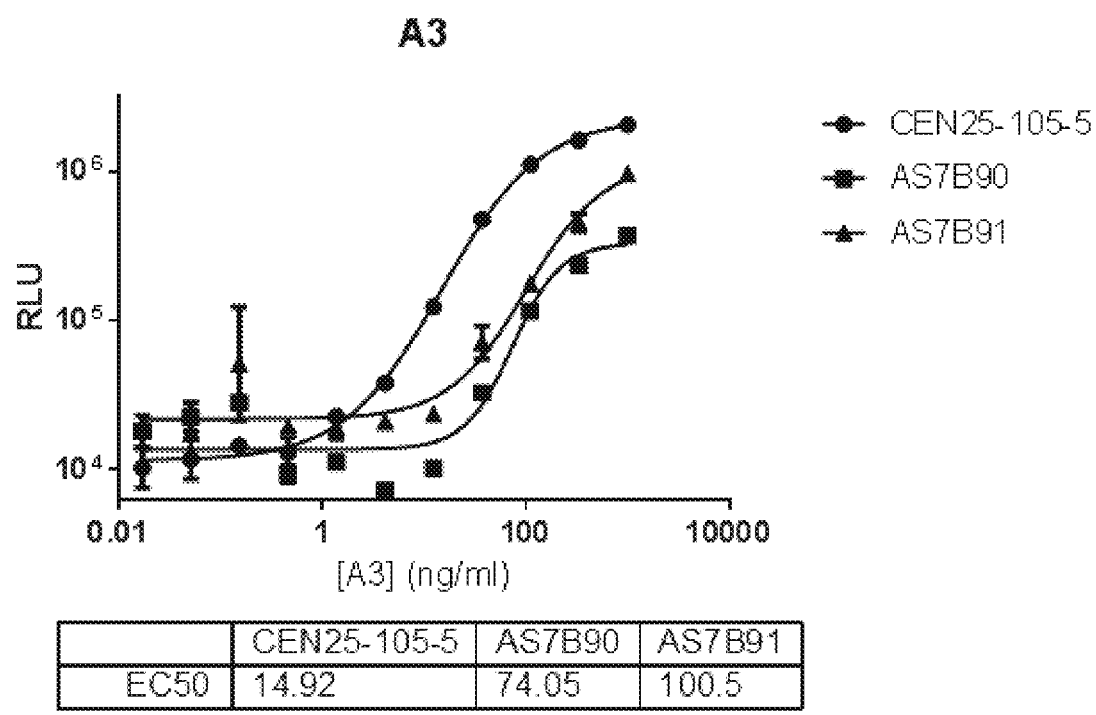
Figure 1C:
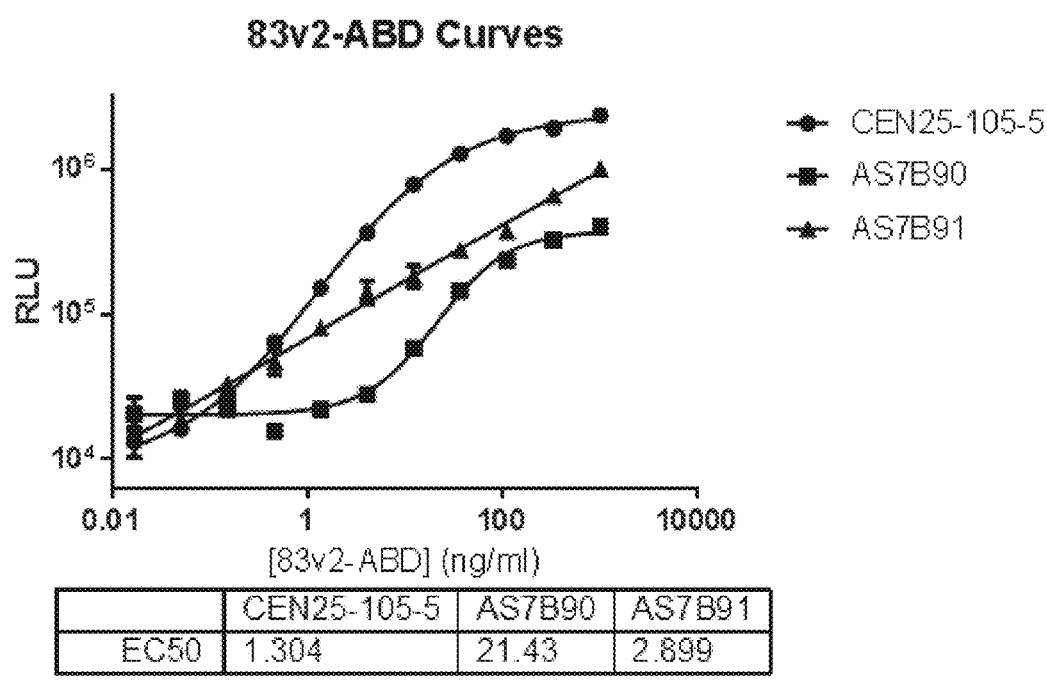

Example 3: Binding of Recombinant AS7B90 and AS7B91 to Fn3 Domains as Compared to Original CEN-25-105-5 Rabbit Antibody Supernatants for AS7B90 and AS7B91, which are the rat and mouse chimeras, respectively of CEN-25-105-5 were evaluated for their ability to bind recombinant FN3 domains by ELISA. Three plates were coated with dose-response curves of, FN3 domain A3 specific for human cMET (SEQ ID NO: 31), 83v2-ABD specific for human EGFR with an albumin binding domain (SEQ ID NO: 32), tencon 25 that has no specificity (SEQ ID NO: 28), or negative control protein, all at 50 μL/well in 50 mM PBS. Plates were incubated over night at 4° C. Supernatants were dumped from plates and 200 μL/well Superblock was added to block plates for 1 hour at RT. Plates were washed 3× with TBS-T. Supernatants and CEN25-105-5 were prepared at 1 μg/ml in Superblock and added to the plates. Plates were incubated for 1 hour at RT. Plates were washed 3× with TBS-T. Secondary antibodies (HRP-goat anti-rabbit, rat or mouse) were prepared at 1:10,000 in Superblock and added to the plates. Plates were incubated for 1 hour at RT. Plates were washed 3× with TBS-T. 50 μL/well POD reagent (prepared according to Sigma-Aldrich manufacturer's instructions and incubated in the dark at RT for at least 30 minutes prior to use) was added to plates. After 3-5 minute incubation, protected from light, the M5 was used to read luminescence. The results were plotted in Prism (FIGS. 1A-C) using a Log/Log transformation, and then a four-parameter curve fit. As shown in FIGS. 1A-C, both AS7B90 and AS7B91 showed specificity to the three different FN3 domains, confirming that the binding epitope of these anti FN3 domain antibodies are specific to the conserved framework regions of the, and not the variable loops which render FN3 domain specificity. It should be noted that there was no non-specific binding to negative control antibody. The mouse version of the antibody, AS7B91, appeared to have binding characteristics more similar to the original rabbit hybridoma antibody.

Example 4: Testing AS7B91 for Detection of Anti-BCMA Cartyrins Expressed on the Surface of Primary T Cells 100 μl per well were plated of 1×10$^6$ anti-BCMA CAR-Tyrin T cells/ml. Wells were washed 2× with PBS. eFlour 506 Fixable Viability Dye was added to samples at a 1:2000 final concentration for LIVE-DEAD sample staining and allowed to incubate for 30 minutes at 4° C. Staining reaction was quenched with FACS buffer, and samples were washed two times with FACS buffer. Fc Block was added (33 μl Fc/ml FACS) for 10 minutes at room temperature. 100 μl of primary AS7B91, FACS buffer, or isotype control were added and incubated 20 minutes on ice. Samples were then washed one time with FACS buffer. Secondary antibody was added and incubated for 20 minutes on ice (Anti-Mouse IgG-AF647 used at 1:50 for final concentration of 10 μg/ml). After secondary antibody incubation, wells were washed one time with FACS buffer followed by one time with PBS. After washing, samples were fixed in 2% PFA for 10 minutes at room temperature. Samples were washed and resuspended in FACS buffer.

As shown in FIG. 2, the recombinant AS7B91 was able to detect the expression of CARTyrins on the surface of primary T cells and can thus be used as a general CARTyrin detection reagent. In a homogeneous population of CAR-Tyrin expressing T cells, the AS7B91 antibody could be used to quantitate the number of CARTyrins on the surface of the cells.

Example 5: Use of AS7B91 to Activate T Cell-Expressing Cartyrins

Since the CARTyrins are attached to T cell signaling domains, the binding and clustering of these CARTyrins by the AS7B91 antibody could result in activation of those signaling domains and the activation of the T cells expressing them. To test this, primary T cells expressing CARTyrins were incubated with AS7B91 or anti-CD3 antibody, that is known to induce activation. Briefly, 12 different BCMA RNA-expressing CARTyrin clones were electroporated in primary pan T cells derived from normal human blood (Normal Blood Donor Service—TSRI) using the ECM 830 Square Wave Electroporation System (BTX). 5×10$^6$ pan T-cells received a single electric pulse (500V, 750 us) per the manufacturer's protocol, either with or without 10 μg of BCMA-targeting CAR mRNA. Surface expression of CARs was assessed 24 hours later using a polyclonal anti-FN3 domain Ab. AS7B91 or an anti-CD3 antibody were plated both at 5 μg/ml in the presence of a soluble anti-CD28 antibody (2 ug/ml). Cells and supernatants were harvested on day 2 and day 6 post stimulation. Cells were Stained for T cell subset markers (CD4, 8), activation markers (CD25, 69, 71, 137, HLA-DR) and Fixable Viability Dye. Cells gated Live (FVD negative)->doublet exclusion->CD4 or CD8 single positive->CD4s and CD8s assessed for activation marker expression individually. LSR Voltages set based on antibody conjugated beads and single color controls. Gates were set based on Fluorescence Minus One (FMO) and isotype controls As seen in Table 11, the AS7B91 monoclonal anti-FN3 domain antibody is able to stimulate CARTyrin+primary panT cells in the presence of co-stimulation through CD28 (analogous to anti-CD3/CD28 procedures). This activation is dependent on CARTyrin expression, and is not as robust or as long lived as that observed with anti-CD3. In addition, treatment with the AS7B91 and anti-CD28 results in an 11-fold increase in cell number compared to unstimulated cells. In summary, the anti-FN3 domain antibody can induce T cell proliferation and activation of cells expressing CAR-Tyrins.

TABLE 11

Activation of CARTyrin expressing pan T cells using the anti-centryin antibody AS7B91 in conjunction with anti-CD28 co-stimulation. Compared to unstimulated control cells expressing, pos = positive staining (neg in unstim), hi = high level of staining, lo = low level of staining (neg in unstim), neg = no staining.

| | Day 2 | | | | | |
|---|---|---|---|---|---|---|
| | CD25 | DR | CD71 | CD69 | CD137 | |
| CD8 | pos | hi | hi | lo | neg | a-Centyrin |
| | pos | hi | hi | pos | pos | a-CD3 |

Example 6: Engineering of AS7B91 into a scFv Chimeric Antigen Receptor

To generate a CAR construct of the AS7B91, AS7B16, and AS7B82 antibodies, the variable regions were constructed into scFvs. For AS7B91, scFvs were generated in two different orientations: HCv-LCv, or LCv-HCv.

AS7B91 H-L scFv (SEQ ID NO: 22)
METGLRWLLLVAVLKGVQCQSLEESGGRLVTPGTPLTLTCTVSGIDLSTS

VMGWVRQAPGKGLESIGFIYTNVNTYYASWAKGRFTISRTSTTVDLKITS

PTTGDTATYFCARAVYAGAMDLWGQGTLVTVSSGGGGSGGGGSGGGGSGG

-continued

GGSDVVMTQTPASVSGPVGGTVTIKCQASERIYSNLAWYQQKPGQPPKLL

IYKASTLASGVSSRFKGSGSGTEFTLTIRDLECADAATYSCQYTSYGSGY

VGTFGGGTEVVVEG

AS7B91 L-H scFv
(SEQ ID NO: 23)
MDTRAPTQLLGLLLLWLPGARCDVVMTQTPASVSGPVGGTVTIKCQASER

IYSNLAWYQQKPGQPPKLLIYKASTLASGVSSRFKGSGSGTEFTLTIRDL

ECADAATYSCQYTSYGSGYVGTFGGGTEVVVEGGGGGSGGGGSGGGGSGG

GGSLEESGGRLVTPGTPLTLTCTVSGIDLSTSVMGWVRQAPGKGLESIGF

IYTNVNTYYASWAKGRFTISRTSTTVDLKITSPTTGDTATYFCARAVYAG

AMDLWGQGTLVTVSS

AS7B16 H-L scFv
(SEQ ID NO: 66)
QVTLKESGPGILQPSQTLSLTCSFSGFSLNTSGTGVGWIRQPSGKGLEWL

AHIWWDDDKGYNPALKSRLTISKNTSSNLVFLKIASVDTADTATYYCVRI

KGRMDYWGQGTSVTVSSGGGGSGGGGSGGGGSGGGGSNIMMTQSPSSLAV

SAGEKVTMNCKSSQSVLFGSKQKNYLAWYQQKPGQSPKLLIYWASTRESG

VPDRFTGSGSGTDFILTISNVQAEDLAVYYCHQYLSLFTFGSGTKLEIK

AS7B16 L-H scFv
(SEQ ID NO: 82)
NIMMTQSPSSLAVSAGEKVTMNCKSSQSVLFGSKQKNYLAWYQQKPGQSP

KLLIYWASTRESGVPDRFTGSGSGTDFILTISNVQAEDLAVYYCHQYLSL

FTFGSGTKLEIKGGGGSGGGGSGGGGSGGGGSQVTLKESGPGILQPSQTL

SLTCSFSGFSLNTSGTGVGWIRQPSGKGLEWLAHIWWDDDKGYNPALKSR

LTISKNTSSNLVFLKIASVDTADTATYYCVRIKGRMDYWGQGTSVTVSS

AS7B82 H-L scFv
(SEQ ID NO: 67)
QEQQKESGGGLVKPGASLTLTCTASGIDFSSVAYMCWVRQAPGKGLEWIA

CIYAGSSSSIYYASWAKGRFTVSRTSSTTVTLQMTSLTAADTATYFCARG

LFTSGSGYYIDMWGPGTLVTVSSGGGGSGGGGSGGGGSGGGGSDVVMTQ

TPSSVEVAVGGTVTIKCQASQSIGSNLAWYQQKPGQRPKLLIYGASNLAA

GVPSRFSGSGSGTQFTLTISDVECADAATYYCQRGYISSAVDFFVFGGGT

EVVVKG

AS7B82 L-H scFv
(SEQ ID NO: 83)
DVVMTQTPSSVEVAVGGTVTIKCQASQSIGSNLAWYQQKPGQRPKLLIYG

ASNLAAGVPSRFSGSGSGTQFTLTISDVECADAATYYCQRGYISSAVDFF

VFGGGTEVVVKGGGGGSGGGGSGGGGSGGGGSQEQQKESGGGLVKPGAS

LTLTCTASGIDFSSVAYMCWVRQAPGKGLEWIACIYAGSSSSIYYASWAK

GRFTVSRTSSTTVTLQMTSLTAADTATYFCARGLFTSGSGYYIDMWGPGT

LVTVSS

The amino acid sequence of the different scFv sequences were back-translated and engineered with hinge sequence, TM domain, and signaling domains. The completed construct was cloned into a T7 in vitro transcription vector to generate mRNA using the commercially available mMESSAGE mMACHINE® T7 ULTRA Transcription Kit. The amino acid sequences for the components of the CAR constructs were as shown in Table 12:

TABLE 12

Amino Acid Sequence of the two different AS7B91, AS7B16 and AS7B82 CAR constructs (H-L orientation and L-H orientation).

| Domain | Sequence |
|---|---|
| Extracellular AS7B91 | SEQ ID NO: 72 (H-L orientation)<br>QSLEESGGRLVTPGTPLTLTCTVSGIDLSTSVMGWVRQAPG<br>KGLESIGFIYTNVNTYYASWAKGRFTISRTSTTVDLKITSPTT<br>GDTATYFCARAVYAGAMDLWGQGTLVTVSSGGGGSGGGG<br>SGGGGSGGGGSDVVMTQTPASVSGPVGGTVTIKCQASERIY<br>SNLAWYQQKPGQPPKLLIYKASTLASGVSSRFKGSGSGTEF<br>TLTIRDLECADAATYSCQYTSYGSGYVGTFGGGTEVVVEG<br>SEQ ID NO: 73 (L-H orientation)<br>DVVMTQTPASVSGPVGGTVTIKCQASERIYSNLAWYQQKP<br>GQPPKLLIYKASTLASGVSSRFKGSGSGTEFTLTIRDLECADA<br>ATYSCQYTSYGSGYVGTFGGGTEVVVEGGGGGSGGGGSGG<br>GGSGGGGSLEESGGRLVTPGTPLTLTCTVSGIDLSTSVMGW<br>VRQAPGKGLESIGFIYTNVNTYYASWAKGRFTISRTSTTVDL<br>KITSPTTGDTATYFCARAVYAGAMDLWGQGTLVTVSS |
| Extracellular AS7B16 | SEQ ID NO: 68 (H-L orientation)<br>QVTLKESGPGILQPSQTLSLTCSFSGFSLNTSGTGVGWIRQPS<br>GKGLEWLAHIWWDDDKGYNPALKSRLTISKNTSSNLVFLKI<br>ASVDTADTATYYCVRIKGRMDYWGQGTSVTVSSGGGGS<br>GGGSGGGGSGGGGSNIMMTQSPSSLAVSAGEKVTMNCKSS<br>QSVLFGSKQKNYLAWYQQKPGQSPKLLIYWASTRESGVPD<br>RFTGSGSGTDFILTISNVQAEDLAVYYCHQYLSLFTFGSGTK<br>LEIKTTTPAPRPPTPAPTIASQPLSLRPEACRPAAGGAVHTRG<br>LDFACDIYIWAPLAGTCGVLLLSLVITLYCKRGRKKLLYIFK<br>QPFMRPVQTTQEEDGCSCRFPEEEEGGCELRVKFSRSADAP<br>AYKQGQNQLYNELNLGRREEYDVLDKRRGRDPEMGGKPR<br>RKNPQEGLYNELQKDKMAEAYSEIGMKGERRRGKGHDGL<br>YQGLSTATKDTYDALHMQALPPR |

TABLE 12-continued

Amino Acid Sequence of the two different
AS7B91, AS7B16 and AS7B82 CAR constructs
(H-L orientation and L-H orientation).

| Domain | Sequence |
|---|---|
| | SEQ ID NO: 69 (L-H orientation)<br>NIMMTQSPSSLAVSAGEKVTMNCKSSQSVLFGSKQKNYLA<br>WYQQKPGQSPKLLIYWASTRESGVPDRFTGSGSGTDFILTIS<br>NVQAEDLAVYYCHQYLSLFTFGSGTKLEIKGGGGSGGGGS<br>GGGGSGGGGSQVTLKESGPGILQPSQTLSLTCSFSGFSLNTS<br>GTGVGWIRQPSGKGLEWLAHIWWDDDKGYNPALKSRLTIS<br>KNTSSNLVFLKIASVDTADTATYYCVRIKGRMDYWGQGTS<br>VTVSSTTTPAPRPPTPAPTIASQPLSLRPEACRPAAGGAVHTR<br>GLDFACDIYIWAPLAGTCGVLLLSLVITLYCKRGRKKLLYIF<br>KQPFMRPVQTTQEEDGCSCRFPEEEEGGCELRVKFSRSADA<br>PAYKQGQNQLYNELNLGRREEYDVLDKRRGRDPEMGGKP<br>RRKNPQEGLYNELQKDKMAEAYSEIGMKGERRRGKGHDG<br>LYQGLSTATKDTYDALHMQALPPR |
| Extracellular AS7B82 | SEQ ID NO: 70 (H-L orientation)<br>QEQQKESGGGLVKPGASLTLTCTASGIDFSSVAYMCWVRQ<br>APGKGLEWIACIYAGSSSSIYYASWAKGRFTVSRTSSTTVTL<br>QMTSLTAADTATYFCARGLFTSGSGYYIDMWGPGTLVTVSS<br>GGGGSGGGGSGGGGSGGGGSDVVMTQTPSSVEVAVGGT<br>VTIKCQASQSIGSNLAWYQQKPGQRPKLLIYGASNLAAGVP<br>SRFSGSGSGTQFTLTISDVECADAATYYCQRGYISSAVDFFV<br>FGGGTEVVVKGTTTPAPRPPTPAPTIASQPLSLRPEACRPAA<br>GGAVHTRGLDFACDIYIWAPLAGTCGVLLLSLVITLYCKRG<br>RKKLLYIFKQPFMRPVQTTQEEDGCSCRFPEEEEGGCELRVK<br>FSRSADAPAYKQGQNQLYNELNLGRREEYDVLDKRRGRDP<br>EMGGKPRRKNPQEGLYNELQKDKMAEAYSEIGMKGERRR<br>GKGHDGLYQGLSTATKDTYDALHMQALPPR<br>SEQ ID NO: 71 (L-H orientation)<br>DVVMTQTPSSVEVAVGGTVTIKCQASQSIGSNLAWYQQKP<br>GQRPKLLIYGASNLAAGVPSRFSGSGSGTQFTLTISDVECAD<br>AATYYCQRGYISSAVDFFVFGGGTEVVVKGGGGGSGGGG<br>SGGGGSGGGGSEQQKESGGGLVKPGASLTLTCTASGIDFSS<br>VAYMCWVRQAPGKGLEWIACIYAGSSSSIYYASWAKGRFT<br>VSRTSSTTVTLQMTSLTAADTATYFCARGLFTSGSGYYIDM<br>WGPGTLVTVSSTTTPAPRPPTPAPTIASQPLSLRPEACRPAAG<br>GAVHTRGLDFACDIYIWAPLAGTCGVLLLSLVITLYCKRGR<br>KKLLYIFKQPFMRPVQTTQEEDGCSCRFPEEEEGGCELRVKF<br>SRSADAPAYKQGQNQLYNELNLGRREEYDVLDKRRGRDPE<br>MGGKPRRKNPQEGLYNELQKDKMAEAYSEIGMKGERRRG<br>KGHDGLYQGLSTATKDTYDALHMQALPPR |
| human CD8 hinge | SEQ ID NO: 24<br>TTTPAPRPPTPAPTIASQPLSLRPEACRPAAGGAVHTRGLDF<br>ACDIY |
| human CD8 TM domain | SEQ ID NO: 25<br>IWAPLAGTCGVLLLSLVITLYCK |
| human 4-1BB intracellular domain | SEQ ID NO: 26<br>RGRKKLLYIFKQPFMRPVQTTQEEDGCSCRFPEEEEGGCEL |
| human CD3 zeta intracellular domain | SEQ ID NO: 27<br>RVKFSRSADAPAYKQGQNQLYNELNLGRREEYDVLDKRRG<br>RDPEMGGKPRRKNPQEGLYNELQKDKMAEAYSEIGMKGER<br>RRGKGHDGLYQGLSTATKDTYDALHMQALPPR |

Figure 3:
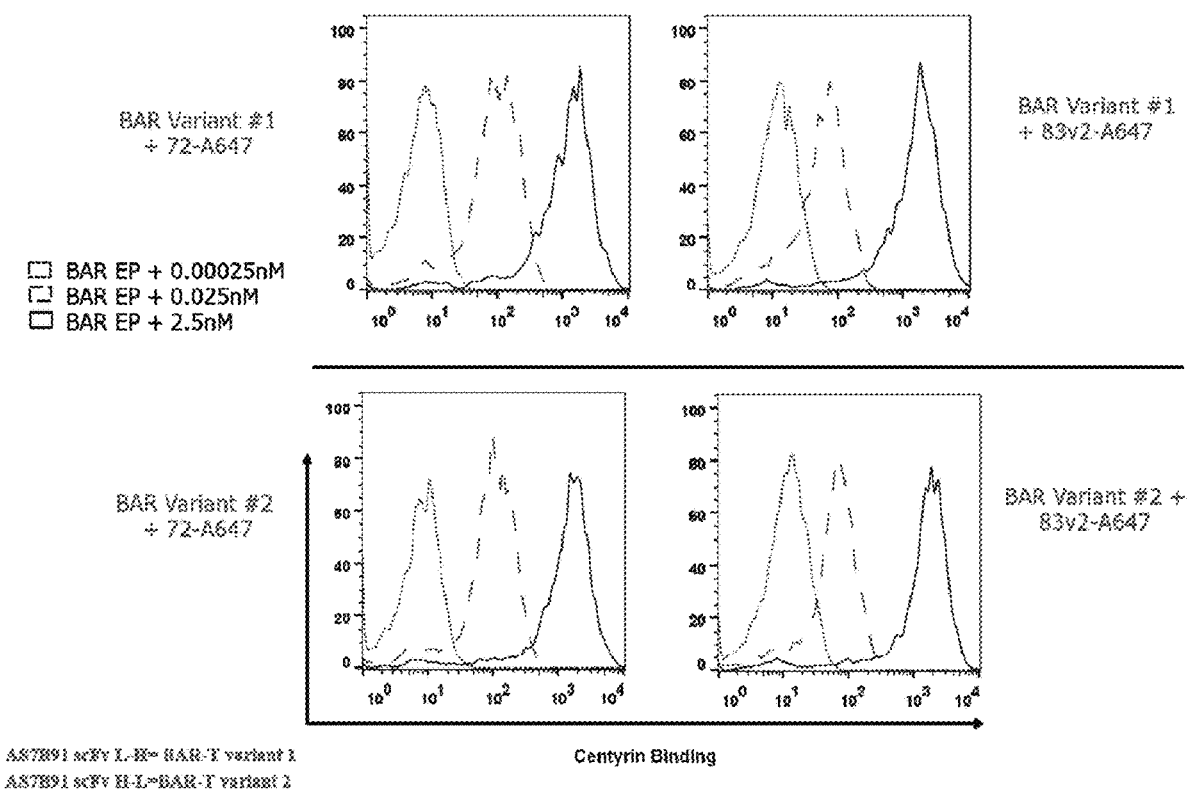
FIG. 3 shows detection of AS7B91 scFv CAR expression on the surface of primary T cells using labeled tencon 25.

Example 7: Generation and Analysis of Engineered Immune Cells Expressing AS7B91, AS7B16, and AS7B82 Cars mRNA was electroporated into pan T-cells derived from normal human blood (Normal Blood Donor Service—TSRD using the ECM 830 Square Wave Electroporation System (BTX). $5 \times 10^6$ pan T-cells received a single electric pulse (500V, 750 µs) per the manufacturer's protocol, either with or without 10 µg of AS7B91 CAR mRNA. Surface expression of CARs was assessed 24 hours later using a polyclonal anti-FN3 domain Ab. The results are shown in FIG. 3.

The functionality of the AS7B91 scFv CAR cells were tested for their ability to bind to FN3 domains and induce T cell killing in response to FN3 domain binding to target cells. This was first determined in a degranulation assay using BCMA-specific FN3 domains along with $BCMA^{hi}$ (H929 cells), $BCMA^{lo}$ (DOHH-2 cells) $BCMA^{neg}$ (EXPI293 cells) target cells, and then in a killing assay.

Figure 4A:
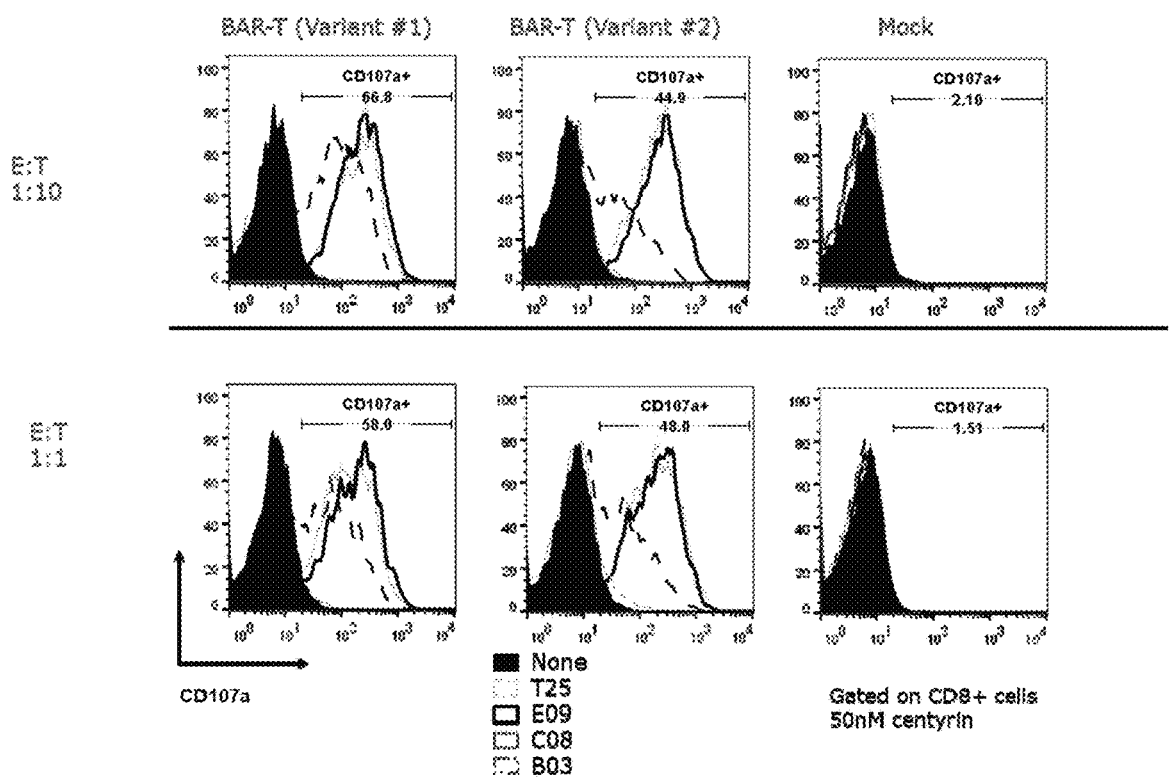
FIG. 4A-4C show AS7B91 scFv CAR-BCMA specific FN3 domain degranulation in response to BCMA-expressing target cells.
Figure 4B:
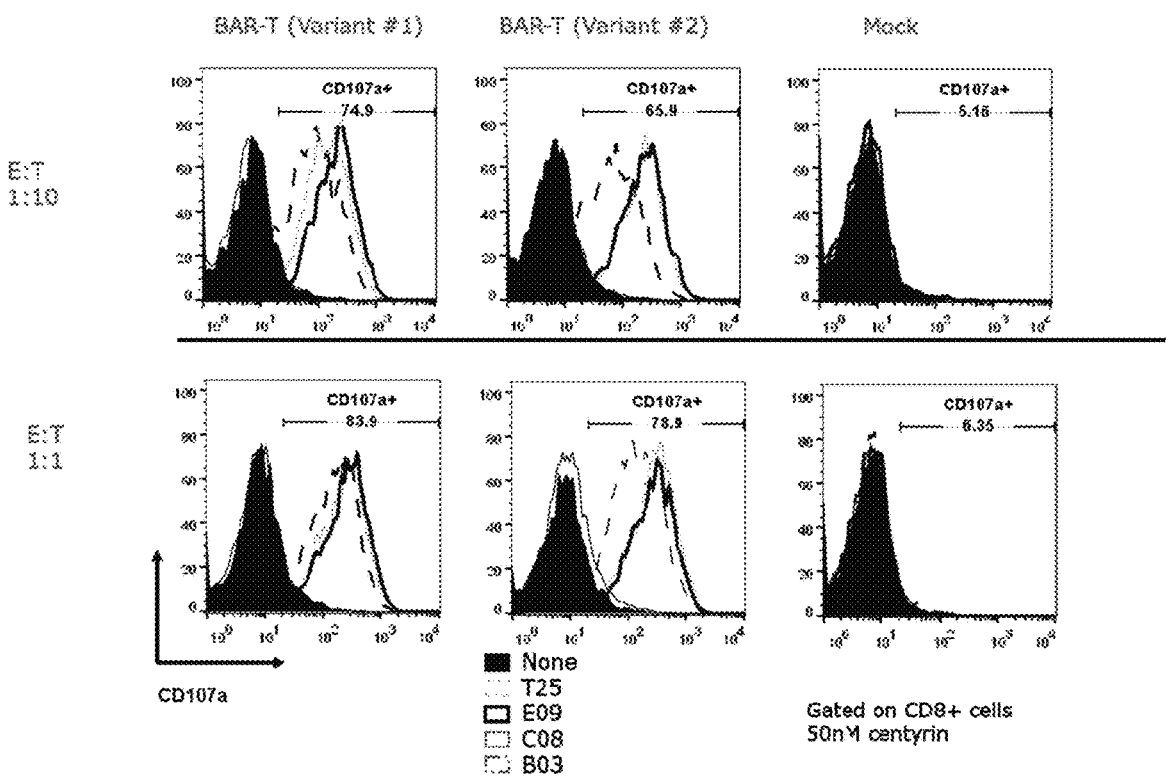
Figure 4C:
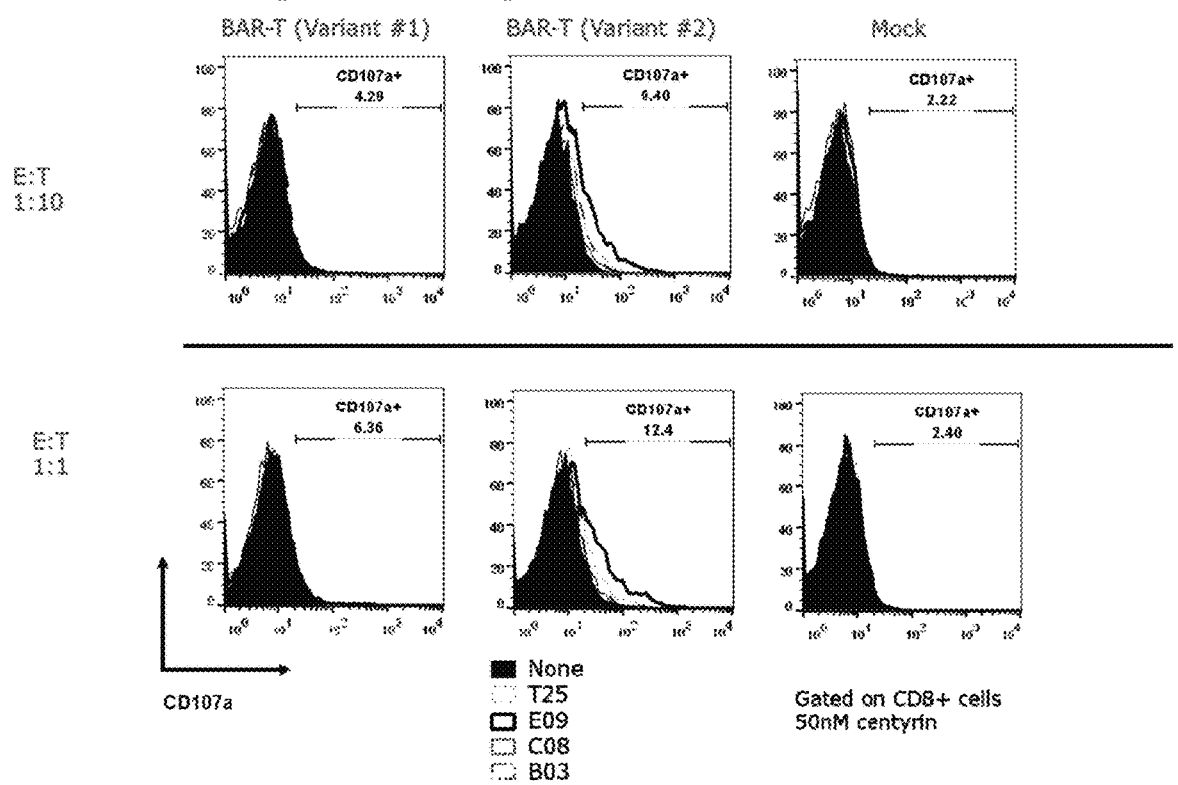

In the degranulation assay (CD107a mobilization) T-cells were incubated in 96-well plates, together with 1:1 or 1:10 amount of cells expressing or not the BCMA protein. Co-cultures were maintained in a final volume of OpTmizer "complete" media containing 1:1500 Golgi Stop (BD) and 1:1300 anti-CD107a APC (Biolegend) for 4 hours at 37 C. After the 4h incubation period, cells were stained with a fixable viability dye (eFluor 780, from eBioscience) and fluorochrome-conjugated anti-CD8 (PE conjugated, Biolegend) and analyzed by flow cytometry. The degranulation activity was determined by determining the mean fluorescence intensity signal (MFI) for CD107a staining among CD8+ cells. Degranulation assays were carried out 24h after mRNA transfection. As seen in FIG. 4, upon the addition of an anti-BCMA specific FN3 domain, the AS7B91 scFv CAR expressing T cells underwent degranulation in an anti-BCMA and AS7B91 specific manner. These data show that the AS7B91 scFv CAR is functional in its ability to bind to and signal in response to a target specific FN3 domain, in which the target is expressed on the surface of other cells.

Figure 5:
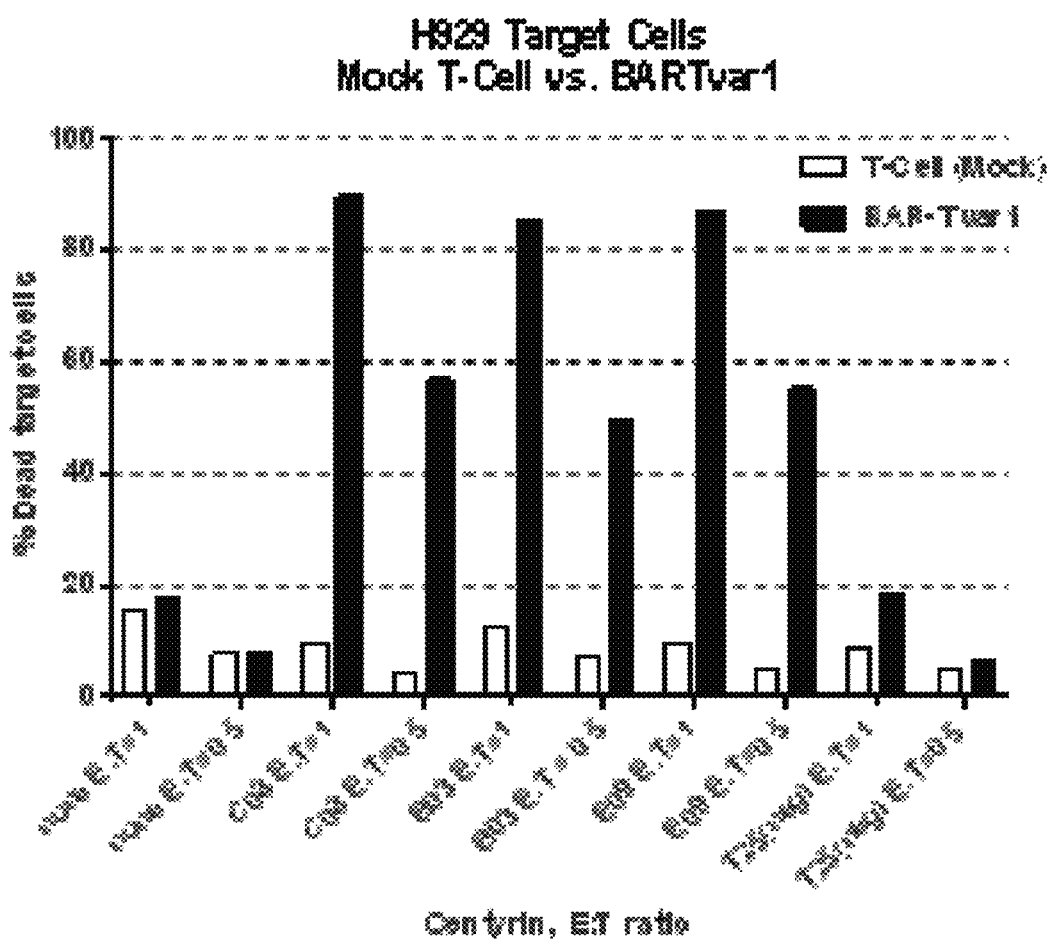
FIG. 5 shows AS7B91 scFv CAR-BCMA killing of BCMA expressing target cells. H929, BCMA high expressing cells; ARH77, BCMA low expressing cells; K562, BCMA negative cells. Different FN3 domains were incubated at a concentration of 25 nM with AS7B91 scFv CAR T cells, washed, and then added to target cells at a 1:1 ration. BAR-T variant 1=AS7B91 scFv L-H CAR; BAR-T variant 2=AS7B91 scFv H-L CAR.
Figure 6:
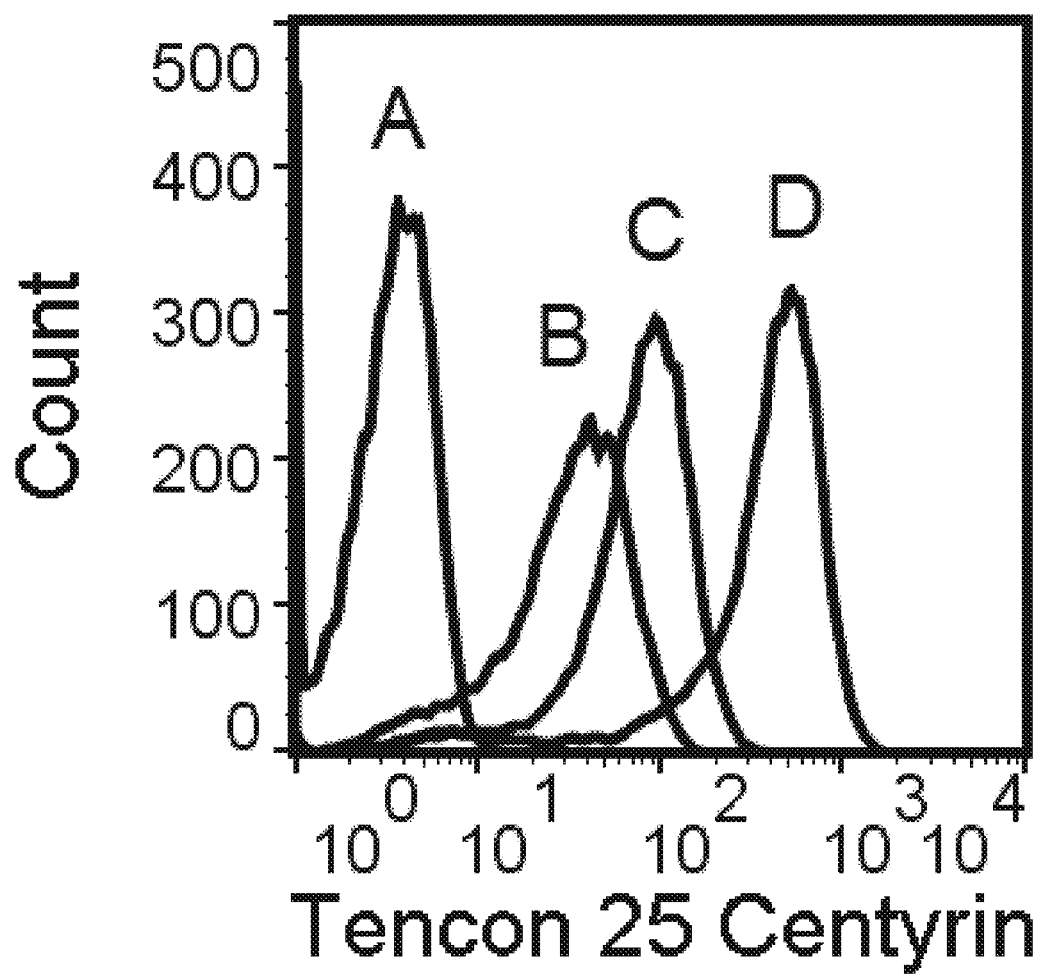
FIG. 6 shows binding of labeled Tencon-25 to AS7B16 scFv CAR constructs on T cells. L2H, AS7B16 light chain-heavy chain orientation. H2L, AS7B16 heavy chain-light chain orientation.
Figure 8:
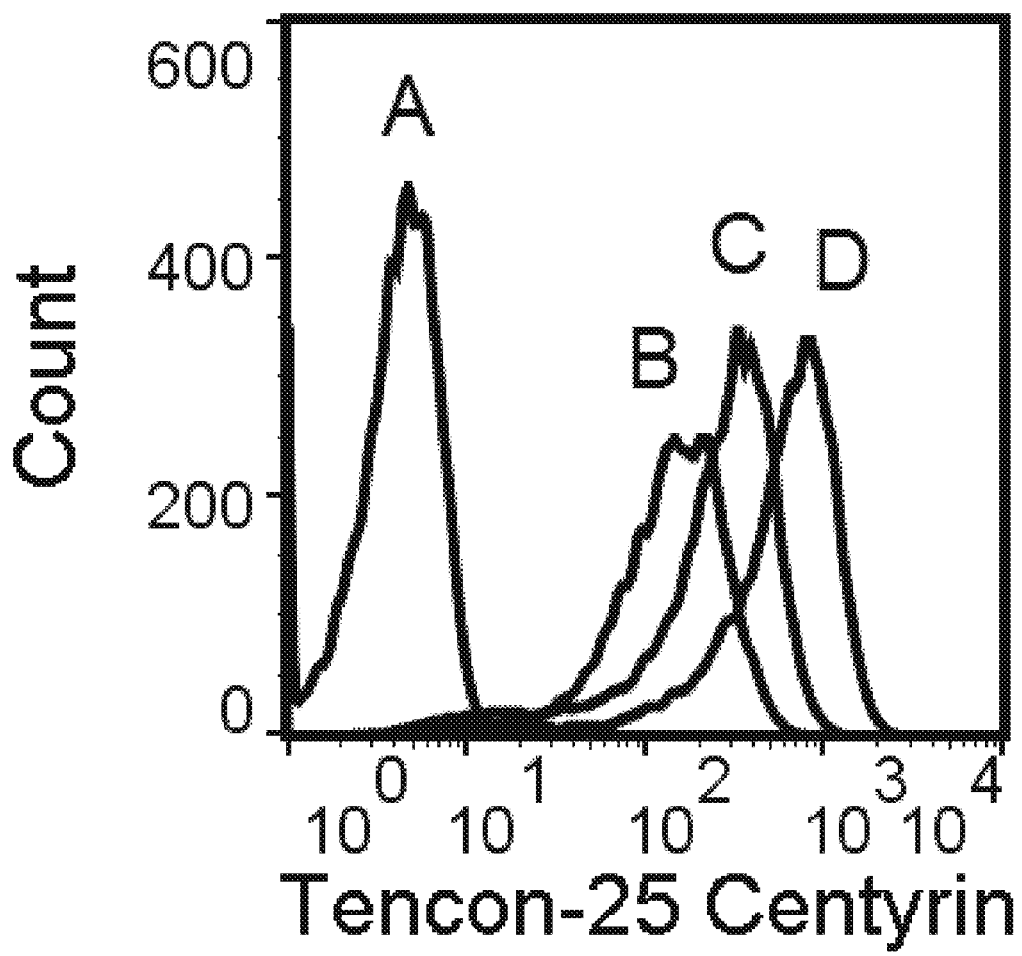
FIG. 8 shows binding of labeled Tencon-25 to AS7B82 scFv CAR constructs on T cells. L2H, AS7B82 light chain-heavy chain orientation. H2L, AS7B16 heavy chain-light chain orientation.
Figure 9:
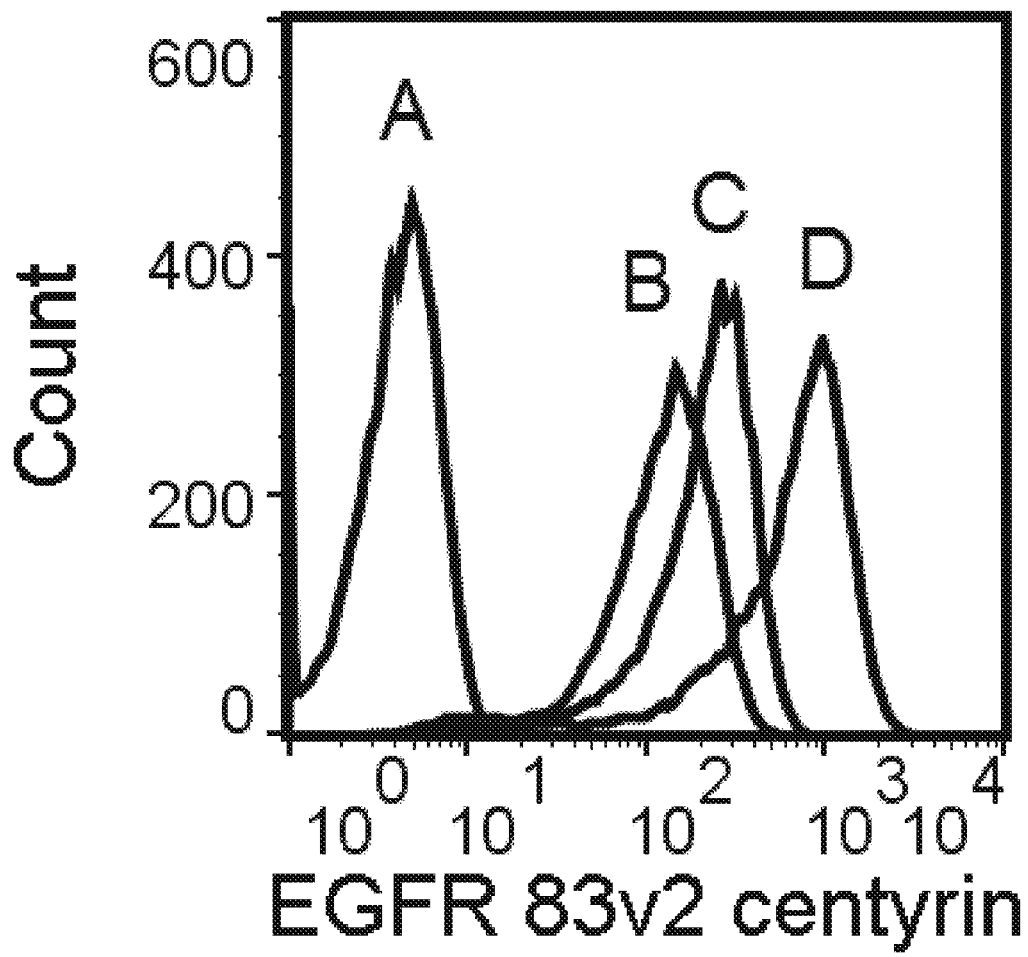
FIG. 9 shows binding of labeled EGFR 83v2 to AS7B82 scFv CAR constructs on T cells. L2H, AS7B16 light chain-heavy chain orientation. H2L, AS7B16 heavy chain-light chain orientation.
Figure 10:
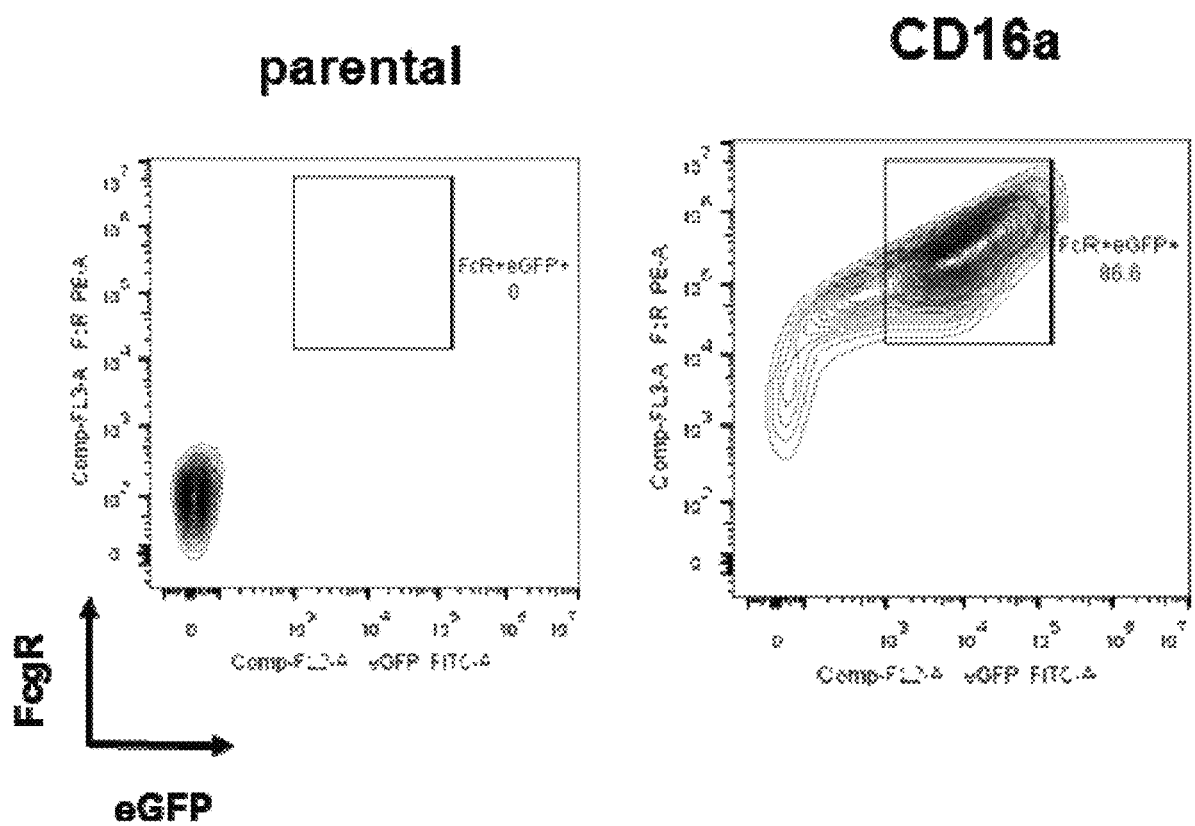
FIG. 10 Generation of FcgR expressing cell lines. Purified lentiviral expression plasmids encoding for human FcgRs (CD16a, CD32 and CD64) were packaged for transfection of 293T cells using the Lenti-Pac HIV Expression Packaging System.
Figure 10:
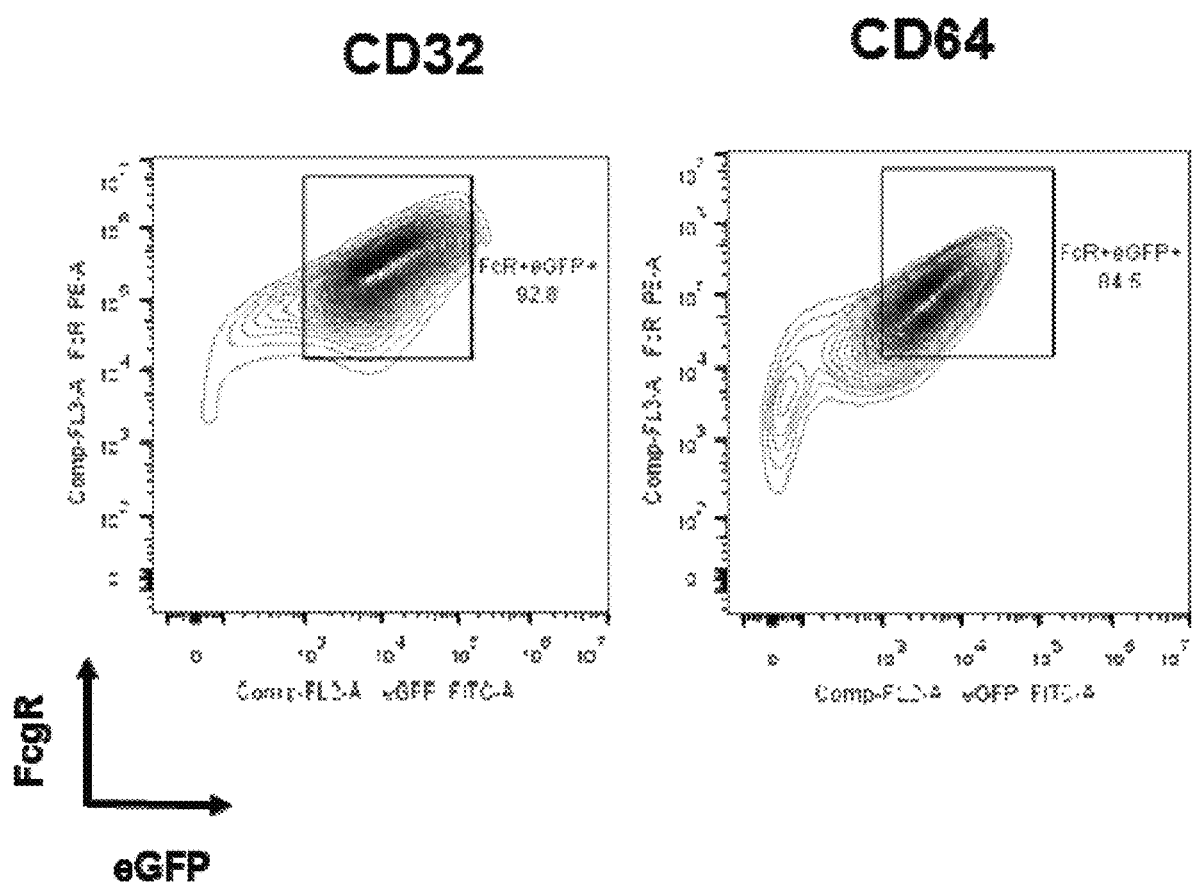
Figure 12:
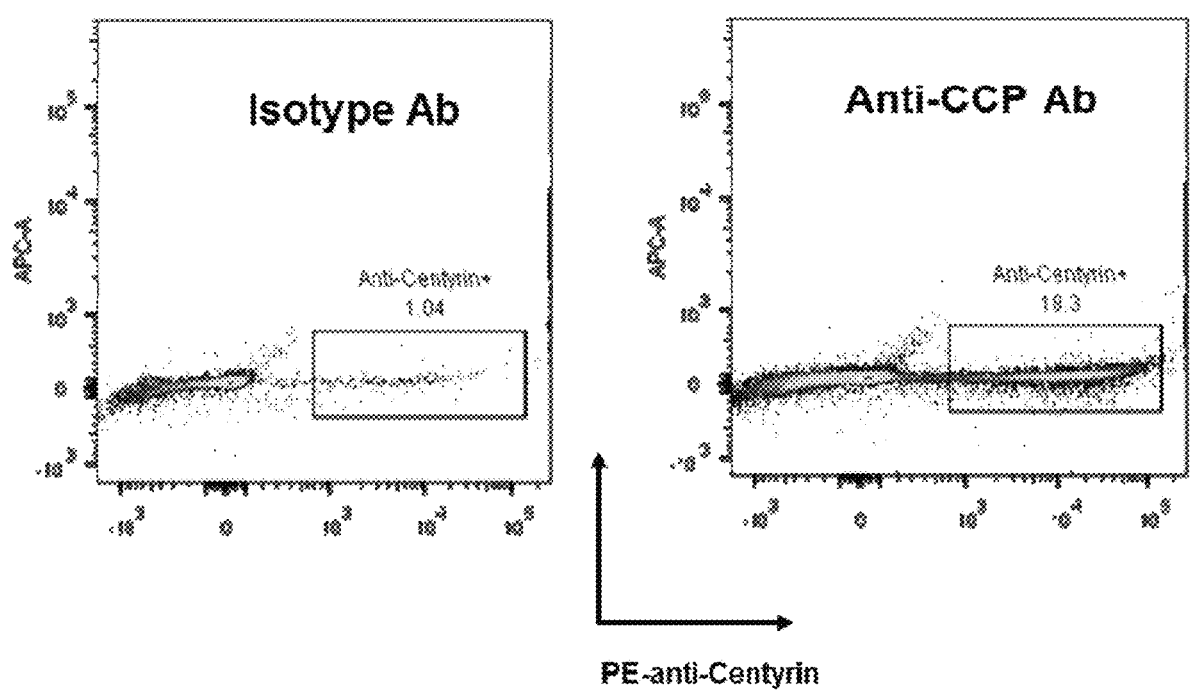
FIG. 12. Detection of anti-citrullinated antibody binding to centyrin-CCP1-peptide conjugates. FcgR expressing HEK293 cells were incubated with 200 ug/mL of human anti-citrullinated fibrinogen antibody or human IgG1 isotype control. Binding was assessed by flow cytometry.
Figure 13:
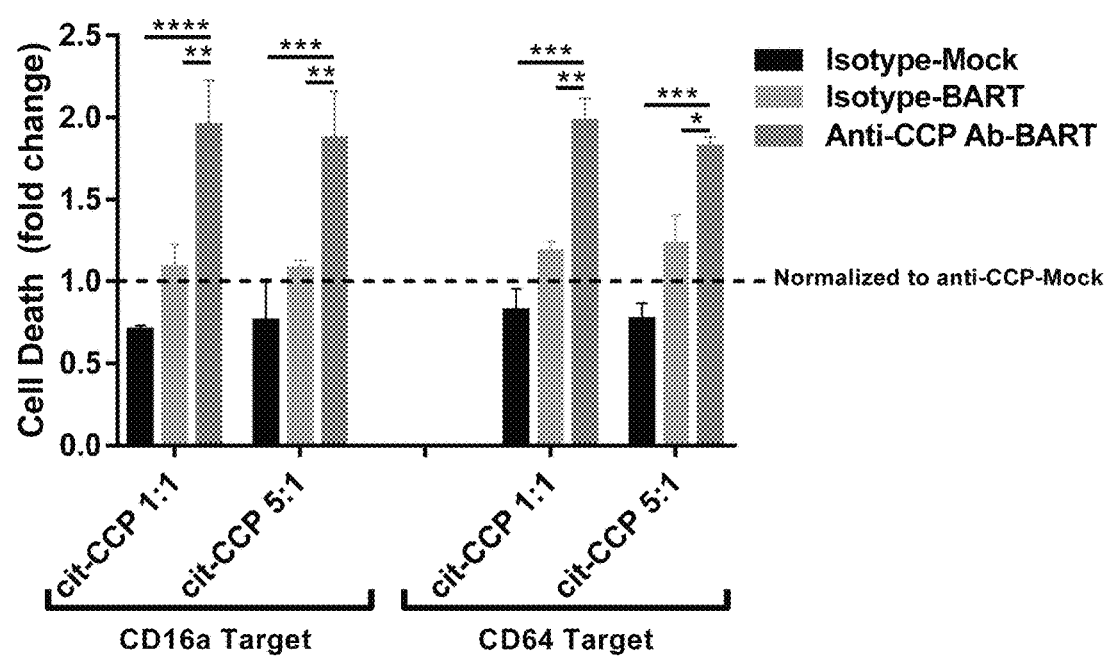
FIG. 13. AS7B91 scFv CAR-T cell mediated killing of anti-citrullinated mAb bound FcR expressing cells.
Figure 14A:
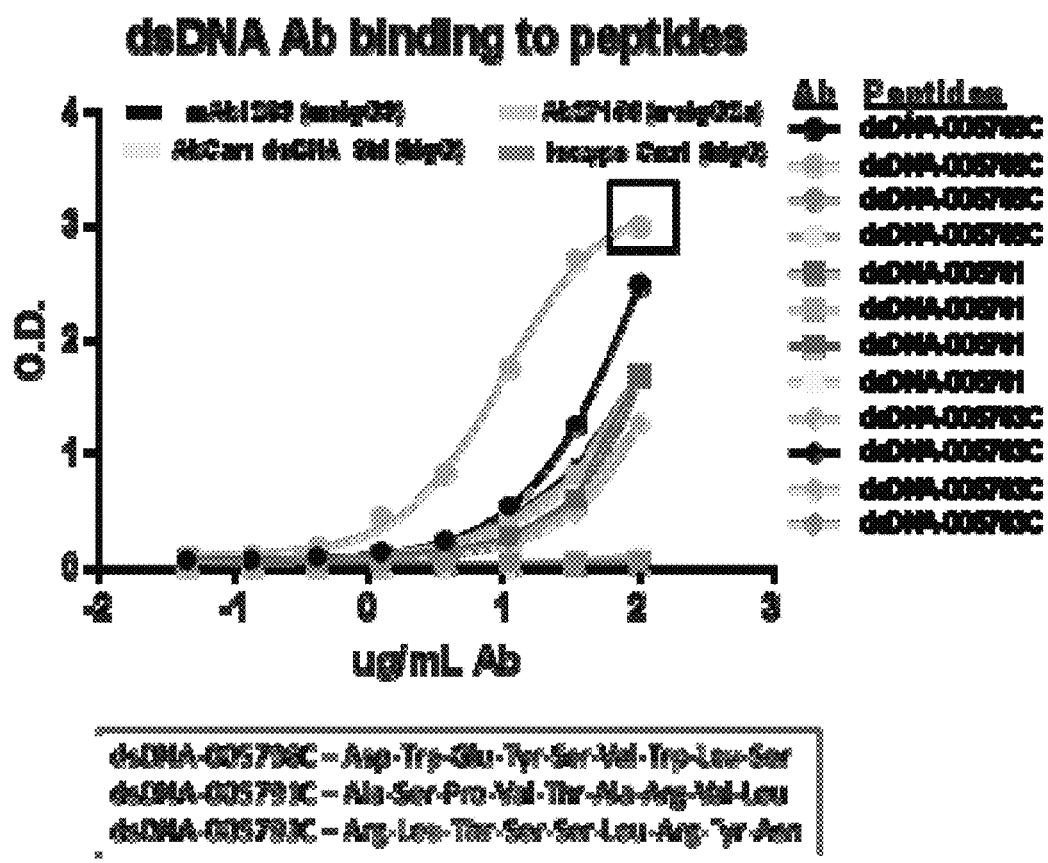
FIG. 14A-14C. Evaluation of potential peptide/antibody combinations in multiple autoimmune diseases for BAR-T platform expansion. Peptides specific for a) Myasthenia Gravis (MG), b) Multiple Sclerosis (MS) and c) systemic lupus erythematosus (SLE) were tested for their ability to bind to anti-AChR, anti-MOG, or anti dsDNA antibodies, respectively.
Figure 14B:
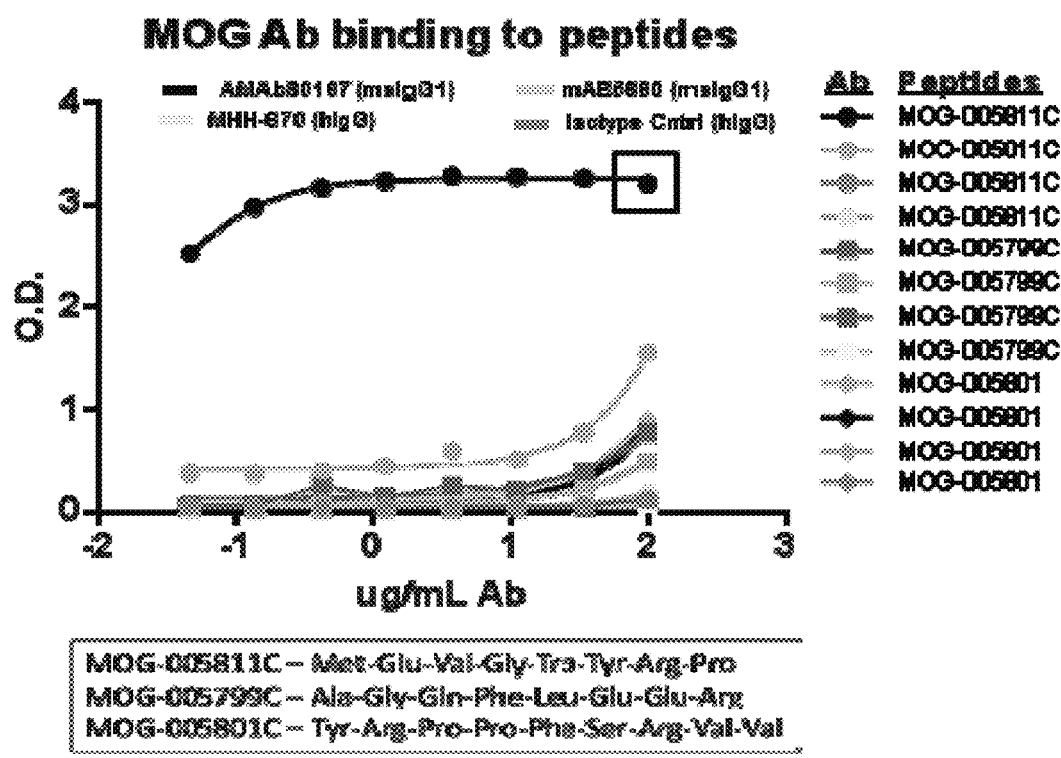
Figure 14C:
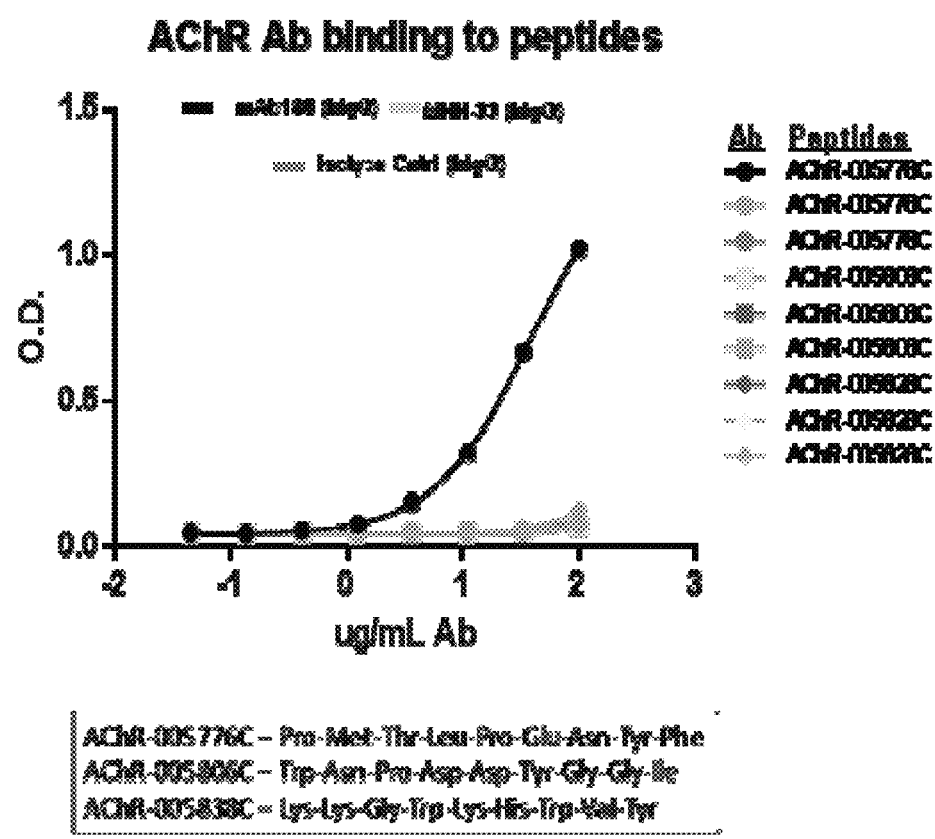

AS7B91 scFv CAR-T cell killing in response to BCMA-specific FN3 domains along with CFSE labeled-BCMA1$^{hi}$ (U-2932 cells), BCMA$^{lo}$ (DOHH-2 cells) BCMA$^{neg}$ (EXPI293 cells) target cells was evaluated. CAR-T/mock T cells were preincubated with the BCMA-specific FN3 domains for 1 hour at 37° C. prior to a 48-hour incubation with the BCMA target cells at E:T ratios ranging from 0 to 1. At the end of the experiment, dead cells were labeled with CFSE-FL1, SYTOX-red-FL4. The percentage of cell death was analyzed by a flow cytometer (FACSCalibur) and the data was analyzed with FlowJo v 10. As seen in FIG. 5, upon the addition of a BCMA-specific FN3 domain, the AS7B91 scFv CAR expressing T cells killed BCMA expressing target cells in an anti-BCMA FN3 domain and AS7B91 scFv CAR-specific manner. These data show that the AS7B91 scFv CAR is functional in its ability to bind to and signal in response to a target specific FN3 domain, in which the target is expressed on the surface of other cells.

For AS7B16 and AS7B82, binding was assessed using flow cytometry. Briefly, Twenty-four hours post-electroporation, cells were centrifuged at 100×g for 10 minutes and washed two times in FACS stain buffer (BD Biosciences Catalog #554657). Cells were incubated with either APC labeled anti-Tencon-25 or AF647 labeled anti-EGFR 83v2 FN3 domains at a final concentration of 50 nM at 4° C. for 1 hour. The labeled cells were washed twice in FACS stain buffer and re-suspended in 200 uL of the same buffer. Data was collected using a BD LSRFortessa flow cytometer and analysis was performed using Flowjo software. The data is shown in FIG. 6 to FIG. 9. All CARTs tested, AS7B16, AS7B82 and AS7B91 bind to both FN3 domains tested, Tencon-T25 and EGFR 83v2. Binding of CARTs occurs in the following manner: ASS7B91>AS7B82>AS7B16.

Example 8: In Vitro Killing of Anti-Citrullinated Protein Antibody-Expressing Cells Mediated by AS7B91 scFv Car-T Pre-Complexed with Fn3 Domain-Conjugated to Cyclic Citrullinated Peptides Autoimmune diseases are characterized by the dysregulated production of antibodies to self-antigens (auto-antibodies). These autoantibodies can be directed against a variety of molecules including, but not limited to, proteins and nucleic acids. In the case of proteins, these autoantibodies often recognize post-translationally modified antigens. Shown below is the in vitro killing of anti-citrullinated protein antibody (ACPA) expressing cells mediated by AS7B91 scFv CAR-T cells ("BAR-T" cells) pre-complexed with centyrin conjugated to cyclic citrullinated peptides (CCP-1). This finding suggests that self-antigens can be conjugated to the Tencon25 centyrin for engagement with BAR-T cells leading to targeted elimination of antigen-specific, auto-reactive B cells.

Generation of FcgR Expressing Cell Lines

Purified lentiviral expression plasmids encoding for human FcgRs (CD16a, CD32 and CD64) were packaged for transfection of 293T cells using the Lenti-Pac HIV Expression Packaging System (GeneCopoeia). Seventy-two hours post transfection, lenti-containing supernatant was harvested and used to transduce HEK293 cells. Media was supplemented with polybrene (final concentration-8 ug/mL). The next day, polybrene containing media was replaced with RPMI Media 1640 supplemented with 10% fetal bovine serum. Seventy-two hours post transduction, cells were harvested and stained for FcgR expression. The cells were then sorted based on FcgR expression (SH800S Cell Sorter-Sony Biotechnology). High expressing cells were cultured and used as target cells for future studies.

Conjugation of Citrullinated Cyclic Peptides to Tencon25 Centyrin

Glycine tagged (GGG-) citrullinated cyclic peptide-1 (CCP-1-Cit) and arginine control peptide (CCP-1-Arg) were obtained from Peptides International. Sortase-v5 tagged Tencon25 (Tencon25_sort_v5) was desalted into TBS and concentrated prior to conjugation. Each peptide was conjugated at a 1:5 ratio (FN3 domain to peptide) via sortase chemistry. Conjugates were purified manually over a Ni Sepharose column (GE) to remove free sortase and peptide. Following purification, the conjugates were buffered exchanged in to PBS and concentrated. Conjugates were QC'd by (a) mass spectrometry (LC-MS) and (b) size exclusion chromatography (superdex 75) and sterile filtered.

Detection of Anti-Citrullinated Antibody Binding to Centyrin-CCP1-Peptide Conjugates FcgR expressing HEK293 cells were incubated with 200 ug/mL of human anti-citrullinated fibrinogen antibody (clone 1F11-Modiquest) or human IgG1 isotype control (Abcam) for 30 mins on ice. Cells were washed 2× with FACS Buffer then incubated with centyrin-CCP1-Cit conjugate (576 nM) for 1hr on ice. Cells were washed 2× with FACS buffer then incubated with PE-labeled anti-centyrin (AS7B91) antibody for 30 mins on ice. Binding was assessed by flow cytometry (BD FACSCanto II) and analyzed with BD FACSDiva 6.1.3 software.

AS7B91 scFv CAR-T Cell Mediated Killing of Anti-Citrullinated mAb Bound FcR Expressing Cells Mock electroporated T cells (Mock) or AS7B91 scFv CAR-T cells ("BAR-T") were pre-complexed with centyrin-conjugated CCP1 (cit-CCP). HEK293 cells expressing CD16a or CD64 were labeled with Cell Tracker Green (CTG) dye (ThermoFisher) and pre-complexed with either human IgG1 isotype control or anti-citrullinated fibrinogen antibody (anti-CCP Ab). BAR-T and HEK293 cells were then plated at a 1:1 or 5:1 ratio for ~18 hrs. At the end of the experiment, cells were stained with Zombie Dye Violet (Biolegend). Dead cells were considered as CTG+/Zombie+ cells as assessed by flow cytometry (BD FACSCanto II). The data was analyzed with BD FACSDiva 6.1.3 and Graphpad Prism 5 software. A 2-fold increase in cell death of target cells bound to the anti-citrullinated antibody when incubated with BAR-T cells pre-complexed with centyrin-CCP-1-cit relative to incubation with mock T cells or isotype control antibodies was observed.

Evaluation of Potential Peptide/Antibody Combinations in Multiple Auto-Immune Diseases for BAR-T Platform Expansion Peptides specific for a) Myasthenia Gravis (MG), b) Multiple Sclerosis (MS) and c) systemic lupus erythematosus (SLE) were tested for their ability to bind to anti-AChR, anti-MOG, or anti dsDNA antibodies, respectively. Three high affinity binding neutravidin plates were coated with 10 ug/mL of indicated peptides. Plates were washed 3× with PBS-T and blocked with 2× Assay Buffer A (eBioscience) for 2 hrs at room temperature. Plates were washed 3× with PBS-T and 100 ug/mL of indicated antibody was added for 1hr at room temperature. Plates were washed 3× with PBS-T and the appropriate secondary antibody was added for 1hr at room temperature. Plates were washed 3× with PBS-T and TMB Substrate was added for 5-8 mins prior to addition of Stop Solution (ThermoFisher). The SpectraMax340PC instrument was used to read the absorbance and the data was analyzed using Graphpad Prism 5 software. The binding results identified one potential lead peptide/antibody combination for each disease indication for further evaluation.

| SEQ ID NO: | Type | Species | Description | Sequence |
|---|---|---|---|---|
| 1 | PRT | rabbit | CEN-25-105-5 HCDR1 IMGT | GIDLSTSV |
| 2 | PRT | rabbit | CEN-25-105-5 HCDR1 Kabat | TSVMG |
| 3 | PRT | rabbit | CEN-25-105-5 HCDR1 Chothia | GIDLSTS |
| 4 | PRT | rabbit | CEN-25-105-5 HCDR2 IMGT | IYTNVNT |
| 5 | PRT | rabbit | CEN-25-105-5 HCDR2 Kabat | FIYTNVNTYYASWAKG |
| 6 | PRT | rabbit | CEN-25-105-5 HCDR2 Chothia | YTNVN |
| 7 | PRT | rabbit | CEN-25-105-5 HCDR3 IMGT | ARAVYAGAMDL |
| 8 | PRT | rabbit | CEN-25-105-5 HCDR3 Kabat and Chothia | AVYAGAMDL |
| 9 | PRT | rabbit | CEN-25-105-5 LCDR1 IMGT | ERIYSN |
| 10 | PRT | rabbit | CEN-25-105-5 LCDR1 Kabat and Chothia | QASERIYSNLA |
| 11 | PRT | rabbit | CEN-25-105-5 LCDR2 IMGT | KAS |
| 12 | PRT | rabbit | CEN-25-105-5 LCDR2 Kabat and Chothia | KASTLAS |

-continued

| SEQ ID NO: | Type | Species | Description | Sequence |
|---|---|---|---|---|
| 13 | PRT | rabbit | CEN-25-105-5 LCDR3 IMGT, Kabat and Chothia | QYTSYGSGYVGT |
| 14 | PRT | rabbit | CEN-25-105-5 VH | QSLEESGGRLVTPGTPLTLTCTVSGID LSTSVMGWVRQAPGKGLESIGFIYTN VNTYYASWAKGRFTISRTSTTVDLKI TSPTTGDTATYFCARAVYAGAMDL WGQGTLVTVSS |
| 15 | PRT | rabbit | CEN-25-105-5 VL | DVVMTQTPASVSGPVGGTVTIKCQA SERIYSNLAWYQQKPGQPPKLLIYKA STLASGVSSRFKGSGSGTEFTLTIRDL ECADAATYSCQYTSYGSGYVGTFGG GTEVVVEG |
| 16 | DNA | rabbit | CEN-25-105-5 VH | Ctggaggagtccgggggtcgcctggtcacgcctgggac accctgacactcacctgcacagtctctggaatcgacctc agtacctctgtcatgggttgggtccgccaggctccaggga agggctggaatccatcggattcatttatactaatgttaaca catactacgcgagctgggcaaaaggccgattcaccatctc cagaacctcgaccacggtggatctgaaaatcaccagtcc gacaacggggacacggccacctatttctgtgccagagc tgtttatgctggtgctatggacttgtggggccaaggcaccc tggtcaccgtctcctca |
| 17 | DNA | rabbit | CEN-25-105-5 VL | gatgttgtgatgacccagactccagcctccgtgtctggac ctgtgggaggcacagtcaccatcaagtgccaggccagtg agagaatttatagcaatttagcctggtatcagcagaaacca gggcagcctcccaaaactcctgatctacaaggcatccactc tggcatctggggtctcatcgcggttcaaaggcagtggatc tgggacagagttcactctcaccatcagggaccttgagtgt gccgatgctgccacttactcctgtcaatatacttcttatggc agtggttatgttggtactttcggcggagggaccgaggtgg tggtcgaaggt |
| 18 | PRT | artificial | AS7B91-Heavy Chain | QSLEESGGRLVTPGTPLTLTCTVSGID LSTSVMGWVRQAPGKGLESIGFIYTN VNTYYASWAKGRFTISRTSTTVDLKI TSPTTGDTATYFCARAVYAGAMDL WGQGTLVTVSSAKTTAPSVYPLAPV CGDTTGSSVTLGCLVKGYFPEPVTLT WNSGSLSSGVHTFPAVLQSDLYTLSS SVTVTSSTWPSQSITCNVAHPASSTK VDKKIEPRGPTIKPCPPCKCPAPNLLG GPSVFIFPPKIKDVLMISLSPIVTCVVV DVSEDDPDVQISWFVNNVEVHTAQT QTHREDYNSTLRVVSALPIQHQDWM SGKEFKCKVNNKDLPAPIERTISKPK GSVRAPQVYVLPPPEEEMTKKQVTL TCMVTDFMPEDIYVEWTNNGKTELN YKNTEPVLDSDGSYFMYSKLRVEKK NWVERNSYSCSVVHEGLHNHHTTKS FSRTPGK |
| 19 | PRT | artificial | AS7B91-Light Chain | DVVMTQTPASVSGPVGGTVTIKCQA SERIYSNLAWYQQKPGQPPKLLIYKA STLASGVSSRFKGSGSGTEFTLTIRDL ECADAATYSCQYTSYGSGYVGTFGG GTEVVVEGRADAAPTVSIFPPSSEQL TSGGASVVCFLNNFYPKDINVKWKI DGSERQNGVLNSWTDQDSKDSTYS MSSTLTLTKDEYERHNSYTCEATHK TSTSPIVKSFNRNEC |
| 20 | PRT | artificial | AS7B90-Heavy Chain | QSLEESGGRLVTPGTPLTLTCTVSGID LSTSVMGWVRQAPGKGLESIGFIYTN VNTYYASWAKGRFTISRTSTTVDLKI TSPTTGDTATYFCARAVYAGAMDL WGQGTLVTVSSAETTAPSVYPLAPG |

-continued

| SEQ ID NO: | Type | Species | Description | Sequence |
|---|---|---|---|---|
| | | | | TALKSNSMVTLGCLVKGYFPEPVTV TWNSGALSSGVHTFPAVLQSGLYTL TSSVTVPSSTWPSQTVTCNVAHPASS TKVDKKIVPRNCGGDCKPCICTGSEV SSVFIFPPKPKDVLTITLTPKVTCVVV DISQDDPEVHFSWFVDDVEVHTAQT RPPEEQFNSTFRSVSELPILHQDWLN GRTFRCKVTSAAFPSPIEKTISKPEGR TQVPHVYTMSPTKEEMTQNEVSITC MVKGFYPPDIYVEWQMNGQPQENY KNTPPTMDTDGSYFLYSKLNVKKEK WQQGNTFTCSVLHEGLHNHHTEKSL SHSPGK |
| 21 | PRT | artificial | AS7B90-Light Chain | DVVMTQTPASVSGPVGGTVTIKCQA SERIYSNLAWYQQKPGQPPKLLIYKA STLASGVSSRFKGSGSGTEFTLTIRDL ECADAATYSCQYTSYGSGYVGTFGG GTEVVVEGRADAAPTVSIFPPSSEQL ASGGASVVCFINKFYPKDISVKWKID GSERQNDVLNSVTDQDSKDSTYSMS STLTLTKADYERHNLYTCEVVHKTS ASPVVKSFNRNEC |
| 22 | PRT | artificial | AS7B91 H-L scFv | METGLRWLLLVAVLKGVQCQSLEES GGRLVTPGTPLTLTCTVSGIDLSTSV MGWVRQAPGKGLESIGFIYTNVNTY YASWAKGRFTISRTSTTVDLKITSPTT GDTATYFCARAVYAGAMDLWGQGT LVTVSSGGGGSGGGGSGGGGSGGGG SDVVMTQTPASVSGPVGGTVTIKCQ ASERIYSNLAWYQQKPGQPPKLLIYK ASTLASGVSSRFKGSGSGTEFTLTIRD LECADAATYSCQYTSYGSGYVGTFG GGTEVVVEG |
| 23 | PRT | artificial | AS7B91L-H scFv | MDTRAPTQLLGLLLLWLPGARCDVV MTQTPASVSGPVGGTVTIKCQASERI YSNLAWYQQKPGQPPKLLIYKASTL ASGVSSRFKGSGSGTEFTLTIRDLECA DAATYSCQYTSYGSGYVGTFGGGTE VVVEGGGGGSGGGGSGGGGSGGGG SLEESGGRLVTPGTPLTLTCTVSGIDL STSVMGWVRQAPGKGLESIGFIYTNV NTYYASWAKGRFTISRTSTTVDLKIT SPTTGDTATYFCARAVYAGAMDLW GQGTLVTVSS |
| 24 | PRT | human | CD8 hinge | TTTPAPRPPTPAPTIASQPLSLRPEACR PAAGGAVHTRGLDFACDIY |
| 25 | PRT | human | CD8 TM domain | IWAPLAGTCGVLLLSLVITLYCK |
| 26 | PRT | human | 4-1BB intracellular domain | RGRKKLLYIFKQPFMRPVQTTQEEDG CSCRFPEEEEGGCEL |
| 27 | PRT | human | CD3 zeta intracellular domain | RVKFSRSADAPAYKQGQNQLYNELN LGRREEYDVLDKRRGRDPEMGGKPR RKNPQEGLYNELQKDKMAEAYSEIG MKGERRRGKGHDGLYQGLSTATKD TYDALHMQALPPR |
| 28 | PRT | artificial | Tencon25 | LPAPKNLVVSEVTEDSARLSWTAPD AAFDSFLIQYQESEKVGEAIVLTVPGS ERSYDLTGLKPGTEYTVSIYGVKGGH RSNPLSAIFTT |
| 29 | PRT | artificial | Tencon28 | MLPAPKNLVVSEVTHDSARLSWTAP DAAFDSFLIQYQESEKVGEAIVLTVP GSERSYDLTGLKHHTEYTVSIYGVKG GHRSNPLSAIFHTHHHHHH |

Brief Description of the Sequence Listing

| SEQ ID NO: | Type | Species | Description | Sequence |
|---|---|---|---|---|
| 30 | PRT | artificial | P114-83 | MLPAPKNLVVSRVTHDSARLSWTAPDAAFDSFWIRYFEFLGSGEAIVLTVPGSERSYDLTGLKHHTEYVVNIMGVKGGKISPPLSAIFTTHHHHHH |
| 31 | PRT | artificial | A3 | MLPAPKNLVVSRVTEDSARLSWTAPDAAFDSFWIRYFEFLGSGEAIVLTVPGSERSYDLTGLKPGTEYVVNIMGVKGGKISPPLSAIFTTGGHHHHHH |
| 32 | PRT | artificial | 83v2-ABD sequence | MLPAPKNLVVSEVTEDSARLSWDDPWAFYESFLIQYQESEKVGEAIVLTVPGSERSYDLTGLKPGTEYTVSIYGVHNVYKDTNMRGLPLSAIFTTGGGGSGGGGSLAEAKVLANRELDKYGVSDYYKNLINNAKTVEGVKALIDEILAALPGGHHHHHH |
| 33 | PRT | artificial | Tencon | LPAPKNLVVSEVTEDSLRLSWTAPDAAFDSFLIQYQESEKVGEAINLTVPGSERSYDLTGLKPGTEYTVSIYGVKGGHRSNPLSAEFTT |
| 34 | PRT | artificial | Tencon27 | LPAPKNLVVSRVTEDSARLSWTAPDAAFDSFLIQYQESEKVGEAIVLTVPGSERSYDLTGLKPGTEYTVSIYGVKGGHRSNPLSAIFTT |
| 35 | PRT | mouse | AS7B16 HCDR1 IMGT | GFSLNTSGTG |
| 36 | PRT | mouse | AS7B16 HCDR1 KABAT | TSGTGVG |
| 37 | PRT | mouse | AS7B16 HCDR1 CHOTHIA | GFSLNTSGT |
| 38 | PRT | rabbit | AS7B82 HCDR1 IMGT | GIDFSSVAY |
| 39 | PRT | rabbit | AS7B82 HCDR1 KABAT | SVAYMC |
| 40 | PRT | rabbit | AS7B82 HCDR1 CHOTHIA | GIDFSSVA |
| 41 | PRT | mouse | AS7B16 HCDR2 IMGT | IWWDDDK |
| 42 | PRT | mouse | AS7B16 HCDR2 KABAT | HIWWDDDKGYNPALKS |
| 43 | PRT | mouse | AS7B16 HCDR2 CHOTHIA | WWDDD |
| 44 | PRT | mouse | AS7B16 HCDR3 IMGT | VRIKGRMDY |
| 45 | PRT | mouse | AS7B16 HCDR3 KABAT AND CHOTHIA | IKGRMDY |

-continued

| SEQ ID NO: | Type | Species | Description | Sequence |
|---|---|---|---|---|
| 46 | PRT | mouse | AS7B16 LCDR1 IMGT | QSVLFGSKQKNY |
| 47 | PRT | mouse | AS7B16 LCDR1 KABAT AND CHOTHIA | KSSQSVLFGSKQKNYLA |
| 48 | PRT | mouse | AS7B16 LCDR2 IMGT | WAS |
| 49 | PRT | mouse | AS7B16 LCDR2 KABAT AND CHOTHIA | WASTRES |
| 50 | PRT | mouse | AS7B16 LCDR2 IMGT, KABAT AND CHOTHIA | HQYLSLFT |
| 51 | PRT | rabbit | AS7B82 HCDR2 IMGT | IYAGSSSSI |
| 52 | PRT | rabbit | AS7B82 HCDR2 KABAT | CIYAGSSSSIYYASWAKG |
| 53 | PRT | rabbit | AS7B82 HCDR2 CHOTHIA | YAGSSSS |
| 54 | PRT | rabbit | AS7B82 HCDR3 IMGT | ARGLFTSGSGYYIDM |
| 55 | PRT | rabbit | AS7B82 HCDR3 KABAT AND CHOTHIA | GLFTSGSGYYIDM |
| 56 | PRT | rabbit | AS7B82 LCDR1 IMGT | QSIGSD |
| 57 | PRT | rabbit | AS7B82 LCDR1 KABAT AND CHOTHIA | QASQSIGSNLA |
| 58 | PRT | rabbit | AS7B82 LCDR2 IMGT | SAS |
| 59 | PRT | rabbit | AS7B82 LCDR2 KABAT AND CHOTHIA | GASNLAA |
| 60 | PRT | rabbit | AS7B82 LCDR3 IMGT | QCTYSSSTGYNA |

| SEQ ID NO: | Type | Species | Description | Sequence |
|---|---|---|---|---|
| 61 | PRT | rabbit | AS7B82 LCDR3 KABAT AND CHOTHIA | QRGYISSAVDFFV |
| 62 | PRT | artificial | AS7B16-Heavy Chain | QVTLKESGPGILQPSQTLSLTCSFSGF SLNTSGTGVGWIRQPSGKGLEWLAHI WWDDDKGYNPALKSRLTISKNTSSN LVFLKIASVDTADTATYYCVRIKGR MDYWGQGTSVTVSSKTTPPSVYPLA PGSAAQTNSMVTLGCLVKGYFPEPV TVTWNSGSLSSGVHTFPAVLESDLYT LSSSVTVPSSPRPSETVTCNVAHPASS TKVDKKIVPRDCGCKPCICTVPEVSS VFIFPPKPKDVLTITLTPKVTCVVVDI SKDDPEVQFSWFVDDVEVHTAQTQP REEQFNSTFRSVSELPIMHQDWLNGK EFKCRVNSAAFPAPIEKTISKTKGRPK APQVYTIPPPKEQMAKDKVSLTCMIT DFFPEDITVEWQWNGQPAENYKNTQ PIMNTNGSYFVYSKLNVQKSNWEAG NTFTCSVLHEGLHNHHTEKSLSHSPGK |
| 63 | PRT | artificial | AS7B16-Light Chain | NIMMTQSPSSLAVSAGEKVTMNCKS SQSVLFGSKQKNYLAWYQQKPGQSP KLLIYWASTRESGVPDRFTGSGSGTD FILTISNVQAEDLAVYYCHQYLSLFTF GSGTKLEIKRADAAPTVSIFPPSSEQL TSGGASVVCFLNNFYPKDINVKWKI DGSERQNGVLNSWTDQDSKDSTYS MSSTLTLTKDEYERHNSYTCEATHK TSTSPIVKSFNRNEC |
| 64 | PRT | artificial | AS7B82-Heavy Chain | QEQQKESGGGLVKPGASLTLTCTAS GIDFSSVAYMCWVRQAPGKGLEWIA CIYAGSSSSIYYASWAKGRFTVSRTSS TTVTLQMTSLTAADTATYFCARGLF TSGSGYYIDMWGPGTLVTVSSASTK GPSVFPLAPSSKSTSGGTAALGCLVK DYFPEPVTVSWNSGALTSGVHTFPA VLQSSGLYSLSSVVTVPSSSLGTQTYI CNVNHKPSNTKVDKKVEPKSCDKTH TCPPCPAPELLGGPSVFLFPPKPKDTL MISRTPEVTCVVVDVSHEDPEVKFN WYVDGVEVHNAKTKPREEQYNSTY RVVSVLTVLHQDWLNGKEYKCKVS NKALPAPIEKTISKAKGQPREPQVYT LPPSRDELTKNQVSLTCLVKGFYPSDI AVEWESNGQPENNYKTTPPVLDSDG SFFLYSKLTVDKSRWQQGNVFSCSV MHEALHNHYTQKSLSLSPGK |
| 65 | PRT | artificial | AS7B82-Light Chain | DVVMTQTPSSVEVAVGGTVTIKCQA SQSIGSNLAWYQQKPGQRPKLLIYGA SNLAAGVPSRFSGSGSGTQFTLTISDV ECADAATYYCQRGYISSAVDFFVFG GGTEVVVKGRTVAAPSVFIFPPSDEQ LKSGTASVVCLLNNFYPREAKVQWK VDNALQSGNSQESVTEQDSKDSTYS LSSTLTLSKADYEKHKVYACEVTHQ GLSSPVTKSFNRGEC |
| 66 | PRT | artificial | AS7B16 H-L scFv | QVTLKESGPGILQPSQTLSLTCSFSGF SLNTSGTGVGWIRQPSGKGLEWLAHI WWDDDKGYNPALKSRLTISKNTSSN LVFLKIASVDTADTATYYCVRIKGR MDYWGQGTSVTVSSGGGGSGGGGS GGGGSGGGGSNIMMTQSPSSLAVSA GEKVTMNCKSSQSVLFGSKQKNYLA WYQQKPGQSPKLLIYWASTRESGVP DRFTGSGSGTDFILTISNVQAEDLAV YYCHQYLSLFTFGSGTKLEIK |

Brief Description of the Sequence Listing

| SEQ ID NO: | Type | Species | Description | Sequence |
|---|---|---|---|---|
| 67 | PRT | artificial | AS7B82 H-L scFv | QEQQKESGGGLVKPGASLTLTCTAS GIDFSSVAYMCWVRQAPGKGLEWIA CIYAGSSSSIYYASWAKGRFTVSRTSS TTVTLQMTSLTAADTATYFCARGLF TSGSGYYIDMWGPGTLVTVSSGGGG GSGGGGSGGGGSGGGGSDVVMTQT PSSVEVAVGGTVTIKCQASQSIGSNL AWYQQKPGQRPKLLIYGASNLAAGV PSRFSGSGSGTQFTLTISDVECADAAT YYCQRGYISSAVDFFVFGGGTEVVV KG |
| 68 | PRT | artificial | AS7B16 H-L CAR ECD | QVTLKESGPGILQPSQTLSLTCSFSGF SLNTSGTGVGWIRQPSGKGLEWLAHI WWDDDKGYNPALKSRLTISKNTSSN LVFLKIASVDTADTATYYCVRIKGR MDYWGQGTSVTVSSGGGGSGGGGS GGGGSGGGGSNIMMTQSPSSLAVSA GEKVTMNCKSSQSVLFGSKQKNYLA WYQQKPGQSPKLLIYWASTRESGVP DRFTGSGSGTDFILTISNVQAEDLAV YYCHQYLSLFTFGSGTKLEIKTTTPAP RPPTPAPTIASQPLSLRPEACRPAAGG AVHTRGLDFACDIYIWAPLAGTCGV LLLSLVITLYCKRGRKKLLYIFKQPF MRPVQTTQEEDGCSCRFPEEEEGGCE LRVKFSRSADAPAYKQGQNQLYNEL NLGRREEYDVLDKRRGRDPEMGGKP RRKNPQEGLYNELQKDKMAEAYSEI GMKGERRRGKGHDGLYQGLSTATK DTYDALHMQALPPR |
| 69 | PRT | artificial | AS7B16L-H CAR ECD | NIMMTQSPSSLAVSAGEKVTMNCKS SQSVLFGSKQKNYLAWYQQKPGQSP KLLIYWASTRESGVPDRFTGSGSGTD FILTISNVQAEDLAVYYCHQYLSLFTF GSGTKLEIKGGGGSGGGGSGGGGSG GGGSQVTLKESGPGILQPSQTLSLTCS FSGFSLNTSGTGVGWIRQPSGKGLEW LAHIWWDDDKGYNPALKSRLTISKN TSSNLVFLKIASVDTADTATYYCVRI KGRMDYWGQGTSVTVSSTTTPAPRP PTPAPTIASQPLSLRPEACRPAAGGAV HTRGLDFACDIYIWAPLAGTCGVLLL SLVITLYCKRGRKKLLYIFKQPFMRP VQTTQEEDGCSCRFPEEEEGGCELRV KFSRSADAPAYKQGQNQLYNELNLG RREEYDVLDKRRGRDPEMGGKPRRK NPQEGLYNELQKDKMAEAYSEIGMK GERRRGKGHDGLYQGLSTATKDTYD ALHMQALPPR |
| 70 | PRT | artificial | AS7B82 H-L CAR ECD | QEQQKESGGGLVKPGASLTLTCTAS GIDFSSVAYMCWVRQAPGKGLEWIA CIYAGSSSSIYYASWAKGRFTVSRTSS TTVTLQMTSLTAADTATYFCARGLF TSGSGYYIDMWGPGTLVTVSSGGGG GSGGGGSGGGGSGGGGSDVVMTQT PSSVEVAVGGTVTIKCQASQSIGSNL AWYQQKPGQRPKLLIYGASNLAAGV PSRFSGSGSGTQFTLTISDVECADAAT YYCQRGYISSAVDFFVFGGGTEVVV KGTTTPAPRPPTPAPTIASQPLSLRPE ACRPAAGGAVHTRGLDFACDIYIWA PLAGTCGVLLLSLVITLYCKRGRKKL LYIFKQPFMRPVQTTQEEDGCSCRFP EEEEGGCELRVKFSRSADAPAYKQG QNQLYNELNLGRREEYDVLDKRRGR DPEMGGKPRRKNPQEGLYNELQKDK MAEAYSEIGMKGERRRGKGHDGLY QGLSTATKDTYDALHMQALPPR |

| SEQ ID NO: | Type | Species | Description | Sequence |
|---|---|---|---|---|
| 71 | PRT | artificial | AS7B82L-H CAR ECD | DVVMTQTPSSVEVAVGGTVTIKCQA SQSIGSNLAWYQQKPGQRPKLLIYGA SNLAAGVPSRFSGSGSGTQFTLTISDV ECADAATYYCQRGYISSAVDFFVFG GGTEVVVKGGGGGSGGGGSGGGG SGGGGSEQQKESGGGLVKPGASLTL TCTASGIDFSSVAYMCWVRQAPGKG LEWIACIYAGSSSSIYYASWAKGRFT VSRTSSTTVTLQMTSLTAADTATYFC ARGLFTSGSGYYIDMWGPGTLVTVS STTTPAPRPPTPAPTIASQPLSLRPEAC RPAAGGAVHTRGLDFACDIYIWAPL AGTCGVLLLSLVITLYCKRGRKKLLY IFKQPFMRPVQTTQEEDGCSCRFPEE EEGGCELRVKFSRSADAPAYKQGQN QLYNELNLGRREEYDVLDKRRGRDP EMGGKPRRKNPQEGLYNELQKDKM AEAYSEIGMKGERRGKGHDGLYQG LSTATKDTYDALHMQALPPR |
| 72 | PRT | artificial | AS7B91 H-L CAR ECD | QSLEESGGRLVTPGTPLTLTCTVSGID LSTSVMGWVRQAPGKGLESIGFIYTN VNTYYASWAKGRFTISRTSTTVDLKI TSPTTGDTATYFCARAVYAGAMDL WGQGTLVTVSSGGGGSGGGGSGGG GSGGGGSDVVMTQTPASVSGPVGGT VTIKCQASERIYSNLAWYQQKPGQPP KLLIYKASTLASGVSSRFKGSGSGTEF TLTIRDLECADAATYSCQYTSYGSGY VGTFGGGTEVVVEG |
| 73 | PRT | artificial | AS7B91L-H CAR ECD | DVVMTQTPASVSGPVGGTVTIKCQA SERIYSNLAWYQQKPGQPPKLLIYKA STLASGVSSRFKGSGSGTEFTLTIRDL ECADAATYSCQYTSYGSGYVGTFGG GTEVVVEGGGGGSGGGGSGGGGSG GGGSLEESGGRLVTPGTPLTLTCTVS GIDLSTSVMGWVRQAPGKGLESIGFI YTNVNTYYASWAKGRFTISRTSTTV DLKITSPTTGDTATYFCARAVYAGA MDLWGQGTLVTVSS |
| 74 | PRT | artificial | AS7B16 VH | QVTLKESGPGILQPSQTLSLTCSFSGF SLNTSGTGVGWIRQPSGKGLEWLAHI WWDDDKGYNPALKSRLTISKNTSSN LVFLKIASVDTADTATYYCVRIKGR MDYWGQGTSVTVSS |
| 75 | PRT | artificial | AS7B16 VL | NIMMTQSPSSLAVSAGEKVTMNCKS SQSVLFGSKQKNYLAWYQQKPGQSP KLLIYWASTRESGVPDRFTGSGSGTD FILTISNVQAEDLAVYYCHQYLSLFTF GSGTKLEIK |
| 76 | DNA | artificial | AS7B16 VH | AGGTTACTCTGAAAGAGTCTGGCCC TGGGATATTGCAGCCCTCCCAGACC CTCAGTCTGACTTGTTCTTTCTCTGG GTTTTCACTGAACACTTCTGGTACG GGTGTAGGCTGGATTCGTCAGCCTT CAGGGAAGGGTCTGGAGTGGCTGG CACACATTTGGTGGGATGATGACA AGGGGTATAACCCAGCCCTGAAGA GCCGACTGACAATCTCCAAAAACA CCTCCAGCAACCTGGTATTCCTCAA GATCGCCAGTGTGGACACTGCAGA TACTGCCACATATTACTGTGTTCGA ATCAAAGGCCGGATGGACTACTGG GGTCAAGGAACCCTCAGTCACCGTCT CCTCA |
| 77 | DNA | artificial | AS7B16 VL | AACATTATGATGACACAGTCGCCAT CCTCTCTGGCTGTGTCTGCAGGAGA AAAGGTCACTATGAACTGTAAGTC |

-continued

Brief Description of the Sequence Listing

| SEQ ID NO: | Type | Species | Description | Sequence |
|---|---|---|---|---|
| | | | | CAGTCAAAGTGTTTTATTCGGTTCA AAACAGAAGAACTATTTGGCCTGG TACCAGCAGAAACCAGGGCAGTCT CCTAAATTGCTGATCTACTGGGCAT CCACTAGGGAATCTGGTGTCCCTGA TCGCTTCACAGGCAGTGGATCTGGG ACAGATTTTATACTTACCATCAGCA ATGTACAAGCTGAAGACCTGGCAG TTTATTACTGTCATCAATACCTCTC CCTATTCACGTTCGGCTCGGGGACA AAGTTGGAAATAAAA |
| 78 | PRT | artificial | AS7B82 VH | QEQQKESGGGLVKPGASLTLTCTAS GIDFSSVAYMCWVRQAPGKGLEWIA CIYAGSSSSIYYASWAKGRFTVSRTSS TTVTLQMTSLTAADTATYFCARGLF TSGSGYYIDMWGPGTLVTVSS |
| 79 | PRT | artificial | AS7B82 VL | DVVMTQTPSSVEVAVGGTVTIKCQA SQSIGSNLAWYQQKPGQRPKLLIYGA SNLAAGVPSRFSGSGSGTQFTLTISDV ECADAATYYCQRGYISSAVDFFVFG GGTEVVVKG |
| 80 | DNA | artificial | AS7B16 VH | CAGGAGCAGCAGAAGGAGTCCGGG GGAGGCCTGGTCAAGCCTGGGGCA TCCCTGACACTCACCTGCACAGCTT CTGGAATCGACTTCAGTAGTGTCGC CTACATGTGTTGGGTCCGCCAGGCT CCAGGGAAGGGGCTGGAGTGGATC GCATGCATTTATGCTGGTAGTAGTA GTAGCATCTACTACGCGAGCTGGG CGAAAGGCCGATTCACCGTCTCCA GAACCTCGTCTACCACGGTGACTCT GCAAATGACCAGTCTGACAGCCGC GGACACGGCCACCTATTTCTGTGCG AGAGGTCTATTTACTAGTGGTAGTG GATATTATATAGACATGTGGGGCCC AGGCACCCTGGTCACCGTCTCCTCA |
| 81 | DNA | artificial | AS7B16 VL | GATGTCGTGATGACCCAGACTCCAT CCTCTGTGGAGGTAGCTGTGGGAG GCACAGTCACCATCAAGTGCCAGG CCAGTCAGAGCATTGGTAGTAATTT AGCCTGGTATCAGCAGAAACCAGG GCAGCGTCCCAAGCTCCTGATCTAT GGTGCATCCAATCTGGCCGCTGGG GTCCCATCGCGGTTCAGTGGCAGTG GATCTGGGACACAGTTCACTCTCAC CATCAGCGACGTGGAGTGTGCCGA TGCTGCCACTTACTACTGTCAACGG GGTTATATTAGCAGTGCTGTTGATT TTTTTGTTTTCGGCGGAGGGACCGA GGTGGTGGTCAAAGGT |

REFERENCES

Ausubel et al., eds, 1994, Current Protocols in Molecular Biology, Vol. 1, John Wiley & Sons, Inc., New York
Bardenheuer et al., Leukemia. 2005 December; 19(12): 2281-8
Barnes et al, Anal. Biochem. 102:255 (1980)
Bork and Doolittle, PNAS USA 89:8990-8992, 1992
Chothia et al., J. Mol. Biol. 196:901 (1987)
Chothia et al., "Conformations of Immunoglobulin Hypervariable Regions," I 342:877 (1989)
Connell, Curr Opin Biotechnol. 2001 (5):446-9
Ham et al, Meth. Enz. 58:44 (1979)
Holt et al; Trends Biotechnol. 2003 November; 21(11):484-90
Jacobs et al., Protein Engineering, Design, and Selection, 25:107-117, 2012
Kabat et al., Sequences of Proteins of Immunological Interest, 5th ed. NIH Publication No. 91-3242 (1991)
Kushman et al., Carcinogenesis. 2007 January; 28(1):207-14
Luckow and Summers, Bio/Technology, 6:47, 1988
Makrides et al. Microbiol Rev. 1996 60(3):512-38
Mayfield et al., PNAS USA. 2003 100(2):438-42
MacCallum et al., J. Mol. Biol. 262:732 (1996)
Martin and Thornton, J. Mol. Biol. 263:800 (1996)
Meinke et al., J Bacteriol 175:1910-1918, 1993
E. Meyers and W. Miller, Comput. Appl. Biosci 4, 11-17 (1988)
Needleman and Wunsch, J. Mol. Biol. 48, 444-453 (1970)

Nivens et al, Cancer Chemother Pharmacol. 2004 February; 53(2):107-15
Patel et al., Gene Therapy, 1999; 6: 412-419
Revets et al; Expert Opin Biol Ther. 2005 January; 5(1): 111-24
Sambrook et al., Molecular Cloning: A Laboratory Manual, Vols. 1-3, Cold Spring Harbor Laboratory Press, 2 ed., 1989
Sharp et al. Yeast. 1991 7(7):657-78.
Sinclair et al. Protein Expr Purif. 2002 (1):96-105 Solid Phase Peptide Synthesis, 2nd ed., 1984, The Pierce Chemical Co., Rockford, Ill.
Sugimoto et al, J Gene Med. 2003 May; 5(5):366-76
Takebe et al., Mol Ther. 2001 January; 3(1):88-96
Ward et al., Nature 341, 544-546 (1989)),
Watanabe et al., J Biol Chem 265:15659-15665, 1990
Zielske et al., J Clin Invest. 2003 November; 112(10):1561-70
US2010/0216708
US2013/0226834
US2011/0274623
U.S. Pat. No. 4,767,704
U.S. Pat. No. 4,657,866
U.S. Pat. No. 4,927,762
U.S. Pat. No. 4,560,655
U.S. Pat. No. 5,122,469
WO90/03430
WO87/00195
USRE30985
WO 2013/176915
WO2014/130635
WO2013/176916
WO2013/176915
WO2014/039523
WO2014/184741
WO2014/191128
WO2014/184744
WO2014/184143
U.S. Pat. No. 6,352,694
U.S. Pat. No. 6,534,055
U.S. Pat. No. 6,905,680
U.S. Pat. No. 6,692,964
U.S. Pat. No. 5,858,358
U.S. Pat. No. 6,887,466
U.S. Pat. No. 6,905,681
U.S. Pat. No. 7,144,575
U.S. Pat. No. 7,067,318
U.S. Pat. No. 7,172,869
U.S. Pat. No. 7,232,566
U.S. Pat. No. 7,175,843
U.S. Pat. No. 5,883,223
U.S. Pat. No. 6,905,874
U.S. Pat. No. 6,797,514
U.S. Pat. No. 6,867,041
US2006/121005
U.S. Pat. No. 6,040,177
U.S. Pat. No. 5,827,642
WO2012129514

We claim:

1. A chimeric antigen receptor (CAR) comprising:
   (a) an extracellular domain comprising an scFv comprising the amino acid sequence of SEQ ID NOs: 72 or 73, wherein the extracellular domain specifically binds to a non-randomized region of an FN3 domain;
   (b) a transmembrane domain comprising the amino acid sequence of SEQ ID NO: 25; and
   (c) an intracellular signaling domain comprising a co-stimulatory domain comprising the amino acid sequence of SEQ ID NO: 26, and a primary signaling domain comprising the amino acid sequence of SEQ ID NO: 27, wherein the CAR optionally further comprises a hinge region comprising the amino acid sequence of SEQ ID NO: 24 connecting the extracellular domain and the transmembrane domain.

* * * * *

```
                        SEQUENCE LISTING

<160> NUMBER OF SEQ ID NOS: 93

<210> SEQ ID NO 1
<211> LENGTH: 8
<212> TYPE: PRT
<213> ORGANISM: Oryctolagus cuniculus

<400> SEQUENCE: 1

Gly Ile Asp Leu Ser Thr Ser Val
1               5

<210> SEQ ID NO 2
<211> LENGTH: 5
<212> TYPE: PRT
<213> ORGANISM: Oryctolagus cuniculus

<400> SEQUENCE: 2

Thr Ser Val Met Gly
1               5

<210> SEQ ID NO 3
<211> LENGTH: 7
<212> TYPE: PRT
<213> ORGANISM: Oryctolagus cuniculus

<400> SEQUENCE: 3

Gly Ile Asp Leu Ser Thr Ser
1               5

<210> SEQ ID NO 4
<211> LENGTH: 7
<212> TYPE: PRT
<213> ORGANISM: Oryctolagus cuniculus

<400> SEQUENCE: 4
```

Ile Tyr Thr Asn Val Asn Thr
1               5

<210> SEQ ID NO 5
<211> LENGTH: 16
<212> TYPE: PRT
<213> ORGANISM: Oryctolagus cuniculus

<400> SEQUENCE: 5

Phe Ile Tyr Thr Asn Val Asn Thr Tyr Tyr Ala Ser Trp Ala Lys Gly
1               5                   10                  15

<210> SEQ ID NO 6
<211> LENGTH: 5
<212> TYPE: PRT
<213> ORGANISM: Oryctolagus cuniculus

<400> SEQUENCE: 6

Tyr Thr Asn Val Asn
1               5

<210> SEQ ID NO 7
<211> LENGTH: 11
<212> TYPE: PRT
<213> ORGANISM: Oryctolagus cuniculus

<400> SEQUENCE: 7

Ala Arg Ala Val Tyr Ala Gly Ala Met Asp Leu
1               5                   10

<210> SEQ ID NO 8
<211> LENGTH: 9
<212> TYPE: PRT
<213> ORGANISM: Oryctolagus cuniculus

<400> SEQUENCE: 8

Ala Val Tyr Ala Gly Ala Met Asp Leu
1               5

<210> SEQ ID NO 9
<211> LENGTH: 6
<212> TYPE: PRT
<213> ORGANISM: Oryctolagus cuniculus

<400> SEQUENCE: 9

Glu Arg Ile Tyr Ser Asn
1               5

<210> SEQ ID NO 10
<211> LENGTH: 11
<212> TYPE: PRT
<213> ORGANISM: Oryctolagus cuniculus

<400> SEQUENCE: 10

Gln Ala Ser Glu Arg Ile Tyr Ser Asn Leu Ala
1               5                   10

<210> SEQ ID NO 11
<211> LENGTH: 3
<212> TYPE: PRT
<213> ORGANISM: Oryctolagus cuniculus

<400> SEQUENCE: 11

Lys Ala Ser

<210> SEQ ID NO 12
<211> LENGTH: 7
<212> TYPE: PRT
<213> ORGANISM: Oryctolagus cuniculus

<400> SEQUENCE: 12

Lys Ala Ser Thr Leu Ala Ser
1               5

<210> SEQ ID NO 13
<211> LENGTH: 12
<212> TYPE: PRT
<213> ORGANISM: Oryctolagus cuniculus

<400> SEQUENCE: 13

Gln Tyr Thr Ser Tyr Gly Ser Gly Tyr Val Gly Thr
1               5                   10

<210> SEQ ID NO 14
<211> LENGTH: 114
<212> TYPE: PRT
<213> ORGANISM: Oryctolagus cuniculus

<400> SEQUENCE: 14

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Thr Ser Val
            20                  25                  30

Met Gly Trp Val Arg Gln Ala Pro Gly Lys Gly Leu Glu Ser Ile Gly
        35                  40                  45

Phe Ile Tyr Thr Asn Val Asn Thr Tyr Tyr Ala Ser Trp Ala Lys Gly
    50                  55                  60

Arg Phe Thr Ile Ser Arg Thr Ser Thr Thr Val Asp Leu Lys Ile Thr
65                  70                  75                  80

Ser Pro Thr Thr Gly Asp Thr Ala Thr Tyr Phe Cys Ala Arg Ala Val
                85                  90                  95

Tyr Ala Gly Ala Met Asp Leu Trp Gly Gln Gly Thr Leu Val Thr Val
            100                 105                 110

Ser Ser

<210> SEQ ID NO 15
<211> LENGTH: 111
<212> TYPE: PRT
<213> ORGANISM: Oryctolagus cuniculus

<400> SEQUENCE: 15

Asp Val Val Met Thr Gln Thr Pro Ala Ser Val Ser Gly Pro Val Gly
1               5                   10                  15

Gly Thr Val Thr Ile Lys Cys Gln Ala Ser Glu Arg Ile Tyr Ser Asn
            20                  25                  30

Leu Ala Trp Tyr Gln Gln Lys Pro Gly Gln Pro Pro Lys Leu Leu Ile
        35                  40                  45

Tyr Lys Ala Ser Thr Leu Ala Ser Gly Val Ser Ser Arg Phe Lys Gly
    50                  55                  60

Ser Gly Ser Gly Thr Glu Phe Thr Leu Thr Ile Arg Asp Leu Glu Cys
65                  70                  75                  80

Ala Asp Ala Ala Thr Tyr Ser Cys Gln Tyr Thr Ser Tyr Gly Ser Gly 85                  90                  95
Tyr Val Gly Thr Phe Gly Gly Gly Thr Glu Val Val Glu Gly
            100                 105                 110

<210> SEQ ID NO 16
<211> LENGTH: 336
<212> TYPE: DNA
<213> ORGANISM: Oryctolagus cuniculus

<400> SEQUENCE: 16
ctggaggagt ccggggggtcg cctggtcacg cctgggacac ccctgacact cacctgcaca    60
gtctctggaa tcgacctcag tacctctgtc atgggttggg tccgccaggc tccaggaag    120 gggctggaat ccatcggatt catttatact aatgttaaca catactacgc gagctgggca    180
aaaggccgat tcaccatctc cagaacctcg accacggtgg atctgaaaat caccagtccg    240
acaaccgggg acacggccac ctatttctgt gccagagctg tttatgctgg tgctatggac    300
ttgtggggcc aaggcaccct ggtcaccgtc tcctca                              336

<210> SEQ ID NO 17
<211> LENGTH: 333
<212> TYPE: DNA
<213> ORGANISM: Oryctolagus cuniculus

<400> SEQUENCE: 17
gatgttgtga tgacccagac tccagcctcc gtgtctggac ctgtgggagg cacagtcacc    60
atcaagtgcc aggccagtga gaaatttat agcaatttag cctggtatca gcagaaacca    120
gggcagcctc ccaaactcct gatctacaag gcatccactc tggcatctgg ggtctcatcg    180
cggttcaaag gcagtggatc tgggacagag ttcactctca ccatcaggga ccttgagtgt    240
gccgatgctg ccacttactc ctgtcaatat acttcttatg cagtggtta tgttggtact    300 ttcggcggag ggaccgaggt ggtggtcgaa ggt                                 333

<210> SEQ ID NO 18
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Thr Ser Val
            20                  25                  30

Met Gly Trp Val Arg Gln Ala Pro Gly Lys Gly Leu Glu Ser Ile Gly
        35                  40                  45

Phe Ile Tyr Thr Asn Val Asn Thr Tyr Tyr Ala Ser Trp Ala Lys Gly
    50                  55                  60

Arg Phe Thr Ile Ser Arg Thr Ser Thr Val Asp Leu Lys Ile Thr
65                  70                  75                  80

Ser Pro Thr Thr Gly Asp Thr Ala Thr Tyr Phe Cys Ala Arg Ala Val
                85                  90                  95

Tyr Ala Gly Ala Met Asp Leu Trp Gly Gln Gly Thr Leu Val Thr Val
            100                 105                 110

Ser Ser Ala Lys Thr Thr Ala Pro Ser Val Tyr Pro Leu Ala Pro Val
        115                 120                 125

Cys Gly Asp Thr Thr Gly Ser Ser Val Thr Leu Gly Cys Leu Val Lys
            130                 135                 140

Gly Tyr Phe Pro Glu Pro Val Thr Leu Thr Trp Asn Ser Gly Ser Leu
145                 150                 155                 160

Ser Ser Gly Val His Thr Phe Pro Ala Val Leu Gln Ser Asp Leu Tyr
                165                 170                 175

Thr Leu Ser Ser Ser Val Thr Val Thr Ser Ser Thr Trp Pro Ser Gln
            180                 185                 190

Ser Ile Thr Cys Asn Val Ala His Pro Ala Ser Ser Thr Lys Val Asp
        195                 200                 205

Lys Lys Ile Glu Pro Arg Gly Pro Thr Ile Lys Pro Cys Pro Pro Cys
210                 215                 220

Lys Cys Pro Ala Pro Asn Leu Leu Gly Gly Pro Ser Val Phe Ile Phe
225                 230                 235                 240

Pro Pro Lys Ile Lys Asp Val Leu Met Ile Ser Leu Ser Pro Ile Val
                245                 250                 255

Thr Cys Val Val Val Asp Val Ser Glu Asp Asp Pro Asp Val Gln Ile
            260                 265                 270

Ser Trp Phe Val Asn Asn Val Glu Val His Thr Ala Gln Thr Gln Thr
        275                 280                 285

His Arg Glu Asp Tyr Asn Ser Thr Leu Arg Val Val Ser Ala Leu Pro
290                 295                 300

Ile Gln His Gln Asp Trp Met Ser Gly Lys Glu Phe Lys Cys Lys Val
305                 310                 315                 320

Asn Asn Lys Asp Leu Pro Ala Pro Ile Glu Arg Thr Ile Ser Lys Pro
                325                 330                 335

Lys Gly Ser Val Arg Ala Pro Gln Val Tyr Val Leu Pro Pro Pro Glu
            340                 345                 350

Glu Glu Met Thr Lys Lys Gln Val Thr Leu Thr Cys Met Val Thr Asp
        355                 360                 365

Phe Met Pro Glu Asp Ile Tyr Val Glu Trp Thr Asn Asn Gly Lys Thr
370                 375                 380

Glu Leu Asn Tyr Lys Asn Thr Glu Pro Val Leu Asp Ser Asp Gly Ser
385                 390                 395                 400

Tyr Phe Met Tyr Ser Lys Leu Arg Val Glu Lys Lys Asn Trp Val Glu
                405                 410                 415

Arg Asn Ser Tyr Ser Cys Ser Val Val His Glu Gly Leu His Asn His
            420                 425                 430

His Thr Thr Lys Ser Phe Ser Arg Thr Pro Gly Lys
        435                 440

<210> SEQ ID NO 19
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Val Val Met Thr Gln Thr Pro Ala Ser Val Ser Gly Pro Val Gly
1               5                   10                  15

Gly Thr Val Thr Ile Lys Cys Gln Ala Ser Glu Arg Ile Tyr Ser Asn
            20                  25                  30

Leu Ala Trp Tyr Gln Gln Lys Pro Gly Gln Pro Pro Lys Leu Leu Ile

-continued

```
                35                  40                  45
Tyr Lys Ala Ser Thr Leu Ala Ser Gly Val Ser Ser Arg Phe Lys Gly
 50                  55                  60
Ser Gly Ser Gly Thr Glu Phe Thr Leu Thr Ile Arg Asp Leu Glu Cys
 65                  70                  75                  80
Ala Asp Ala Ala Thr Tyr Ser Cys Gln Tyr Thr Ser Tyr Gly Ser Gly
                 85                  90                  95
Tyr Val Gly Thr Phe Gly Gly Gly Thr Glu Val Val Glu Gly Arg
                100                 105                 110
Ala Asp Ala Ala Pro Thr Val Ser Ile Phe Pro Pro Ser Ser Glu Gln
                115                 120                 125
Leu Thr Ser Gly Gly Ala Ser Val Val Cys Phe Leu Asn Asn Phe Tyr
            130                 135                 140
Pro Lys Asp Ile Asn Val Lys Trp Lys Ile Asp Gly Ser Glu Arg Gln
145                 150                 155                 160
Asn Gly Val Leu Asn Ser Trp Thr Asp Gln Asp Ser Lys Asp Ser Thr
                165                 170                 175
Tyr Ser Met Ser Ser Thr Leu Thr Leu Thr Lys Asp Glu Tyr Glu Arg
                180                 185                 190
His Asn Ser Tyr Thr Cys Glu Ala Thr His Lys Thr Ser Thr Ser Pro
            195                 200                 205
Ile Val Lys Ser Phe Asn Arg Asn Glu Cys
210                 215
```

<210> SEQ ID NO 20
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Gln Ser Leu Glu Glu Ser Gly Gly Arg Leu Val Thr Pro Gly Thr Pro
 1               5                  10                  15
Leu Thr Leu Thr Cys Thr Val Ser Gly Ile Asp Leu Ser Thr Ser Val
                20                  25                  30
Met Gly Trp Val Arg Gln Ala Pro Gly Lys Gly Leu Glu Ser Ile Gly
            35                  40                  45
Phe Ile Tyr Thr Asn Val Asn Thr Tyr Tyr Ala Ser Trp Ala Lys Gly
 50                  55                  60
Arg Phe Thr Ile Ser Arg Thr Ser Thr Thr Val Asp Leu Lys Ile Thr
 65                  70                  75                  80
Ser Pro Thr Thr Gly Asp Thr Ala Thr Tyr Phe Cys Ala Arg Ala Val
                 85                  90                  95
Tyr Ala Gly Ala Met Asp Leu Trp Gly Gln Gly Thr Leu Val Thr Val
                100                 105                 110
Ser Ser Ala Glu Thr Thr Ala Pro Ser Val Tyr Pro Leu Ala Pro Gly
            115                 120                 125
Thr Ala Leu Lys Ser Asn Ser Met Val Thr Leu Gly Cys Leu Val Lys
        130                 135                 140
Gly Tyr Phe Pro Glu Pro Val Thr Val Thr Trp Asn Ser Gly Ala Leu
145                 150                 155                 160
Ser Ser Gly Val His Thr Phe Pro Ala Val Leu Gln Ser Gly Leu Tyr
                165                 170                 175
```

Thr Leu Thr Ser Ser Val Thr Val Pro Ser Ser Thr Trp Pro Ser Gln
            180                 185                 190

Thr Val Thr Cys Asn Val Ala His Pro Ala Ser Ser Thr Lys Val Asp
            195                 200                 205

Lys Lys Ile Val Pro Arg Asn Cys Gly Gly Asp Cys Lys Pro Cys Ile
            210                 215                 220

Cys Thr Gly Ser Glu Val Ser Ser Val Phe Ile Phe Pro Pro Lys Pro
225                 230                 235                 240

Lys Asp Val Leu Thr Ile Thr Leu Thr Pro Lys Val Thr Cys Val Val
            245                 250                 255

Val Asp Ile Ser Gln Asp Asp Pro Glu Val His Phe Ser Trp Phe Val
            260                 265                 270

Asp Asp Val Glu Val His Thr Ala Gln Thr Arg Pro Pro Glu Glu Gln
            275                 280                 285

Phe Asn Ser Thr Phe Arg Ser Val Ser Glu Leu Pro Ile Leu His Gln
            290                 295                 300

Asp Trp Leu Asn Gly Arg Thr Phe Arg Cys Lys Val Thr Ser Ala Ala
305                 310                 315                 320

Phe Pro Ser Pro Ile Glu Lys Thr Ile Ser Lys Pro Glu Gly Arg Thr
            325                 330                 335

Gln Val Pro His Val Tyr Thr Met Ser Pro Thr Lys Glu Glu Met Thr
            340                 345                 350

Gln Asn Glu Val Ser Ile Thr Cys Met Val Lys Gly Phe Tyr Pro Pro
            355                 360                 365

Asp Ile Tyr Val Glu Trp Gln Met Asn Gly Gln Pro Gln Glu Asn Tyr
370                 375                 380

Lys Asn Thr Pro Pro Thr Met Asp Thr Asp Gly Ser Tyr Phe Leu Tyr
385                 390                 395                 400

Ser Lys Leu Asn Val Lys Lys Glu Lys Trp Gln Gln Gly Asn Thr Phe
            405                 410                 415

Thr Cys Ser Val Leu His Glu Gly Leu His Asn His His Thr Glu Lys
            420                 425                 430

Ser Leu Ser His Ser Pro Gly Lys
            435                 440

<210> SEQ ID NO 21
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Val Val Met Thr Gln Thr Pro Ala Ser Val Ser Gly Pro Val Gly
1               5                   10                  15

Gly Thr Val Thr Ile Lys Cys Gln Ala Ser Glu Arg Ile Tyr Ser Asn
            20                  25                  30

Leu Ala Trp Tyr Gln Gln Lys Pro Gly Gln Pro Pro Lys Leu Leu Ile
            35                  40                  45

Tyr Lys Ala Ser Thr Leu Ala Ser Gly Val Ser Ser Arg Phe Lys Gly
            50                  55                  60

Ser Gly Ser Gly Thr Glu Phe Thr Leu Thr Ile Arg Asp Leu Glu Cys
65                  70                  75                  80

Ala Asp Ala Ala Thr Tyr Ser Cys Gln Tyr Thr Ser Tyr Gly Ser Gly
            85                  90                  95

-continued

```
Tyr Val Gly Thr Phe Gly Gly Thr Glu Val Val Glu Gly Arg
            100                 105                 110

Ala Asp Ala Ala Pro Thr Val Ser Ile Phe Pro Pro Ser Glu Gln
            115                 120                 125

Leu Ala Ser Gly Gly Ala Ser Val Val Cys Phe Ile Asn Lys Phe Tyr
            130                 135                 140

Pro Lys Asp Ile Ser Val Lys Trp Lys Ile Asp Gly Ser Glu Arg Gln
145                 150                 155                 160

Asn Asp Val Leu Asn Ser Val Thr Asp Gln Asp Ser Lys Asp Ser Thr
                165                 170                 175

Tyr Ser Met Ser Ser Thr Leu Thr Leu Thr Lys Ala Asp Tyr Glu Arg
                180                 185                 190

His Asn Leu Tyr Thr Cys Glu Val Val His Lys Thr Ser Ala Ser Pro
                195                 200                 205

Val Val Lys Ser Phe Asn Arg Asn Glu Cys
            210                 215

<210> SEQ ID NO 22
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
                20                  25                  30

Gly Thr Pro Leu Thr Leu Thr Cys Thr Val Ser Gly Ile Asp Leu Ser
            35                  40                  45

Thr Ser Val Met Gly Trp Val Arg Gln Ala Pro Gly Lys Gly Leu Glu
    50                  55                  60

Ser Ile Gly Phe Ile Tyr Thr Asn Val Asn Thr Tyr Tyr Ala Ser Trp
65                  70                  75                  80

Ala Lys Gly Arg Phe Thr Ile Ser Arg Thr Ser Thr Val Asp Leu
                85                  90                  95

Lys Ile Thr Ser Pro Thr Thr Gly Asp Thr Ala Thr Tyr Phe Cys Ala
            100                 105                 110

Arg Ala Val Tyr Ala Gly Ala Met Asp Leu Trp Gly Gln Gly Thr Leu
            115                 120                 125

Val Thr Val Ser Ser Gly Gly Gly Gly Ser Gly Gly Gly Ser Gly
            130                 135                 140

Gly Gly Gly Ser Gly Gly Gly Gly Ser Asp Val Val Met Thr Gln Thr
145                 150                 155                 160

Pro Ala Ser Val Ser Gly Pro Val Gly Gly Thr Val Thr Ile Lys Cys
                165                 170                 175

Gln Ala Ser Glu Arg Ile Tyr Ser Asn Leu Ala Trp Tyr Gln Gln Lys
                180                 185                 190

Pro Gly Gln Pro Pro Lys Leu Leu Ile Tyr Lys Ala Ser Thr Leu Ala
                195                 200                 205

Ser Gly Val Ser Ser Arg Phe Lys Gly Ser Gly Ser Gly Thr Glu Phe
            210                 215                 220

Thr Leu Thr Ile Arg Asp Leu Glu Cys Ala Asp Ala Ala Thr Tyr Ser
```

```
                    225                 230                 235                 240

Cys Gln Tyr Thr Ser Tyr Gly Ser Gly Tyr Val Gly Thr Phe Gly Gly
                245                 250                 255

Gly Thr Glu Val Val Val Glu Gly
        260
```

<210> SEQ ID NO 23
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Met Asp Thr Arg Ala Pro Thr Gln Leu Leu Gly Leu Leu Leu Leu Trp
1               5                   10                  15

Leu Pro Gly Ala Arg Cys Asp Val Val Met Thr Gln Thr Pro Ala Ser
                20                  25                  30

Val Ser Gly Pro Val Gly Gly Thr Val Thr Ile Lys Cys Gln Ala Ser
            35                  40                  45

Glu Arg Ile Tyr Ser Asn Leu Ala Trp Tyr Gln Gln Lys Pro Gly Gln
        50                  55                  60

Pro Pro Lys Leu Leu Ile Tyr Lys Ala Ser Thr Leu Ala Ser Gly Val
65                  70                  75                  80

Ser Ser Arg Phe Lys Gly Ser Gly Ser Gly Thr Glu Phe Thr Leu Thr
                85                  90                  95

Ile Arg Asp Leu Glu Cys Ala Asp Ala Ala Thr Tyr Ser Cys Gln Tyr
                100                 105                 110

Thr Ser Tyr Gly Ser Gly Tyr Val Gly Thr Phe Gly Gly Gly Thr Glu
            115                 120                 125

Val Val Val Glu Gly Gly Gly Gly Ser Gly Gly Gly Ser Gly
130                 135                 140

Gly Gly Gly Ser Gly Gly Gly Gly Ser Leu Glu Glu Ser Gly Gly Arg
145                 150                 155                 160

Leu Val Thr Pro Gly Thr Pro Leu Thr Leu Thr Cys Thr Val Ser Gly
                165                 170                 175

Ile Asp Leu Ser Thr Ser Val Met Gly Trp Val Arg Gln Ala Pro Gly
                180                 185                 190

Lys Gly Leu Glu Ser Ile Gly Phe Ile Tyr Thr Asn Val Asn Thr Tyr
            195                 200                 205

Tyr Ala Ser Trp Ala Lys Gly Arg Phe Thr Ile Ser Arg Thr Ser Thr
        210                 215                 220

Thr Val Asp Leu Lys Ile Thr Ser Pro Thr Thr Gly Asp Thr Ala Thr
225                 230                 235                 240

Tyr Phe Cys Ala Arg Ala Val Tyr Ala Gly Ala Met Asp Leu Trp Gly
                245                 250                 255

Gln Gly Thr Leu Val Thr Val Ser Ser
            260                 265
```

<210> SEQ ID NO 24
<211> LENGTH: 47
<212> TYPE: PRT
<213> ORGANISM: Homo sapiens

<400> SEQUENCE: 24

```
Thr Thr Thr Pro Ala Pro Arg Pro Pro Thr Pro Ala Pro Thr Ile Ala
```

```
                 1               5                  10                  15
Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr
                35                  40                  45

<210> SEQ ID NO 25
<211> LENGTH: 23
<212> TYPE: PRT
<213> ORGANISM: Homo sapiens

<400> SEQUENCE: 25

Ile Trp Ala Pro Leu Ala Gly Thr Cys Gly Val Leu Leu Leu Ser Leu
 1               5                  10                  15

Val Ile Thr Leu Tyr Cys Lys
                20

<210> SEQ ID NO 26
<211> LENGTH: 41
<212> TYPE: PRT
<213> ORGANISM: Homo sapiens

<400> SEQUENCE: 26

Arg Gly Arg Lys Lys Leu Leu Tyr Ile Phe Lys Gln Pro Phe Met Arg
 1               5                  10                  15

Pro Val Gln Thr Thr Gln Glu Glu Asp Gly Cys Ser Cys Arg Phe Pro
                20                  25                  30

Glu Glu Glu Glu Gly Gly Cys Glu Leu
            35                  40

<210> SEQ ID NO 27
<211> LENGTH: 112
<212> TYPE: PRT
<213> ORGANISM: Homo sapiens

<400> SEQUENCE: 27

Arg Val Lys Phe Ser Arg Ser Ala Asp Ala Pro Ala Tyr Lys Gln Gly
 1               5                  10                  15

Gln Asn Gln Leu Tyr Asn Glu Leu Asn Leu Gly Arg Arg Glu Glu Tyr
                20                  25                  30

Asp Val Leu Asp Lys Arg Gly Arg Asp Pro Glu Met Gly Gly Lys
            35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 28
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28
```

```
Leu Pro Ala Pro Lys Asn Leu Val Val Ser Glu Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Ile Phe Thr Thr
                85
```

<210> SEQ ID NO 29
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Met Leu Pro Ala Pro Lys Asn Leu Val Val Ser Glu Val Thr His Asp
1               5                   10                  15

Ser Ala Arg Leu Ser Trp Thr Ala Pro Asp Ala Ala Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys His
    50                  55                  60

His Thr Glu Tyr Thr Val Ser Ile Tyr Gly Val Lys Gly Gly His Arg
65                  70                  75                  80

Ser Asn Pro Leu Ser Ala Ile Phe His Thr His His His His His
                85                  90                  95
```

<210> SEQ ID NO 30
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Met Leu Pro Ala Pro Lys Asn Leu Val Val Ser Arg Val Thr His Asp
1               5                   10                  15

Ser Ala Arg Leu Ser Trp Thr Ala Pro Asp Ala Ala Phe Asp Ser Phe
            20                  25                  30

Trp Ile Arg Tyr Phe Glu Phe Leu Gly Ser Gly Glu Ala Ile Val Leu
        35                  40                  45

Thr Val Pro Gly Ser Glu Arg Ser Tyr Asp Leu Thr Gly Leu Lys His
    50                  55                  60

His Thr Glu Tyr Val Val Asn Ile Met Gly Val Lys Gly Gly Lys Ile
65                  70                  75                  80

Ser Pro Pro Leu Ser Ala Ile Phe Thr Thr His His His His His
                85                  90                  95
```

<210> SEQ ID NO 31
<211> LENGTH: 98

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Trp Ile Arg Tyr Phe Glu Phe Leu Gly Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Val Val Asn Ile Met Gly Val Lys Gly Gly Lys Ile
65                  70                  75                  80

Ser Pro Pro Leu Ser Ala Ile Phe Thr Thr Gly Gly His His His His
                85                  90                  95

His His

<210> SEQ ID NO 32
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Gly
                85                  90                  95

Gly Gly Gly Ser Gly Gly Gly Gly Ser Leu Ala Glu Ala Lys Val Leu
            100                 105                 110

Ala Asn Arg Glu Leu Asp Lys Tyr Gly Val Ser Asp Tyr Tyr Lys Asn
        115                 120                 125

Leu Ile Asn Asn Ala Lys Thr Val Glu Gly Val Lys Ala Leu Ile Asp
    130                 135                 140

Glu Ile Leu Ala Ala Leu Pro Gly Gly His His His His His His
145                 150                 155

<210> SEQ ID NO 33
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33
```

```
Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
                35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly His Arg Ser
65                  70                  75                  80

Asn Pro Leu Ser Ala Glu Phe Thr Thr
                85
```

<210> SEQ ID NO 34
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
                35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly His Arg Ser
65                  70                  75                  80

Asn Pro Leu Ser Ala Ile Phe Thr Thr
                85
```

<210> SEQ ID NO 35
<211> LENGTH: 10
<212> TYPE: PRT
<213> ORGANISM: Mus sp.

<400> SEQUENCE: 35

```
Gly Phe Ser Leu Asn Thr Ser Gly Thr Gly
1               5                   10
```

<210> SEQ ID NO 36
<211> LENGTH: 7
<212> TYPE: PRT
<213> ORGANISM: Mus sp.

<400> SEQUENCE: 36

```
Thr Ser Gly Thr Gly Val Gly
1               5
```

<210> SEQ ID NO 37
<211> LENGTH: 9
<212> TYPE: PRT
<213> ORGANISM: Mus sp.

<400> SEQUENCE: 37

Gly Phe Ser Leu Asn Thr Ser Gly Thr

<210> SEQ ID NO 38
<211> LENGTH: 9
<212> TYPE: PRT
<213> ORGANISM: Oryctolagus cuniculus

<400> SEQUENCE: 38

Gly Ile Asp Phe Ser Ser Val Ala Tyr
1               5

<210> SEQ ID NO 39
<211> LENGTH: 6
<212> TYPE: PRT
<213> ORGANISM: Oryctolagus cuniculus

<400> SEQUENCE: 39

Ser Val Ala Tyr Met Cys
1               5

<210> SEQ ID NO 40
<211> LENGTH: 8
<212> TYPE: PRT
<213> ORGANISM: Oryctolagus cuniculus

<400> SEQUENCE: 40

Gly Ile Asp Phe Ser Ser Val Ala
1               5

<210> SEQ ID NO 41
<211> LENGTH: 7
<212> TYPE: PRT
<213> ORGANISM: Mus sp.

<400> SEQUENCE: 41

Ile Trp Trp Asp Asp Asp Lys
1               5

<210> SEQ ID NO 42
<211> LENGTH: 16
<212> TYPE: PRT
<213> ORGANISM: Mus sp.

<400> SEQUENCE: 42

His Ile Trp Trp Asp Asp Asp Lys Gly Tyr Asn Pro Ala Leu Lys Ser
1               5                   10                  15

<210> SEQ ID NO 43
<211> LENGTH: 5
<212> TYPE: PRT
<213> ORGANISM: Mus sp.

<400> SEQUENCE: 43

Trp Trp Asp Asp Asp
1               5

<210> SEQ ID NO 44
<211> LENGTH: 9
<212> TYPE: PRT
<213> ORGANISM: Mus sp.

<400> SEQUENCE: 44

Val Arg Ile Lys Gly Arg Met Asp Tyr
1               5

```
<210> SEQ ID NO 45
<211> LENGTH: 7
<212> TYPE: PRT
<213> ORGANISM: Mus sp.

<400> SEQUENCE: 45

Ile Lys Gly Arg Met Asp Tyr
1               5

<210> SEQ ID NO 46
<211> LENGTH: 12
<212> TYPE: PRT
<213> ORGANISM: Mus sp.

<400> SEQUENCE: 46

Gln Ser Val Leu Phe Gly Ser Lys Gln Lys Asn Tyr
1               5                   10

<210> SEQ ID NO 47
<211> LENGTH: 17
<212> TYPE: PRT
<213> ORGANISM: Mus sp.

<400> SEQUENCE: 47

Lys Ser Ser Gln Ser Val Leu Phe Gly Ser Lys Gln Lys Asn Tyr Leu
1               5                   10                  15

Ala

<210> SEQ ID NO 48
<211> LENGTH: 3
<212> TYPE: PRT
<213> ORGANISM: Mus sp.

<400> SEQUENCE: 48

Trp Ala Ser
1

<210> SEQ ID NO 49
<211> LENGTH: 7
<212> TYPE: PRT
<213> ORGANISM: Mus sp.

<400> SEQUENCE: 49

Trp Ala Ser Thr Arg Glu Ser
1               5

<210> SEQ ID NO 50
<211> LENGTH: 8
<212> TYPE: PRT
<213> ORGANISM: Mus sp.

<400> SEQUENCE: 50

His Gln Tyr Leu Ser Leu Phe Thr
1               5

<210> SEQ ID NO 51
<211> LENGTH: 9
<212> TYPE: PRT
<213> ORGANISM: Oryctolagus cuniculus

<400> SEQUENCE: 51

Ile Tyr Ala Gly Ser Ser Ser Ser Ile
1               5
```

```
<210> SEQ ID NO 52
<211> LENGTH: 18
<212> TYPE: PRT
<213> ORGANISM: Oryctolagus cuniculus

<400> SEQUENCE: 52

Cys Ile Tyr Ala Gly Ser Ser Ser Ile Tyr Ala Ser Trp Ala
1               5                   10                  15
Lys Gly

<210> SEQ ID NO 53
<211> LENGTH: 7
<212> TYPE: PRT
<213> ORGANISM: Oryctolagus cuniculus

<400> SEQUENCE: 53

Tyr Ala Gly Ser Ser Ser Ser
1               5

<210> SEQ ID NO 54
<211> LENGTH: 15
<212> TYPE: PRT
<213> ORGANISM: Oryctolagus cuniculus

<400> SEQUENCE: 54

Ala Arg Gly Leu Phe Thr Ser Gly Ser Gly Tyr Tyr Ile Asp Met
1               5                   10                  15

<210> SEQ ID NO 55
<211> LENGTH: 13
<212> TYPE: PRT
<213> ORGANISM: Oryctolagus cuniculus

<400> SEQUENCE: 55

Gly Leu Phe Thr Ser Gly Ser Gly Tyr Tyr Ile Asp Met
1               5                   10

<210> SEQ ID NO 56
<211> LENGTH: 6
<212> TYPE: PRT
<213> ORGANISM: Oryctolagus cuniculus

<400> SEQUENCE: 56

Gln Ser Ile Gly Ser Asp
1               5

<210> SEQ ID NO 57
<211> LENGTH: 11
<212> TYPE: PRT
<213> ORGANISM: Oryctolagus cuniculus

<400> SEQUENCE: 57

Gln Ala Ser Gln Ser Ile Gly Ser Asn Leu Ala
1               5                   10

<210> SEQ ID NO 58
<211> LENGTH: 3
<212> TYPE: PRT
<213> ORGANISM: Oryctolagus cuniculus

<400> SEQUENCE: 58

Ser Ala Ser
1
```

<210> SEQ ID NO 59
<211> LENGTH: 7
<212> TYPE: PRT
<213> ORGANISM: Oryctolagus cuniculus

<400> SEQUENCE: 59

Gly Ala Ser Asn Leu Ala Ala
1               5

<210> SEQ ID NO 60
<211> LENGTH: 12
<212> TYPE: PRT
<213> ORGANISM: Oryctolagus cuniculus

<400> SEQUENCE: 60

Gln Cys Thr Tyr Ser Ser Ser Thr Gly Tyr Asn Ala
1               5                   10

<210> SEQ ID NO 61
<211> LENGTH: 13
<212> TYPE: PRT
<213> ORGANISM: Oryctolagus cuniculus

<400> SEQUENCE: 61

Gln Arg Gly Tyr Ile Ser Ser Ala Val Asp Phe Phe Val
1               5                   10

<210> SEQ ID NO 62
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Ser
            20                  25                  30

Gly Thr Gly Val Gly Trp Ile Arg Gln Pro Ser Gly Lys Gly Leu Glu
        35                  40                  45

Trp Leu Ala His Ile Trp Trp Asp Asp Lys Gly Tyr Asn Pro Ala
    50                  55                  60

Leu Lys Ser Arg Leu Thr Ile Ser Lys Asn Thr Ser Asn Leu Val
65                  70                  75                  80

Phe Leu Lys Ile Ala Ser Val Asp Thr Ala Asp Thr Ala Thr Tyr Tyr
                85                  90                  95

Cys Val Arg Ile Lys Gly Arg Met Asp Tyr Trp Gly Gln Gly Thr Ser
                100                 105                 110

Val Thr Val Ser Ser Lys Thr Thr Pro Pro Ser Val Tyr Pro Leu Ala
            115                 120                 125

Pro Gly Ser Ala Ala Gln Thr Asn Ser Met Val Thr Leu Gly Cys Leu
        130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Glu Ser Asp
                165                 170                 175

Leu Tyr Thr Leu Ser Ser Ser Val Thr Val Pro Ser Ser Pro Arg Pro
                180                 185                 190

```
Ser Glu Thr Val Thr Cys Asn Val Ala His Pro Ala Ser Ser Thr Lys
        195                 200                 205

Val Asp Lys Lys Ile Val Pro Arg Asp Cys Gly Cys Lys Pro Cys Ile
    210                 215                 220

Cys Thr Val Pro Glu Val Ser Ser Val Phe Ile Phe Pro Pro Lys Pro
225                 230                 235                 240

Lys Asp Val Leu Thr Ile Thr Leu Thr Pro Lys Val Thr Cys Val Val
                245                 250                 255

Val Asp Ile Ser Lys Asp Asp Pro Glu Val Gln Phe Ser Trp Phe Val
            260                 265                 270

Asp Asp Val Glu Val His Thr Ala Gln Thr Gln Pro Arg Glu Glu Gln
        275                 280                 285

Phe Asn Ser Thr Phe Arg Ser Val Ser Glu Leu Pro Ile Met His Gln
    290                 295                 300

Asp Trp Leu Asn Gly Lys Glu Phe Lys Cys Arg Val Asn Ser Ala Ala
305                 310                 315                 320

Phe Pro Ala Pro Ile Glu Lys Thr Ile Ser Lys Thr Lys Gly Arg Pro
                325                 330                 335

Lys Ala Pro Gln Val Tyr Thr Ile Pro Pro Pro Lys Glu Gln Met Ala
            340                 345                 350

Lys Asp Lys Val Ser Leu Thr Cys Met Ile Thr Asp Phe Phe Pro Glu
        355                 360                 365

Asp Ile Thr Val Glu Trp Gln Trp Asn Gly Gln Pro Ala Glu Asn Tyr
    370                 375                 380

Lys Asn Thr Gln Pro Ile Met Asn Thr Asn Gly Ser Tyr Phe Val Tyr
385                 390                 395                 400

Ser Lys Leu Asn Val Gln Lys Ser Asn Trp Glu Ala Gly Asn Thr Phe
                405                 410                 415

Thr Cys Ser Val Leu His Glu Gly Leu His Asn His His Thr Glu Lys
            420                 425                 430

Ser Leu Ser His Ser Pro Gly Lys
        435                 440

<210> SEQ ID NO 63
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asn Ile Met Met Thr Gln Ser Pro Ser Ser Leu Ala Val Ser Ala Gly
1               5                   10                  15

Glu Lys Val Thr Met Asn Cys Lys Ser Ser Gln Ser Val Leu Phe Gly
            20                  25                  30

Ser Lys Gln Lys Asn Tyr Leu Ala Trp Tyr Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Ile Leu Thr
65                  70                  75                  80

Ile Ser Asn Val Gln Ala Glu Asp Leu Ala Val Tyr Tyr Cys His Gln
                85                  90                  95

Tyr Leu Ser Leu Phe Thr Phe Gly Ser Gly Thr Lys Leu Glu Ile Lys
```

```
            100                 105                 110
Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
        130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 64
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Glu Gln Gln Lys Glu Ser Gly Gly Gly Leu Val Lys Pro Gly Ala
1               5                   10                  15

Ser Leu Thr Leu Thr Cys Thr Ala Ser Gly Ile Asp Phe Ser Ser Val
            20                  25                  30

Ala Tyr Met Cys Trp Val Arg Gln Ala Pro Gly Lys Gly Leu Glu Trp
        35                  40                  45

Ile Ala Cys Ile Tyr Ala Gly Ser Ser Ser Ile Tyr Tyr Ala Ser
    50                  55                  60

Trp Ala Lys Gly Arg Phe Thr Val Ser Arg Thr Ser Ser Thr Thr Val
65              70                  75                  80

Thr Leu Gln Met Thr Ser Leu Thr Ala Ala Asp Thr Ala Thr Tyr Phe
            85                  90                  95

Cys Ala Arg Gly Leu Phe Thr Ser Gly Ser Gly Tyr Tyr Ile Asp Met
            100                 105                 110

Trp Gly Pro Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240
```

```
Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 65
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Val Val Met Thr Gln Thr Pro Ser Ser Val Glu Val Ala Val Gly
1               5                   10                  15

Gly Thr Val Thr Ile Lys Cys Gln Ala Ser Gln Ser Ile Gly Ser Asn
            20                  25                  30

Leu Ala Trp Tyr Gln Gln Lys Pro Gly Gln Arg Pro Lys Leu Leu Ile
        35                  40                  45

Tyr Gly Ala Ser Asn Leu Ala Gly Val Pro Ser Arg Phe Ser Gly
    50                  55                  60

Ser Gly Ser Gly Thr Gln Phe Thr Leu Thr Ile Ser Asp Val Glu Cys
65                  70                  75                  80

Ala Asp Ala Ala Thr Tyr Tyr Cys Gln Arg Gly Tyr Ile Ser Ser Ala
                85                  90                  95

Val Asp Phe Phe Val Phe Gly Gly Gly Thr Glu Val Val Lys Gly
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140
```

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 66
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Ser
            20                  25                  30

Gly Thr Gly Val Gly Trp Ile Arg Gln Pro Ser Gly Lys Gly Leu Glu
        35                  40                  45

Trp Leu Ala His Ile Trp Trp Asp Asp Lys Gly Tyr Asn Pro Ala
50                  55                  60

Leu Lys Ser Arg Leu Thr Ile Ser Lys Asn Thr Ser Ser Asn Leu Val
65                  70                  75                  80

Phe Leu Lys Ile Ala Ser Val Asp Thr Ala Asp Thr Ala Thr Tyr Tyr
                85                  90                  95

Cys Val Arg Ile Lys Gly Arg Met Asp Tyr Trp Gly Gln Gly Thr Ser
            100                 105                 110

Val Thr Val Ser Ser Gly Gly Gly Gly Ser Gly Gly Gly Gly Ser Gly
        115                 120                 125

Gly Gly Gly Ser Gly Gly Gly Gly Ser Asn Ile Met Met Thr Gln Ser
130                 135                 140

Pro Ser Ser Leu Ala Val Ser Ala Gly Glu Lys Val Thr Met Asn Cys
145                 150                 155                 160

Lys Ser Ser Gln Ser Val Leu Phe Gly Ser Lys Gln Lys Asn Tyr Leu
                165                 170                 175

Ala Trp Tyr Gln Gln Lys Pro Gly Gln Ser Pro Lys Leu Leu Ile Tyr
            180                 185                 190

Trp Ala Ser Thr Arg Glu Ser Gly Val Pro Asp Arg Phe Thr Gly Ser
        195                 200                 205

Gly Ser Gly Thr Asp Phe Ile Leu Thr Ile Ser Asn Val Gln Ala Glu
        210                 215                 220

Asp Leu Ala Val Tyr Tyr Cys His Gln Tyr Leu Ser Leu Phe Thr Phe
225                 230                 235                 240

Gly Ser Gly Thr Lys Leu Glu Ile Lys
                245

<210> SEQ ID NO 67
<211> LENGTH: 256
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 67

Gln Glu Gln Gln Lys Glu Ser Gly Gly Gly Leu Val Lys Pro Gly Ala
1               5                   10                  15

Ser Leu Thr Leu Thr Cys Thr Ala Ser Gly Ile Asp Phe Ser Ser Val
            20                  25                  30

Ala Tyr Met Cys Trp Val Arg Gln Ala Pro Gly Lys Gly Leu Glu Trp
        35                  40                  45

Ile Ala Cys Ile Tyr Ala Gly Ser Ser Ser Ile Tyr Tyr Ala Ser
    50                  55                  60

Trp Ala Lys Gly Arg Phe Thr Val Ser Arg Thr Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Gly Leu Phe Thr Ser Gly Ser Gly Tyr Tyr Ile Asp Met
            100                 105                 110

Trp Gly Pro Gly Thr Leu Val Thr Val Ser Ser Gly Gly Gly Gly
            115                 120                 125

Ser Gly Gly Gly Ser Gly Gly Gly Ser Gly Gly Gly Gly Ser
        130                 135                 140

Asp Val Val Met Thr Gln Thr Pro Ser Ser Val Glu Val Ala Val Gly
145                 150                 155                 160

Gly Thr Val Thr Ile Lys Cys Gln Ala Ser Gln Ser Ile Gly Ser Asn
                165                 170                 175

Leu Ala Trp Tyr Gln Gln Lys Pro Gly Gln Arg Pro Lys Leu Leu Ile
            180                 185                 190

Tyr Gly Ala Ser Asn Leu Ala Ala Gly Val Pro Ser Arg Phe Ser Gly
        195                 200                 205

Ser Gly Ser Gly Thr Gln Phe Thr Leu Thr Ile Ser Asp Val Glu Cys
    210                 215                 220

Ala Asp Ala Ala Thr Tyr Tyr Cys Gln Arg Gly Tyr Ile Ser Ser Ala
225                 230                 235                 240

Val Asp Phe Phe Val Phe Gly Gly Thr Glu Val Val Val Lys Gly
                245                 250                 255

<210> SEQ ID NO 68
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Ser
            20                  25                  30

Gly Thr Gly Val Gly Trp Ile Arg Gln Pro Ser Gly Lys Gly Leu Glu
        35                  40                  45

Trp Leu Ala His Ile Trp Trp Asp Asp Asp Lys Gly Tyr Asn Pro Ala
    50                  55                  60

Leu Lys Ser Arg Leu Thr Ile Ser Lys Asn Thr Ser Ser Asn Leu Val
```

```
            65                  70                  75                  80
        Phe Leu Lys Ile Ala Ser Val Asp Thr Ala Asp Thr Ala Thr Tyr Tyr
                         85                  90                  95
        Cys Val Arg Ile Lys Gly Arg Met Asp Tyr Trp Gly Gln Gly Thr Ser
                        100                 105                 110
        Val Thr Val Ser Ser Gly Gly Gly Gly Ser Gly Gly Gly Gly Ser Gly
                        115                 120                 125
        Gly Gly Ser Gly Gly Gly Ser Asn Ile Met Met Thr Gln Ser
                130                 135                 140
        Pro Ser Ser Leu Ala Val Ser Ala Gly Glu Lys Val Thr Met Asn Cys
        145                 150                 155                 160
        Lys Ser Ser Gln Ser Val Leu Phe Ser Lys Gln Lys Asn Tyr Leu
                        165                 170                 175
        Ala Trp Tyr Gln Gln Lys Pro Gly Gln Ser Pro Lys Leu Leu Ile Tyr
                        180                 185                 190
        Trp Ala Ser Thr Arg Glu Ser Gly Val Pro Asp Arg Phe Thr Gly Ser
                        195                 200                 205
        Gly Ser Gly Thr Asp Phe Ile Leu Thr Ile Ser Asn Val Gln Ala Glu
                210                 215                 220
        Asp Leu Ala Val Tyr Tyr Cys His Gln Tyr Leu Ser Leu Phe Thr Phe
        225                 230                 235                 240
        Gly Ser Gly Thr Lys Leu Glu Ile Lys Thr Thr Pro Ala Pro Arg
                        245                 250                 255
        Pro Pro Thr Pro Ala Pro Thr Ile Ala Ser Gln Pro Leu Ser Leu Arg
                        260                 265                 270
        Pro Glu Ala Cys Arg Pro Ala Ala Gly Gly Ala Val His Thr Arg Gly
                        275                 280                 285
        Leu Asp Phe Ala Cys Asp Ile Tyr Ile Trp Ala Pro Leu Ala Gly Thr
                        290                 295                 300
        Cys Gly Val Leu Leu Leu Ser Leu Val Ile Thr Leu Tyr Cys Lys Arg
        305                 310                 315                 320
        Gly Arg Lys Lys Leu Leu Tyr Ile Phe Lys Gln Pro Phe Met Arg Pro
                        325                 330                 335
        Val Gln Thr Thr Gln Glu Glu Asp Gly Cys Ser Cys Arg Phe Pro Glu
                        340                 345                 350
        Glu Glu Glu Gly Gly Cys Glu Leu Arg Val Lys Phe Ser Arg Ser Ala
                        355                 360                 365
        Asp Ala Pro Ala Tyr Lys Gln Gly Gln Asn Gln Leu Tyr Asn Glu Leu
                        370                 375                 380
        Asn Leu Gly Arg Arg Glu Glu Tyr Asp Val Leu Asp Lys Arg Arg Gly
        385                 390                 395                 400
        Arg Asp Pro Glu Met Gly Gly Lys Pro Arg Arg Lys Asn Pro Gln Glu
                        405                 410                 415
        Gly Leu Tyr Asn Glu Leu Gln Lys Asp Lys Met Ala Glu Ala Tyr Ser
                        420                 425                 430
        Glu Ile Gly Met Lys Gly Glu Arg Arg Arg Gly Lys Gly His Asp Gly
                        435                 440                 445
        Leu Tyr Gln Gly Leu Ser Thr Ala Thr Lys Asp Thr Tyr Asp Ala Leu
                        450                 455                 460
        His Met Gln Ala Leu Pro Pro Arg
        465                 470

<210> SEQ ID NO 69
```

<211> LENGTH: 472
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

Asn Ile Met Met Thr Gln Ser Pro Ser Ser Leu Ala Val Ser Ala Gly
1               5                   10                  15

Glu Lys Val Thr Met Asn Cys Lys Ser Ser Gln Ser Val Leu Phe Gly
            20                  25                  30

Ser Lys Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Ile Leu Thr
65                  70                  75                  80

Ile Ser Asn Val Gln Ala Glu Asp Leu Ala Val Tyr Tyr Cys His Gln
                85                  90                  95

Tyr Leu Ser Leu Phe Thr Phe Gly Ser Gly Thr Lys Leu Glu Ile Lys
            100                 105                 110

Gly Gly Gly Gly Ser Gly Gly Gly Gly Ser Gly Gly Gly Gly Ser Gly
        115                 120                 125

Gly Gly Gly Ser Gln Val Thr Leu Lys Glu Ser Gly Pro Gly Ile Leu
    130                 135                 140

Gln Pro Ser Gln Thr Leu Ser Leu Thr Cys Ser Phe Ser Gly Phe Ser
145                 150                 155                 160

Leu Asn Thr Ser Gly Thr Gly Val Gly Trp Ile Arg Gln Pro Ser Gly
                165                 170                 175

Lys Gly Leu Glu Trp Leu Ala His Ile Trp Trp Asp Asp Lys Gly
            180                 185                 190

Tyr Asn Pro Ala Leu Lys Ser Arg Leu Thr Ile Ser Lys Asn Thr Ser
        195                 200                 205

Ser Asn Leu Val Phe Leu Lys Ile Ala Ser Val Asp Thr Ala Asp Thr
    210                 215                 220

Ala Thr Tyr Tyr Cys Val Arg Ile Lys Gly Arg Met Asp Tyr Trp Gly
225                 230                 235                 240

Gln Gly Thr Ser Val Thr Val Ser Ser Thr Thr Pro Ala Pro Arg
                245                 250                 255

Pro Pro Thr Pro Ala Pro Thr Ile Ala Ser Gln Pro Leu Ser Leu Arg
            260                 265                 270

Pro Glu Ala Cys Arg Pro Ala Ala Gly Gly Ala Val His Thr Arg Gly
        275                 280                 285

Leu Asp Phe Ala Cys Asp Ile Tyr Ile Trp Ala Pro Leu Ala Gly Thr
    290                 295                 300

Cys Gly Val Leu Leu Leu Ser Leu Val Ile Thr Leu Tyr Cys Lys Arg
305                 310                 315                 320

Gly Arg Lys Lys Leu Leu Tyr Ile Phe Lys Gln Pro Phe Met Arg Pro
                325                 330                 335

Val Gln Thr Thr Gln Glu Glu Asp Gly Cys Ser Cys Arg Phe Pro Glu
            340                 345                 350

Glu Glu Glu Gly Gly Cys Glu Leu Arg Val Lys Phe Ser Arg Ser Ala
        355                 360                 365

Asp Ala Pro Ala Tyr Lys Gln Gly Gln Asn Gln Leu Tyr Asn Glu Leu

```
                370                 375                 380
Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
            435                 440                 445

Leu Tyr Gln Gly Leu Ser Thr Ala Thr Lys Asp Thr Tyr Asp Ala Leu
450                 455                 460

His Met Gln Ala Leu Pro Pro Arg
465                 470

<210> SEQ ID NO 70
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Glu Gln Gln Lys Glu Ser Gly Gly Gly Leu Val Lys Pro Gly Ala
1               5                   10                  15

Ser Leu Thr Leu Thr Cys Thr Ala Ser Gly Ile Asp Phe Ser Ser Val
            20                  25                  30

Ala Tyr Met Cys Trp Val Arg Gln Ala Pro Gly Lys Gly Leu Glu Trp
        35                  40                  45

Ile Ala Cys Ile Tyr Ala Gly Ser Ser Ser Ile Tyr Tyr Ala Ser
    50                  55                  60

Trp Ala Lys Gly Arg Phe Thr Val Ser Arg Thr Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Gly Leu Phe Thr Ser Gly Ser Gly Tyr Tyr Ile Asp Met
            100                 105                 110

Trp Gly Pro Gly Thr Leu Val Thr Val Ser Ser Gly Gly Gly Gly
        115                 120                 125

Ser Gly Gly Gly Ser Gly Gly Gly Ser Gly Gly Gly Ser
    130                 135                 140

Asp Val Val Met Thr Gln Thr Pro Ser Ser Val Glu Val Ala Val Gly
145                 150                 155                 160

Gly Thr Val Thr Ile Lys Cys Gln Ala Ser Gln Ser Ile Gly Ser Asn
                165                 170                 175

Leu Ala Trp Tyr Gln Gln Lys Pro Gly Gln Arg Pro Lys Leu Leu Ile
            180                 185                 190

Tyr Gly Ala Ser Asn Leu Ala Ala Gly Val Pro Ser Arg Phe Ser Gly
        195                 200                 205

Ser Gly Ser Gly Thr Gln Phe Thr Leu Thr Ile Ser Asp Val Glu Cys
    210                 215                 220

Ala Asp Ala Ala Thr Tyr Tyr Cys Gln Arg Gly Tyr Ile Ser Ser Ala
225                 230                 235                 240

Val Asp Phe Phe Val Phe Gly Gly Gly Thr Glu Val Val Val Lys Gly
                245                 250                 255
```

Thr Thr Thr Pro Ala Pro Arg Pro Pro Thr Pro Ala Pro Thr Ile Ala
            260                 265                 270

Ser Gln Pro Leu Ser Leu Arg Pro Glu Ala Cys Arg Pro Ala Ala Gly
            275                 280                 285

Gly Ala Val His Thr Arg Gly Leu Asp Phe Ala Cys Asp Ile Tyr Ile
            290                 295                 300

Trp Ala Pro Leu Ala Gly Thr Cys Gly Val Leu Leu Leu Ser Leu Val
305                 310                 315                 320

Ile Thr Leu Tyr Cys Lys Arg Gly Arg Lys Lys Leu Leu Tyr Ile Phe
                325                 330                 335

Lys Gln Pro Phe Met Arg Pro Val Gln Thr Thr Gln Glu Glu Asp Gly
            340                 345                 350

Cys Ser Cys Arg Phe Pro Glu Glu Glu Glu Gly Gly Cys Glu Leu Arg
            355                 360                 365

Val Lys Phe Ser Arg Ser Ala Asp Ala Pro Ala Tyr Lys Gln Gly Gln
            370                 375                 380

Asn Gln Leu Tyr Asn Glu Leu Asn Leu Gly Arg Arg Glu Glu Tyr Asp
385                 390                 395                 400

Val Leu Asp Lys Arg Arg Gly Arg Asp Pro Glu Met Gly Gly Lys Pro
                405                 410                 415

Arg Arg Lys Asn Pro Gln Glu Gly Leu Tyr Asn Glu Leu Gln Lys Asp
            420                 425                 430

Lys Met Ala Glu Ala Tyr Ser Glu Ile Gly Met Lys Gly Glu Arg Arg
            435                 440                 445

Arg Gly Lys Gly His Asp Gly Leu Tyr Gln Gly Leu Ser Thr Ala Thr
            450                 455                 460

Lys Asp Thr Tyr Asp Ala Leu His Met Gln Ala Leu Pro Pro Arg
465                 470                 475

<210> SEQ ID NO 71
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Asp Val Val Met Thr Gln Thr Pro Ser Ser Val Glu Val Ala Val Gly
1               5                   10                  15

Gly Thr Val Thr Ile Lys Cys Gln Ala Ser Gln Ser Ile Gly Ser Asn
            20                  25                  30

Leu Ala Trp Tyr Gln Gln Lys Pro Gly Gln Arg Pro Lys Leu Leu Ile
        35                  40                  45

Tyr Gly Ala Ser Asn Leu Ala Ala Gly Val Pro Ser Arg Phe Ser Gly
    50                  55                  60

Ser Gly Ser Gly Thr Gln Phe Thr Leu Thr Ile Ser Asp Val Glu Cys
65                  70                  75                  80

Ala Asp Ala Ala Thr Tyr Tyr Cys Gln Arg Gly Tyr Ile Ser Ser Ala
                85                  90                  95

Val Asp Phe Phe Val Phe Gly Gly Thr Glu Val Val Lys Gly
            100                 105                 110

Gly Gly Gly Gly Gly Ser Gly Gly Gly Ser Gly Gly Gly Gly Ser
        115                 120                 125

Gly Gly Gly Gly Ser Glu Gln Gln Lys Glu Ser Gly Gly Gly Leu Val
    130                 135                 140

Lys Pro Gly Ala Ser Leu Thr Leu Thr Cys Thr Ala Ser Gly Ile Asp
145                 150                 155                 160

Phe Ser Ser Val Ala Tyr Met Cys Trp Val Arg Gln Ala Pro Gly Lys
                165                 170                 175

Gly Leu Glu Trp Ile Ala Cys Ile Tyr Ala Gly Ser Ser Ser Ser Ile
            180                 185                 190

Tyr Tyr Ala Ser Trp Ala Lys Gly Arg Phe Thr Val Ser Arg Thr Ser
        195                 200                 205

Ser Thr Thr Val Thr Leu Gln Met Thr Ser Leu Thr Ala Ala Asp Thr
    210                 215                 220

Ala Thr Tyr Phe Cys Ala Arg Gly Leu Phe Thr Ser Gly Ser Gly Tyr
225                 230                 235                 240

Tyr Ile Asp Met Trp Gly Pro Gly Thr Leu Val Thr Val Ser Ser Thr
                245                 250                 255

Thr Thr Pro Ala Pro Arg Pro Pro Thr Pro Ala Pro Thr Ile Ala Ser
            260                 265                 270

Gln Pro Leu Ser Leu Arg Pro Glu Ala Cys Arg Pro Ala Ala Gly Gly
        275                 280                 285

Ala Val His Thr Arg Gly Leu Asp Phe Ala Cys Asp Ile Tyr Ile Trp
    290                 295                 300

Ala Pro Leu Ala Gly Thr Cys Gly Val Leu Leu Leu Ser Leu Val Ile
305                 310                 315                 320

Thr Leu Tyr Cys Lys Arg Gly Arg Lys Lys Leu Leu Tyr Ile Phe Lys
                325                 330                 335

Gln Pro Phe Met Arg Pro Val Gln Thr Thr Gln Glu Glu Asp Gly Cys
            340                 345                 350

Ser Cys Arg Phe Pro Glu Glu Glu Gly Gly Cys Glu Leu Arg Val
        355                 360                 365

Lys Phe Ser Arg Ser Ala Asp Ala Pro Ala Tyr Lys Gln Gly Gln Asn
    370                 375                 380

Gln Leu Tyr Asn Glu Leu Asn Leu Gly Arg Arg Glu Glu Tyr Asp Val
385                 390                 395                 400

Leu Asp Lys Arg Arg Gly Arg Asp Pro Glu Met Gly Gly Lys Pro Arg
                405                 410                 415

Arg Lys Asn Pro Gln Glu Gly Leu Tyr Asn Glu Leu Gln Lys Asp Lys
            420                 425                 430

Met Ala Glu Ala Tyr Ser Glu Ile Gly Met Lys Gly Glu Arg Arg Arg
        435                 440                 445

Gly Lys Gly His Asp Gly Leu Tyr Gln Gly Leu Ser Thr Ala Thr Lys
    450                 455                 460

Asp Thr Tyr Asp Ala Leu His Met Gln Ala Leu Pro Pro Arg
465                 470                 475

<210> SEQ ID NO 72
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Thr Ser Val

```
            20                  25                  30
Met Gly Trp Val Arg Gln Ala Pro Gly Lys Gly Leu Glu Ser Ile Gly
            35                  40                  45

Phe Ile Tyr Thr Asn Val Asn Thr Tyr Tyr Ala Ser Trp Ala Lys Gly
        50                  55                  60

Arg Phe Thr Ile Ser Arg Thr Ser Thr Thr Val Asp Leu Lys Ile Thr
 65                  70                  75                  80

Ser Pro Thr Thr Gly Asp Thr Ala Thr Tyr Phe Cys Ala Arg Ala Val
                85                  90                  95

Tyr Ala Gly Ala Met Asp Leu Trp Gly Gln Gly Thr Leu Val Thr Val
            100                 105                 110

Ser Ser Gly Gly Gly Gly Ser Gly Gly Gly Ser Gly Gly Gly Gly
            115                 120                 125

Ser Gly Gly Gly Gly Ser Asp Val Val Met Thr Gln Thr Pro Ala Ser
        130                 135                 140

Val Ser Gly Pro Val Gly Gly Thr Val Thr Ile Lys Cys Gln Ala Ser
145                 150                 155                 160

Glu Arg Ile Tyr Ser Asn Leu Ala Trp Tyr Gln Gln Lys Pro Gly Gln
                165                 170                 175

Pro Pro Lys Leu Leu Ile Tyr Lys Ala Ser Thr Leu Ala Ser Gly Val
            180                 185                 190

Ser Ser Arg Phe Lys Gly Ser Gly Ser Gly Thr Glu Phe Thr Leu Thr
            195                 200                 205

Ile Arg Asp Leu Glu Cys Ala Asp Ala Ala Thr Tyr Ser Cys Gln Tyr
        210                 215                 220

Thr Ser Tyr Gly Ser Gly Tyr Val Gly Thr Phe Gly Gly Gly Thr Glu
225                 230                 235                 240

Val Val Val Glu Gly
                245

<210> SEQ ID NO 73
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Asp Val Val Met Thr Gln Thr Pro Ala Ser Val Ser Gly Pro Val Gly
 1               5                  10                  15

Gly Thr Val Thr Ile Lys Cys Gln Ala Ser Glu Arg Ile Tyr Ser Asn
                20                  25                  30

Leu Ala Trp Tyr Gln Gln Lys Pro Gly Gln Pro Pro Lys Leu Leu Ile
            35                  40                  45

Tyr Lys Ala Ser Thr Leu Ala Ser Gly Val Ser Ser Arg Phe Lys Gly
        50                  55                  60

Ser Gly Ser Gly Thr Glu Phe Thr Leu Thr Ile Arg Asp Leu Glu Cys
 65                  70                  75                  80

Ala Asp Ala Ala Thr Tyr Ser Cys Gln Tyr Thr Ser Tyr Gly Ser Gly
                85                  90                  95

Tyr Val Gly Thr Phe Gly Gly Gly Thr Glu Val Val Val Glu Gly Gly
            100                 105                 110

Gly Gly Gly Ser Gly Gly Gly Gly Ser Gly Gly Gly Gly Ser Gly Gly
            115                 120                 125
```

```
Gly Gly Ser Leu Glu Glu Ser Gly Gly Arg Leu Val Thr Pro Gly Thr
130                 135                 140
Pro Leu Thr Leu Thr Cys Thr Val Ser Gly Ile Asp Leu Ser Thr Ser
145                 150                 155                 160
Val Met Gly Trp Val Arg Gln Ala Pro Gly Lys Gly Leu Glu Ser Ile
                165                 170                 175
Gly Phe Ile Tyr Thr Asn Val Asn Thr Tyr Tyr Ala Ser Trp Ala Lys
                180                 185                 190
Gly Arg Phe Thr Ile Ser Arg Thr Ser Thr Val Asp Leu Lys Ile
                195                 200                 205
Thr Ser Pro Thr Thr Gly Asp Thr Ala Thr Tyr Phe Cys Ala Arg Ala
210                 215                 220
Val Tyr Ala Gly Ala Met Asp Leu Trp Gly Gln Gly Thr Leu Val Thr
225                 230                 235                 240
Val Ser Ser
```

<210> SEQ ID NO 74
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Gln Val Thr Leu Lys Glu Ser Gly Pro Gly Ile Leu Gln Pro Ser Gln
1               5                   10                  15
Thr Leu Ser Leu Thr Cys Ser Phe Ser Gly Phe Ser Leu Asn Thr Ser
                20                  25                  30
Gly Thr Gly Val Gly Trp Ile Arg Gln Pro Ser Gly Lys Gly Leu Glu
            35                  40                  45
Trp Leu Ala His Ile Trp Trp Asp Asp Asp Lys Gly Tyr Asn Pro Ala
        50                  55                  60
Leu Lys Ser Arg Leu Thr Ile Ser Lys Asn Thr Ser Ser Asn Leu Val
65                  70                  75                  80
Phe Leu Lys Ile Ala Ser Val Asp Thr Ala Asp Thr Ala Thr Tyr Tyr
                85                  90                  95
Cys Val Arg Ile Lys Gly Arg Met Asp Tyr Trp Gly Gln Gly Thr Ser
                100                 105                 110
Val Thr Val Ser Ser
            115
```

<210> SEQ ID NO 75
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

```
Asn Ile Met Met Thr Gln Ser Pro Ser Ser Leu Ala Val Ser Ala Gly
1               5                   10                  15
Glu Lys Val Thr Met Asn Cys Lys Ser Ser Gln Ser Val Leu Phe Gly
                20                  25                  30
Ser Lys Gln Lys Asn Tyr Leu Ala Trp Tyr Gln Gln Lys Pro Gly Gln
            35                  40                  45
Ser Pro Lys Leu Leu Ile Tyr Trp Ala Ser Thr Arg Glu Ser Gly Val
```

```
                50                  55                  60
Pro Asp Arg Phe Thr Gly Ser Gly Ser Gly Thr Asp Phe Ile Leu Thr
 65                  70                  75                  80

Ile Ser Asn Val Gln Ala Glu Asp Leu Ala Val Tyr Tyr Cys His Gln
                 85                  90                  95

Tyr Leu Ser Leu Phe Thr Phe Gly Ser Gly Thr Lys Leu Glu Ile Lys
            100                 105                 110
```

<210> SEQ ID NO 76
<211> LENGTH: 350
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 76

```
aggttactct gaaagagtct ggccctggga tattgcagcc ctcccagacc ctcagtctga   60
cttgttcttt ctctgggttt tcactgaaca cttctggtac gggtgtaggc tggattcgtc  120
agccttcagg gaagggtctg gagtggctgg cacacatttg gtgggatgat gacaagggt  180
ataacccagc cctgaagagc cgactgacaa tctccaaaaa cacctccagc aacctggtat  240
tcctcaagat cgccagtgtg gacactgcag atactgccac atattactgt gttcgaatca  300
aaggccggat ggactactgg ggtcaaggaa cctcagtcac cgtctcctca              350
```

<210> SEQ ID NO 77
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 77

```
aacattatga tgacacagtc gccatcctct ctggctgtgt ctgcaggaga aaaggtcact   60
atgaactgta gtccagtca agtgttttta ttcggttcaa acagaagaa ctatttggcc   120
tggtaccagc agaaaccagg gcagtctcct aaattgctga tctactgggc atccactagg  180
gaatctggtg tccctgatcg cttcacaggc agtggatctg gacagattt tatacttacc  240
atcagcaatg tacaagctga agacctggca gtttattact gtcatcaata cctctcccta  300
ttcacgttcg gctcggggac aaagttggaa ataaaa                             336
```

<210> SEQ ID NO 78
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 78

```
Gln Glu Gln Gln Lys Glu Ser Gly Gly Gly Leu Val Lys Pro Gly Ala
 1               5                  10                  15

Ser Leu Thr Leu Thr Cys Thr Ala Ser Gly Ile Asp Phe Ser Ser Val
             20                  25                  30

Ala Tyr Met Cys Trp Val Arg Gln Ala Pro Gly Lys Gly Leu Glu Trp
         35                  40                  45

Ile Ala Cys Ile Tyr Ala Gly Ser Ser Ser Ile Tyr Tyr Ala Ser
     50                  55                  60
```

Trp Ala Lys Gly Arg Phe Thr Val Ser Arg Thr Ser Thr Thr Val
65                  70                  75                  80

Thr Leu Gln Met Thr Ser Leu Thr Ala Ala Asp Thr Ala Thr Tyr Phe
            85                  90                  95

Cys Ala Arg Gly Leu Phe Thr Ser Gly Ser Tyr Tyr Ile Asp Met
            100                 105                 110

Trp Gly Pro Gly Thr Leu Val Thr Val Ser Ser
        115                 120

<210> SEQ ID NO 79
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Asp Val Val Met Thr Gln Thr Pro Ser Ser Val Glu Val Ala Val Gly
1               5                   10                  15

Gly Thr Val Thr Ile Lys Cys Gln Ala Ser Gln Ser Ile Gly Ser Asn
            20                  25                  30

Leu Ala Trp Tyr Gln Gln Lys Pro Gly Gln Arg Pro Lys Leu Leu Ile
        35                  40                  45

Tyr Gly Ala Ser Asn Leu Ala Ala Gly Val Pro Ser Arg Phe Ser Gly
    50                  55                  60

Ser Gly Ser Gly Thr Gln Phe Thr Leu Thr Ile Ser Asp Val Glu Cys
65                  70                  75                  80

Ala Asp Ala Ala Thr Tyr Tyr Cys Gln Arg Gly Tyr Ile Ser Ser Ala
                85                  90                  95

Val Asp Phe Phe Val Phe Gly Gly Gly Thr Glu Val Val Val Lys Gly
            100                 105                 110

<210> SEQ ID NO 80
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
caggagcagc agaaggagtc cgggggaggc ctggtcaagc ctggggcatc cctgacactc      60
acctgcacag cttctggaat cgacttcagt agtgtcgcct acatgtgttg ggtccgccag     120
gctccaggga aggggctgga gtggatcgca tgcatttatg ctggtagtag tagtagcatc     180
tactacgcga gctgggcgaa aggccgattc accgtctcca gaacctcgtc taccacggtg     240
actctgcaaa tgaccagtct gacagccgcg gacacggcca cctatttctg tgcgagaggt     300
ctatttacta gtggtagtgg atattatata gacatgtggg gcccaggcac cctggtcacc     360
gtctcctca                                                             369

<210> SEQ ID NO 81
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

```
gatgtcgtga tgacccagac tccatcctct gtggaggtag ctgtgggagg cacagtcacc      60
atcaagtgcc aggccagtca gagcattggt agtaatttag cctggtatca gcagaaacca     120
gggcagcgtc ccaagctcct gatctatggt gcatccaatc tggccgctgg ggtcccatcg     180
cggttcagtg gcagtggatc tgggacacag ttcactctca ccatcagcga cgtggagtgt     240
gccgatgctg ccacttacta ctgtcaacgg ggttatatta gcagtgctgt tgatttttt      300
gttttcggcg gagggaccga ggtggtggtc aaaggt                               336
```

<210> SEQ ID NO 82
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

```
Asn Ile Met Met Thr Gln Ser Pro Ser Ser Leu Ala Val Ser Ala Gly
1               5                   10                  15
Glu Lys Val Thr Met Asn Cys Lys Ser Ser Gln Ser Val Leu Phe Gly
            20                  25                  30
Ser Lys Gln Lys Asn Tyr Leu Ala Trp Tyr Gln Gln Lys Pro Gly Gln
        35                  40                  45
Ser Pro Lys Leu Leu Ile Tyr Trp Ala Ser Thr Arg Glu Ser Gly Val
    50                  55                  60
Pro Asp Arg Phe Thr Gly Ser Gly Ser Gly Thr Asp Phe Ile Leu Thr
65                  70                  75                  80
Ile Ser Asn Val Gln Ala Glu Asp Leu Ala Val Tyr Tyr Cys His Gln
                85                  90                  95
Tyr Leu Ser Leu Phe Thr Phe Gly Ser Gly Thr Lys Leu Glu Ile Lys
            100                 105                 110
Gly Gly Gly Gly Ser Gly Gly Gly Ser Gly Gly Gly Gly Ser Gly
        115                 120                 125
Gly Gly Gly Ser Gln Val Thr Leu Lys Glu Ser Gly Pro Gly Ile Leu
    130                 135                 140
Gln Pro Ser Gln Thr Leu Ser Leu Thr Cys Ser Phe Ser Gly Phe Ser
145                 150                 155                 160
Leu Asn Thr Ser Gly Thr Gly Val Gly Trp Ile Arg Gln Pro Ser Gly
                165                 170                 175
Lys Gly Leu Glu Trp Leu Ala His Ile Trp Trp Asp Asp Lys Gly
            180                 185                 190
Tyr Asn Pro Ala Leu Lys Ser Arg Leu Thr Ile Ser Lys Asn Thr Ser
        195                 200                 205
Ser Asn Leu Val Phe Leu Lys Ile Ala Ser Val Asp Thr Ala Asp Thr
    210                 215                 220
Ala Thr Tyr Tyr Cys Val Arg Ile Lys Gly Arg Met Asp Tyr Trp Gly
225                 230                 235                 240
Gln Gly Thr Ser Val Thr Val Ser Ser
                245
```

<210> SEQ ID NO 83
<211> LENGTH: 256
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 83

Asp Val Val Met Thr Gln Thr Pro Ser Ser Val Glu Val Ala Val Gly
1               5                   10                  15

Gly Thr Val Thr Ile Lys Cys Gln Ala Ser Gln Ser Ile Gly Ser Asn
            20                  25                  30

Leu Ala Trp Tyr Gln Gln Lys Pro Gly Gln Arg Pro Lys Leu Leu Ile
        35                  40                  45

Tyr Gly Ala Ser Asn Leu Ala Ala Gly Val Pro Ser Arg Phe Ser Gly
    50                  55                  60

Ser Gly Ser Gly Thr Gln Phe Thr Leu Thr Ile Ser Asp Val Glu Cys
65                  70                  75                  80

Ala Asp Ala Ala Thr Tyr Tyr Cys Gln Arg Gly Tyr Ile Ser Ser Ala
                85                  90                  95

Val Asp Phe Phe Val Phe Gly Gly Thr Glu Val Val Val Lys Gly
            100                 105                 110

Gly Gly Gly Gly Ser Gly Gly Gly Gly Ser Gly Gly Gly Gly Ser
        115                 120                 125

Gly Gly Gly Ser Gln Glu Gln Leu Lys Glu Ser Gly Gly Gly Leu
    130                 135                 140

Val Lys Pro Gly Ala Ser Leu Thr Leu Thr Cys Thr Ala Ser Gly Ile
145                 150                 155                 160

Asp Phe Ser Ser Val Ala Tyr Met Cys Trp Val Arg Gln Ala Pro Gly
                165                 170                 175

Lys Gly Leu Glu Trp Ile Ala Cys Ile Tyr Ala Gly Ser Ser Ser Ser
            180                 185                 190

Ile Tyr Tyr Ala Ser Trp Ala Lys Gly Arg Phe Thr Val Ser Arg Thr
        195                 200                 205

Ser Ser Thr Thr Val Thr Leu Gln Met Thr Ser Leu Thr Ala Ala Asp
    210                 215                 220

Thr Ala Thr Tyr Phe Cys Ala Arg Gly Leu Phe Thr Ser Gly Ser Gly
225                 230                 235                 240

Tyr Tyr Ile Asp Met Trp Gly Pro Gly Thr Leu Val Thr Val Ser Ser
                245                 250                 255

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 84

Gly Ser Gly Ser Gly Ser Gly Ser Gly Ser Gly Ser
1               5                   10

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 85

Asp Trp Glu Tyr Ser Val Trp Leu Ser

```
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Ser Pro Val Thr Ala Arg Val Leu
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Leu Thr Ser Ser Leu Arg Tyr Asn
1               5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Met Glu Val Gly Trp Tyr Arg Pro
1               5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Gly Gln Phe Leu Glu Glu Arg
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Tyr Arg Pro Pro Phe Ser Arg Val Val
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Pro Met Thr Leu Pro Glu Asn Tyr Phe
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Trp Asn Pro Asp Asp Tyr Gly Gly Ile
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Lys Lys Gly Trp Lys His Trp Val Tyr
1               5
```